(12) United States Patent
DiRusso et al.

(10) Patent No.: US 10,351,883 B2
(45) Date of Patent: Jul. 16, 2019

(54) COMPOUNDS FOR INCREASING LIPID SYNTHESIS AND STORAGE

(71) Applicant: NUtech Ventures, Lincoln, NE (US)

(72) Inventors: Concetta DiRusso, Lincoln, NE (US); Nishikant Wase, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 131 days.

(21) Appl. No.: 15/138,066

(22) Filed: Apr. 25, 2016

(65) Prior Publication Data

US 2016/0312253 A1 Oct. 27, 2016

Related U.S. Application Data

(60) Provisional application No. 62/152,717, filed on Apr. 24, 2015.

(51) Int. Cl.

| | |
|---|---|
| *C12P 7/64* | (2006.01) |
| *C12P 19/04* | (2006.01) |
| *C07C 217/60* | (2006.01) |
| *C07D 295/135* | (2006.01) |
| *C07C 211/40* | (2006.01) |
| *C07D 231/40* | (2006.01) |
| *C07C 233/75* | (2006.01) |
| *C07D 213/40* | (2006.01) |
| *C07D 211/58* | (2006.01) |
| *C07D 211/96* | (2006.01) |
| *C07D 277/46* | (2006.01) |
| *C12N 1/38* | (2006.01) |

(52) U.S. Cl.
CPC .......... *C12P 7/6409* (2013.01); *C07C 211/40* (2013.01); *C07C 217/60* (2013.01); *C07C 233/75* (2013.01); *C07D 211/58* (2013.01); *C07D 211/96* (2013.01); *C07D 213/40* (2013.01); *C07D 231/40* (2013.01); *C07D 277/46* (2013.01); *C07D 295/135* (2013.01); *C12N 1/38* (2013.01); *C12P 7/6463* (2013.01); *C12P 19/04* (2013.01)

(58) Field of Classification Search
None
See application file for complete search history.

(56) References Cited

PUBLICATIONS

Berge et al., "Pharmaceutical Salts," Journal of Pharmaceutical Sciences, Jan. 1977, 66(1): 1-19.

Chisti, "Biodiesel from microalgae," Biotechnology Advances, 2007, 25:294-306.

Deng et al., "The mRNA abundance of pepc2 gene is negatively correlated with oil content in Chlamydomonas reinhardtee," Biomass and Bioenergy, 2011, 35:1811-1817.

Garnier et al., "Comparative proteomics reveals proteins impacted by nitrogen deprivation in wild-type and high lipid-accumulating mutant strains of Tisochrysis lutea," Journal of Proteomics, Jun. 2014, 105:107-120.

Hannon et al., "Biofuels from algae: challenges and potential," Biofuels, Sep. 2010, 1(5):763-784.

(Continued)

*Primary Examiner* — Erin M. Bowers
(74) *Attorney, Agent, or Firm* — Fish & Richardson P.C.

(57) ABSTRACT

This invention relates to methods for increasing lipid accumulation and lipid production in cells. Methods of producing biofuel from cells and preparing nutraceuticals comprising lipids produced according to a method provided herein are also provided.

8 Claims, 16 Drawing Sheets

(56) References Cited

PUBLICATIONS

Hu et al., "Microalgal triacylglycerols as feedstocks for biofuel production: perspectives and advances," The Plant Journal, 2008, 54:621-639.

Msanne et al., "Metabolic and gene expression changes triggered by nitrogen deprivation in the photoautotrophically grown microalgae *Chlamydomonas reinhardtii* and *Coccomyxa* sp. C-169," Phytochemistry, 2012, 75:50-59.

Singh et al., "Mechanism and challenges in commercialization of algal biofuels," Bioresource Technology, Jan. 2011, 102:26-34.

Wase et al., "Integrated Quantitative Analysis of Nitrogen Stress Response in Chlamydomonas reinhardtee Using Metabolite and Protein Profiling," Journal of Proteome Research, 2014, 13:1373-1396.

| Compound | EC50 µM | Structure | Nile Red | Chlorophyll |
|---|---|---|---|---|
| Control | | | | |
| 62 | 1.39 | 4-((4-(2-methoxyphenyl) piperazin-1-yl) methyl) phenol | | |
| 1 | 1.43 | 2-(3,4-dimethoxyphenyl)-N-methyl-N-(4-nitrobenzyl) ethan-1-amine | | |
| 136 | 5.33 | 3-(adamantan-1-yl (methyl) amino) propanenitrile | | |

FIG. 1

Compound 1

Compound 136
　i.　2.8
　ii.　8.7

Compound 144
　i.　2.6
　ii.　11.6

COMPOUNDS FOR INCREASING LIPID SYNTHESIS AND STORAGE

CROSS REFERENCE TO RELATED APPLICATIONS

This application claims the benefit of U.S. Provisional Application Ser. No. 62/152,717, filed Apr. 24, 2015, the disclosure of which is incorporated herein by reference in its entirety.

FEDERALLY SPONSORED RESEARCH OR DEVELOPMENT

This invention was made with Government support under Grant Nos. EPS-1004094 and 1264409, awarded by the National Science Foundation. The Government has certain rights in the invention.

TECHNICAL FIELD

This invention relates to methods for increasing lipid accumulation and lipid production in cells.

BACKGROUND

Algae are a diverse group of microorganisms that include species that inhabit marine, freshwater and terrestrial niches. It is estimated that 30-50% of the net photosynthetic productivity on plant earth is contributed by phytoplankton including algae. Algae may also be employed for the production of biofuels, and can be grown in poor quality water and under a large variety of environmental conditions (see, e.g., Singh et al., *Bioresource Technology*, 2011, 102, 26-34 and Hu et al., *The Plant Journal*, 2008, 54, 621-639). Additionally, during photosynthesis algae fix $CO_2$ into biomass thus addressing concerns about the generation of carbon emissions.

SUMMARY

The present application provides, inter alia, a method of increasing lipid accumulation in a cell, comprising contacting the cell with an effective amount of a compound of Formula Ia:

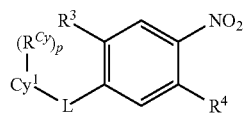

Ia or a pharmaceutically acceptable salt thereof, wherein:
L is selected from the group consisting of a bond, $C_{1-4}$ alkylene, $C_{1-4}$ hydroxyalkylene, $C_{1-4}$ alkyleneoxy, —($C_{1-4}$ alkylene)-$NR^L$—($C_{1-4}$ alylene)$_n$-, C(=O), and C(=O)NH;
$R^L$ is selected from the group consisting of H and methyl;
$R^3$ is H or $C_{1-4}$ alkoxy;
$R^4$ is selected from the group consisting of H and piperidinyl;
$Cy^1$ is selected from the group consisting of phenyl, $C_{3-8}$ cycloalkyl, 4-6 membered heterocycloalkyl, and 4-10 membered heteroaryl;
$R^{Cy}$ is selected from the group consisting of halo, $C_{1-4}$ alkyl, $C_{1-4}$ alkoxy, phenyl, —($C_{1-4}$ alkylene)-(phenyl), $C_{3-10}$ cycloalkyl, and —($C_{1-4}$ alkylene)-($C_{3-10}$ cyloalkyl), wherein each phenyl and the phenyl group of —($C_{1-4}$ alkylene)-(phenyl) is optionally substituted by 1 or 2 substituents independently selected from the group consisting of OH, halo, $C_{1-4}$ alkyl, and $C_{1-4}$ alkoxy;

n is 0 or 1; and
p is 0, 1, 2, 3, 4, or 5; or
a compound of Formula Ib:

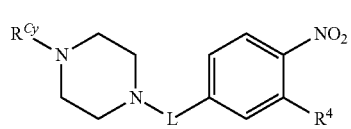

Ib or a pharmaceutically acceptable salt thereof, wherein:
L is selected from the group consisting of a bond, $C_{1-4}$ alkylene, $C_{1-4}$ hydroxyalkylene, and C(=O);
$R^4$ is selected from the group consisting of H and piperidinyl; and
$R^{Cy}$ is selected from the group consisting of $C_{1-4}$ alkyl, phenyl, —($C_{1-4}$ alkylene)-(phenyl), $C_{3-10}$ cycloalkyl, and —($C_{1-4}$ alkylene)-($C_{3-10}$ cyloalkyl), wherein each phenyl and the phenyl group of —($C_{1-4}$ alkylene)-(phenyl) is optionally substituted by 1 or 2 substituents independently selected from the group consisting of OH, halo, $C_{1-4}$ alkyl, and $C_{1-4}$ alkoxy; or
a compound of Formula Ic:

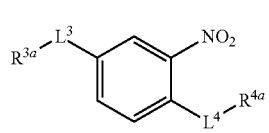

Ic or a pharmaceutically acceptable salt thereof, wherein:
$L^3$ is selected from the group consisting of a bond and C(O)NH;
$R^{3a}$ is selected from the group consisting of H, $C_{1-4}$ alkyl, $C_{1-4}$ alkoxy, -phenyl-($C_{1-4}$ alkylene)-$R^b$, -(phenyl)-$SO_2R^b$, and 5-6 membered heteroaryl, wherein the 5-6 membered heteroaryl is optionally substituted with a $C_{1-4}$ alkyl group;
$R^b$ is selected from the group consisting of 5-6 membered heteroaryl and 5-6 membered heterocycloalkyl, wherein the 5-6 membered heterocycloalkyl is optionally substituted by a $C_{1-4}$ alkyl group;
$L^4$ is selected from the group consisting of a bond, S, C(=O)NH, $C_{1-6}$ alkyleneoxy, and $SO_2$-$Cy^2$-$Cy^3$;
$Cy^2$ and $Cy^3$ are each an independently selected 5-6 membered heterocycloalkyl group; and
$R^{4a}$ is selected from the group consisting of H, $C_{1-4}$ alkyl, —($C_{1-4}$ alkylene)-($C_{3-6}$ cycloalkyl), 5-6 membered heterocyloalkyl, and —($C_{1-4}$ alkylene)-(phenyl); or
a compound of Formula IIa:

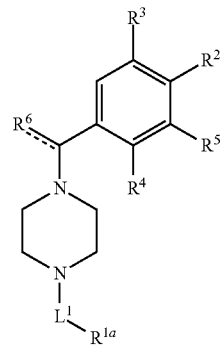

IIa or a pharmaceutically acceptable salt thereof, wherein:
$L^1$ is selected from the group consisting of a bond, $C_{1-4}$ alkylene, $C_{2-4}$ alkenylene, $C_{1-4}$ hydroxyalkylene, $C_{1-4}$ alkyleneoxy, 4-6 membered heterocycloalkylene, and C(=O), wherein the $C_{1-4}$ alkyleneoxy is further optionally substituted by one OH group;

$R^{1a}$ is selected from the group consisting of OH, $C_{1-4}$ alkyl, $C_{5-10}$ cycloalkyl, 8-10 membered heteroaryl, phenyl, —($C_{1-4}$ alkylene)-(phenyl), and 10-13 membered heteroaryl, wherein the $C_{5-10}$ cycloalkyl, phenyl, and the phenyl group of the —($C_{1-4}$ alkylene)-(phenyl) are each optionally substituted by 1, 2, or 3 substituents independently selected from the group consisting of halo, OH, $NO_2$, $C_{1-4}$ alkyl, and $C_{1-4}$ alkoxy, and wherein the 10-13 membered heteroaryl is optionally substituted by one halo group;

$R^2$ is selected from the group consisting of H, halo, OH, $NO_2$, $C_{1-4}$ alkyl, $C_{1-4}$ alkoxy, and —($C_{1-4}$ alkylene)-(8-10 membered heteroaryl);

$R^3$ is selected from the group consisting of H, halo, $C_{1-4}$ alkoxy, and phenoxy; or alternatively, $R^2$ and $R^3$ come together, in combination with the carbon atoms to which they are attached, to form a 5-6 membered heterocycloalkyl or a $C_{6-10}$ aryl;

$R^4$ is selected from the group consisting of H, OH, and $C_{1-4}$ alkoxy;

$R^5$ is selected from the group consisting of H, halo, $C_{1-4}$ alkoxy, and phenoxy; and $R^6$ is selected from the group consisting of H and oxo; or a compound of Formula IIIa:

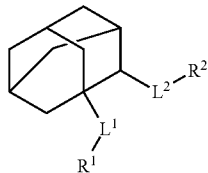

IIIa or a pharmaceutically acceptable salt thereof, wherein:

$L^1$ is selected from the group consisting of a bond, NH, N($C_{1-4}$ alkyl), $C_{2-4}$ alkynyl, NHC(=O)($C_{1-4}$ thioalkyl), $C_{1-6}$ alkyleneoxy, 5-6 membered heterocycloalkyl, NHC(=O)$C_{1-4}$ alkylene, and ($C_{1-4}$ alkylene)-NHC(=O)—($C_{1-4}$ alkylene)-, wherein the $C_{1-6}$ alkyleneoxy is further optionally substituted by one OH group;

$R^{1a}$ is selected from the group consisting of H, $C_{1-4}$ alkyl, $C_{2-4}$ alkenyl, $C_{1-4}$ cyanoalkylene, 5-6 membered heterocycloalkyl, 5-6 membered heteroaryl, NH($C_{1-4}$ alkyl), and NH($C_{2-4}$ alkenyl), wherein the $C_{1-4}$ alkyl and $C_{2-4}$ alkenyl are each optionally substituted by one substituent selected from the group consisting of phenyl and hydroxyphenyl, and wherein the 5-6 membered heterocycloalkyl and 5-6 membered heteroaryl are each optionally substituted by 1 or 2 substituents independently selected from the group consisting of $C_{1-4}$ alkyl, $NH_2$ and di-halo substituted phenyl;

$L^2$ is selected from the group consisting of a bond and 5-6 membered heterocycloalkyl; and $R^{2a}$ is selected from the group consisting of H, $C_{1-4}$ hydroxyalkyl, —$SO_2$($C_{1-4}$ alkyl).

In some embodiments, the compound is a compound of Formula Ia. In some embodiments, the compound is a compound of Formula IIa. In some embodiments, the compound is a compound of Formula IIIa.

In some embodiments, the cell is a eukaryotic cell or a cyanobacteria. In some embodiments, the cell is selected from the group consisting of an algal cell, a *drosophila* cell, a yeast cell, or a fungus cell. In some embodiments, the cell is an algal cell. In some embodiments, the cell is selected from the group consisting of:

*Chlamydomonas reinhardtii;*
*Chlorella sorokiniana;*
*Tetrachlorella alterans;*
*C. protothecoides;*
*C. vulgaris;* and
*Nannochloropsis* sp.

In some embodiments, the increasing lipid accumulation comprises increasing fatty acid accumulation. In some embodiments, the increasing lipid accumulation comprises increasing polyunsaturated fatty acid accumulation. In some embodiments, the increasing lipid accumulation comprises increasing triacylglycerol accumulation. In some embodiments, the increasing lipid accumulation comprises increasing fatty acid accumulation and increasing triacylglycerol accumulation. In some embodiments, the increasing lipid accumulation comprises increasing polyunsaturated fatty acid accumulation and increasing triacylglycerol accumulation.

In some embodiments, the method further comprises increasing carbohydrate accumulation in the cell. In some embodiments, the method further comprises increasing carbohydrate production in the cell.

In some embodiments, the lipid accumulation is increased by greater than about 1.5-fold as compared to a cell that has not been contacted by the compound. In some embodiments, the lipid accumulation is increased by greater than about 2-fold as compared to a cell that has not been contacted by the compound. In some embodiments, the lipid accumulation is increased by greater than about 2.5-fold as compared to a cell that has not been contacted by the compound.

In some embodiments, the contacting the cell with the compound does not reduce the rate of cellular growth compared to a cell that has not been contacted by the compound. In some embodiments, contacting the cell with the compound does not reduce the rate of photosynthesis of the cell compared to a cell that has not been contacted by the compound. In some embodiments, the contacting does not adversely affect the viability of the cell.

In some embodiments, the lipid accumulation is increased without exposing the cell to environmental stress. In some embodiments, the environmental stress comprises nutrient deprivation. In some embodiments, the environmental stress comprises depriving the cell of nitrogen, depriving the cell of sulfur, depriving the cell of metal, or any combination thereof. In some embodiments, the environmental stress comprises depriving the cell of nitrogen, depriving the cell of sulfur, depriving the cell of metal, or any combination thereof.

The present application further provides a method of increasing lipid production in a cell, comprising contacting the cell with an effective amount of a compound of Formula Ia:

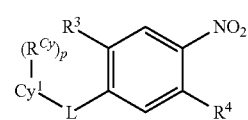

Ia or a pharmaceutically acceptable salt thereof, wherein:

L is selected from the group consisting of a bond, $C_{1-4}$ alkylene, $C_{1-4}$ hydroxyalkylene, $C_{1-4}$ alkyleneoxy, —($C_{1-4}$ alkylene)-$NR^L$—($C_{1-4}$ alylene)$_n$-, C(=O), and C(=O)NH;

$R^L$ is selected from the group consisting of H and methyl;

$R^3$ is H or $C_{1-4}$ alkoxy;

R$^4$ is selected from the group consisting of H and piperidinyl;

Cy$^1$ is selected from the group consisting of phenyl, C$_{3-8}$ cycloalkyl, 4-6 membered heterocycloalkyl, and 4-10 membered heteroaryl;

R$^{Cy}$ is selected from the group consisting of halo, C$_{1-4}$ alkyl, C$_{1-4}$ alkoxy, phenyl, —(C$_{1-4}$ alkylene)-(phenyl), C$_{3-10}$ cycloalkyl, and —(C$_{1-4}$ alkylene)-(C$_{3-10}$ cyloalkyl), wherein each phenyl and the phenyl group of —(C$_{1-4}$ alkylene)-(phenyl) is optionally substituted by 1 or 2 substituents independently selected from the group consisting of OH, halo, C$_{1-4}$ alkyl, and C$_{1-4}$ alkoxy;

n is 0 or 1; and p is 0, 1, 2, 3, 4, or 5; or a compound of Formula Ib:

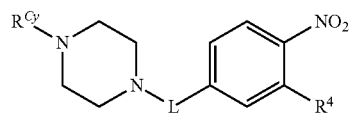

Ib or a pharmaceutically acceptable salt thereof, wherein:

L is selected from the group consisting of a bond, C$_{1-4}$ alkylene, C$_{1-4}$ hydroxyalkylene, and C(=O);

R$^4$ is selected from the group consisting of H and piperidinyl; and

R$^{Cy}$ is selected from the group consisting of C$_{1-4}$ alkyl, phenyl, —(C$_{1-4}$ alkylene)-(phenyl), C$_{3-10}$ cycloalkyl, and —(C$_{1-4}$ alkylene)-(C$_{3-10}$ cyloalkyl), wherein each phenyl and the phenyl group of —(C$_{1-4}$ alkylene)-(phenyl) is optionally substituted by 1 or 2 substituents independently selected from the group consisting of OH, halo, C$_{1-4}$ alkyl, and C$_{1-4}$ alkoxy; or a compound of Formula Ic:

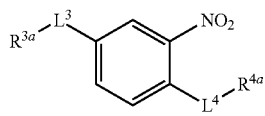

Ic or a pharmaceutically acceptable salt thereof, wherein:

L$^3$ is selected from the group consisting of a bond and C(O)NH;

R$^{3a}$ is selected from the group consisting of H, C$_{1-4}$ alkyl, C$_{1-4}$ alkoxy, -phenyl-(C$_{1-4}$ alkylene)-R$^b$, -(phenyl)-SO$_2$R$^b$, and 5-6 membered heteroaryl, wherein the 5-6 membered heteroaryl is optionally substituted with a C$_{1-4}$ alkyl group;

R$^b$ is selected from the group consisting of 5-6 membered heteroaryl and 5-6 membered heterocycloalkyl, wherein the 5-6 membered heterocycloalkyl is optionally substituted by a C$_{1-4}$ alkyl group;

L$^4$ is selected from the group consisting of a bond, S, C(=O)NH, C$_{1-6}$ alkyleneoxy, and SO$_2$-Cy$^2$-Cy$^3$;

Cy$^2$ and Cy$^3$ are each an independently selected 5-6 membered heterocycloalkyl group; and R$^{4a}$ is selected from the group consisting of H, C$_{1-4}$ alkyl, —(C$_{1-4}$ alkylene)-(C$_{3-6}$ cycloalkyl), 5-6 membered heterocyloalkyl, and —(C$_{1-4}$ alkylene)-(phenyl); or a compound of Formula IIa:

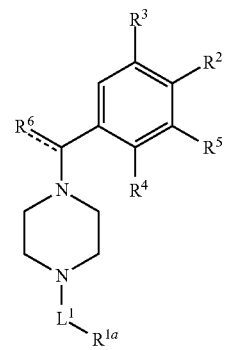

IIa or a pharmaceutically acceptable salt thereof, wherein:

L$^1$ is selected from the group consisting of a bond, C$_{1-4}$ alkylene, C$_{2-4}$ alkenylene, C$_{1-4}$ hydroxyalkylene, C$_{1-4}$ alkyleneoxy, 4-6 membered heterocycloalkylene, and C(=O), wherein the C$_{1-4}$ alkyleneoxy is optionally further substituted by one OH group;

R$^{1a}$ is selected from the group consisting of OH, C$_{1-4}$ alkyl, C$_{5-10}$ cycloalkyl, 8-10 membered heteroaryl, phenyl, —(C$_{1-4}$ alkylene)-(phenyl), and 10-13 membered heteroaryl, wherein the C$_{5-10}$ cycloalkyl, phenyl, and the phenyl group of the —(C$_{1-4}$ alkylene)-(phenyl) are each optionally substituted by 1, 2, or 3 substituents independently selected from the group consisting of halo, OH, NO$_2$, C$_{1-4}$ alkyl, and C$_{1-4}$ alkoxy, and wherein the 10-13 membered heteroaryl is optionally substituted by one halo group;

R$^2$ is selected from the group consisting of H, halo, OH, NO$_2$, C$_{1-4}$ alkyl, C$_{1-4}$ alkoxy, and —(C$_{1-4}$ alkylene)-(8-10 membered heteroaryl);

R$^3$ is selected from the group consisting of H, halo, C$_{1-4}$ alkoxy, and phenoxy; or alternatively, R$^2$ and R$^3$ come together, in combination with the carbon atoms to which they are attached, to form a 5-6 membered heterocycloalkyl or a C$_{6-10}$ aryl;

R$^4$ is selected from the group consisting of H, OH, and C$_{1-4}$ alkoxy;

R$^5$ is selected from the group consisting of H, halo, C$_{1-4}$ alkoxy, and phenoxy; and R$^6$ is selected from the group consisting of H and oxo; or a compound of Formula IIIa:

IIIa or a pharmaceutically acceptable salt thereof, wherein:

L$^1$ is selected from the group consisting of a bond, NH, N(C$_{1-4}$ alkyl), C$_{2-4}$ alkynyl, NHC(=O)(C$_{1-4}$ thioalkyl), C$_{1-6}$ alkyleneoxy, 5-6 membered heterocycloalkyl, NHC(=O) C$_{1-4}$ alkylene, and (C$_{1-4}$ alkylene)-NHC(=O)—(C$_{1-4}$ alkylene)-, wherein the C$_{1-6}$ alkyleneoxy is further optionally substituted by one OH group;

$R^{1a}$ is selected from the group consisting of H, $C_{1-4}$ alkyl, $C_{2-4}$ alkenyl, $C_{1-4}$ cyanoalkylene, 5-6 membered heterocycloalkyl, 5-6 membered heteroaryl, NH($C_{1-4}$ alkyl), and NH($C_{2-4}$ alkenyl), wherein the $C_{1-4}$ alkyl and $C_{2-4}$ alkenyl are each optionally substituted by one substituent selected from the group consisting of phenyl and hydroxyphenyl, and wherein the 5-6 membered heterocycloalkyl and 5-6 membered heteroaryl are each optionally substituted by 1 or 2 substituents independently selected from the group consisting of $C_{1-4}$ alkyl, $NH_2$ and di-halo substituted phenyl;

$L^2$ is selected from the group consisting of a bond and 5-6 membered heterocycloalkyl; and $R^{2a}$ is selected from the group consisting of H, $C_{1-4}$ hydroxyalkyl, $-SO_2(C_{1-4}$ alkyl).

In some embodiments, the cell is a eukaryotic cell or a cyanobacteria. In some embodiments, the cell is selected from the group consisting of an algal cell, a *drosophila* cell, a yeast cell, or a fungus cell. In some embodiments, the cell is an algal cell. In some embodiments, the cell is selected from the group consisting of:

*Chlamydomonas reinhardtii;*
*Chlorella sorokiniana;*
*Tetrachlorella alterans;*
*C. protothecoides;*
*C. vulgaris;* and
*Nannochloropsis* sp.

In some embodiments, the increasing lipid production comprises increasing fatty acid production. In some embodiments, the increasing lipid production comprises increasing polyunsaturated fatty acid production. In some embodiments, the increasing lipid production comprises increasing triacylglycerol production. In some embodiments, the increasing lipid production comprises increasing fatty acid production and increasing triacylglycerol production. In some embodiments, the increasing lipid production comprises increasing polyunsaturated fatty acid production and increasing triacylglycerol production.

In some embodiments, the method further comprises increasing carbohydrate accumulation in the cell. In some embodiments, the method further comprises increasing carbohydrate production in the cell.

In some embodiments, the lipid production is increased by greater than about 1.5 fold as compared to a cell that has not been contacted by the compound. In some embodiments, the lipid production is increased by greater than about 2 fold as compared to a cell that has not been contacted by the compound. In some embodiments, the lipid production is increased by greater than about 2.5 fold as compared to a cell that has not been contacted by the compound.

In some embodiments, the contacting the cell with the compound does not reduce the rate of cellular growth compared to a cell that has not been contacted by the compound. In some embodiments, contacting the cell with the compound does not reduce the rate of photosynthesis of the cell compared to a cell that has not been contacted by the compound. In some embodiments, the contacting does not adversely affect the viability of the cell.

In some embodiments, the lipid production is increased without exposing the cell to environmental stress. In some embodiments, the environmental stress comprises nutrient deprivation. In some embodiments, the environmental stress comprises depriving the cell of nitrogen, depriving the cell of sulfur, depriving the cell of metal, or any combination thereof. In some embodiments, the environmental stress comprises depriving the cell of nitrogen, depriving the cell of sulfur, depriving the cell of metal, or any combination thereof.

The present application further provides a method of increasing lipid accumulation in a cell, comprising contacting the cell with an effective amount of a compound selected from the group of compounds provided in Table 1A, Table 1B, Table 1C, Table 2A, Table 3A, Table 4, Table 5, and Table 6, or a pharmaceutically acceptable salt thereof.

The present application further provides a method of increasing lipid production in a cell, comprising contacting the cell with an effective amount of a compound selected from the group provided in Table 1A, Table 1B, Table 1C, Table 2A, Table 3A, Table 4, Table 5, and Table 6, or a pharmaceutically acceptable salt thereof.

The present application further provides a method of increasing lipid accumulation in a cell, comprising contacting the cell with an effective amount of a compound selected from the group provided in Table 4, Table 5, and Table 6, or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile hydrochloride).

In some embodiments, the cell is a eukaryotic cell or a cyanobacteria. In some embodiments, the cell is selected from the group consisting of an algal cell, a *drosophila* cell, a yeast cell, or a fungus cell. In some embodiments, the cell is an algal cell. In some embodiments, the cell is selected from the group consisting of:

*Chlamydomonas reinhardtii;*
*Chlorella sorokiniana;*
*Tetrachlorella alterans;*
*C. protothecoides;*
*C. vulgaris;* and
*Nannochloropsis* sp.

In some embodiments, the increasing lipid accumulation comprises increasing fatty acid accumulation. In some embodiments, the increasing lipid accumulation comprises increasing polyunsaturated fatty acid accumulation. In some embodiments, the increasing lipid accumulation comprises increasing triacylglycerol accumulation. In some embodiments, the increasing lipid accumulation comprises increasing fatty acid accumulation and increasing triacylglycerol accumulation. In some embodiments, the increasing lipid accumulation comprises increasing polyunsaturated fatty acid accumulation and increasing triacylglycerol accumulation.

In some embodiments, the method further comprises increasing carbohydrate accumulation in the cell. In some embodiments, the method further comprises increasing carbohydrate production in the cell.

In some embodiments, the lipid accumulation is increased by greater than about 1.5 fold as compared to a cell that has not been contacted by the compound. In some embodiments, the lipid accumulation is increased by greater than about 2 fold as compared to a cell that has not been contacted by the compound. In some embodiments, the lipid accumulation is increased by greater than about 2.5 fold as compared to a cell that has not been contacted by the compound.

In some embodiments, the contacting the cell with the compound does not reduce the rate of cellular growth compared to a cell that has not been contacted by the compound.

In some embodiments, contacting the cell with the compound does not reduce the rate of photosynthesis of the cell compared to a cell that has not been contacted by the compound. In some embodiments, the contacting does not adversely affect the viability of the cell. In some embodiments, the lipid accumulation is increased without exposing the cell to environmental stress. In some embodiments, the environmental stress comprises nutrient deprivation. In some embodiments, the environmental stress comprises depriving the cell of nitrogen, depriving the cell of sulfur, depriving the cell of metal, or any combination thereof.

The present application further provides a method of increasing lipid production in a cell, comprising contacting the cell with an effective amount of a compound selected from the group provided in Table 4, Table 5, and Table 6, or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile hydrochloride).

In some embodiments, the cell is a eukaryotic cell or a cyanobacteria. In some embodiments, the cell is selected from the group consisting of an algal cell, a *drosophila* cell, a yeast cell, or a fungus cell. In some embodiments, the cell is an algal cell. In some embodiments, the cell is selected from the group consisting of:
*Chlamydomonas reinhardtii;*
*Chlorella sorokiniana;*
*Tetrachlorella alterans;*
*C. protothecoides;*
*C. vulgaris;* and
*Nannochloropsis* sp.

In some embodiments, the increasing lipid production comprises increasing fatty acid production. In some embodiments, the increasing lipid production comprises increasing polyunsaturated fatty acid production. In some embodiments, the increasing lipid production comprises increasing triacylglycerol production. In some embodiments, the increasing lipid production comprises increasing fatty acid production and increasing triacylglycerol production. In some embodiments, the increasing lipid production comprises increasing polyunsaturated fatty acid production and increasing triacylglycerol production.

In some embodiments, the method further comprises increasing carbohydrate accumulation in the cell. In some embodiments, the method further comprises increasing carbohydrate production in the cell.

In some embodiments, the lipid production is increased by greater than about 1.5 fold as compared to a cell that has not been contacted by the compound. In some embodiments, the lipid production is increased by greater than about 2 fold as compared to a cell that has not been contacted by the compound. In some embodiments, the lipid production is increased by greater than about 2.5 fold as compared to a cell that has not been contacted by the compound.

In some embodiments, the contacting the cell with the compound does not reduce the rate of cellular growth compared to a cell that has not been contacted by the compound. In some embodiments, contacting the cell with the compound does not reduce the rate of photosynthesis of the cell compared to a cell that has not been contacted by the compound. In some embodiments, the contacting does not adversely affect the viability of the cell.

In some embodiments, the lipid production is increased without exposing the cell to environmental stress. In some embodiments, the environmental stress comprises nutrient deprivation. In some embodiments, the environmental stress comprises depriving the cell of nitrogen, depriving the cell of sulfur, depriving the cell of metal, or any combination thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 1 shows $EC_{50}$ (µM) values and microscopy images of compounds 1, 62, and 136 in *Chlamydomonas reinhardtii* cells.

DETAILED DESCRIPTION

Figure 2A:
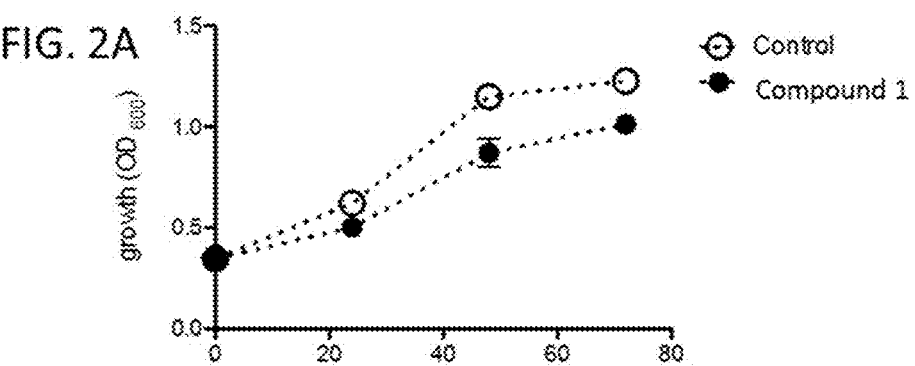
FIGS. 2A-2C show algal cell growth over a period of 72 hours in the presence of compound 1 (FIG. 2A), compound 62 (FIG. 2B), and compound 136 (FIG. 2C).

There are several advantages to employing algae for the production of biofuels, for example, high productivity due to rapid growth and the ability to accumulate lipid to 20-40% dry weight and potentially 100-fold more oil per acre than soybeans or other oil-seed bearing plants. However, at the present time algal oils are not ready for commercialization due to high costs in producing and processing sufficient biomass given the primitive state of knowledge of algal biology and biotechnology (see, e.g., Singh et al., *Bioresource Technology*, 2011, 102, 26-34 and Hannon et al., *Biofuels*, 2010, 1, 763-784).

Algae are a diverse group of microorganisms that include species that inhabit marine, freshwater and terrestrial niches. It is estimated that 30-50% of the net photosynthetic productivity on plant earth is contributed by phytoplankton including algae. Yet, our understanding of the biology, metabolism and genetics of any algal species is limited. Among the microalga, *Chlamydomonas reinhardtii*, is widely employed as a model organism. *Chlamydomonas* is capable of harnessing light and fixing $CO_2$ to produce structural and energy rich storage compounds, including carbohydrates, lipids, and proteins. Desirable characteristics for use of algae as a biofuel feedstock include: rapid growth rate, high lipid product content, tolerance to variable environmental conditions, such as poor water quality, high salinity, extremes of pH, resistance to pathogens, ability to compete for micronutrients, and ease of harvesting and extraction (see e.g., Hannon et al., *Biofuels*, 2010, 1, 763-784, Chisti, Y. *Biotechnology Advances*, 2007, 25, 294-306, and Deng et al., *Biomass and Bioenergy*, 2011, 35, 1811-1817). All of these factors may not be realized in one algal species but understanding the factors that enhance or limit, for example, biomass accumulation in a model organism such as *Chlamydomonas* will ultimately increase our ability to select and/or generate strains with enhanced traits useful for biofuel production.

Conditions currently employed to induce lipid accumulation in algae require an environmental stress, particularly nutrient deprivation of nitrogen, sulphur, or some metal (see, e.g., Deng et al., *Biomass and Bioenergy*, 2011, 35, 1811-1817; Garnier et al., *Journal of Proteomics*, 2014, 105, 107-120; and Msanne et al., *Phytochemistry*, 2012, 75, 50-59). Nutrient limitation may be achieved during normal growth when cultures reach saturation density. For example, nitrogen may become limiting at this time and triglyceride rich lipid droplets will become visible and measurable (see e.g, Msanne et al., *Phytochemistry*, 2012, 75, 50-59 and Wase et al., *Journal of Proteome Research*, 2014, 13, 1373-1396). However, this may be commensurate with cessation of protein synthesis, bleaching of the cultures as the chlorophylls are degraded, depletion of the photosynthetic enzymes such as RuBisCO, and turnover of membrane lipids, including thylakoid lipids (see, e.g., Wase et al., *Journal of Proteome Research*, 2014, 13, 1373-1396). What is desired are methods to activate metabolic pathways leading to storage of lipids without diversion of carbon and nitrogen away from other anabolic processes required for cell growth and division.

Accordingly, the present application provides methods of increasing lipid accumulation and production in cells (e.g., algal cells) using activators of lipid synthesis and storage provided herein.

Compounds

The present application provides compounds that are activators of lipid synthesis and lipid storage in cells. In some embodiments, the compound is a compound of Formula I:

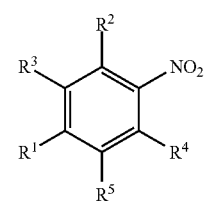

or a pharmaceutically acceptable salt thereof, wherein:

substituents $R^1$, $R^2$, $R^3$, $R^4$, and $R^5$ of Formula I are as defined herein.

In some embodiments, a compound of Formula I is substituted according to the substituents provided in Table 1. In some embodiments, each $R^1$, $R^2$, $R^3$, $R^4$, and $R^5$, unless specified otherwise in Table 1, is selected from the group consisting of H, OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkyl)-($C_{1-6}$ alkoxy), —($C_{1-6}$ alkoxy)-($C_{1-6}$ alkoxy), $C_{1-6}$ haloalkoxy, $C_{3-10}$ cycloalkyl, $C_{6-10}$ aryl, 5-10 membered heteroaryl, 4-10 membered heterocycloalkyl, amino, $C_{1-6}$ alkylamino, di($C_{1-6}$ alkyl)amino, carbamyl, $C_{1-6}$ alkylcarbamyl, di($C_{1-6}$ alkyl)carbamyl, carbamoyl, $C_{1-6}$ alkylcarbamoyl, di($C_{1-6}$ alkyl)carbamoyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino. In some embodiments, each $R^1$, $R^2$, $R^3$, $R^4$, $R^5$, $R^6$, and $R^7$, unless specified otherwise in Table 1, is H. In some embodiments, at least one of $R^1$, $R^2$, $R^3$, $R^4$, and $R^5$ is not H.

It is understood that the ∿∿∿ and ------ shown in the substituent groups provided in Tables 1-6 represent the point of attachment between the representative Formula (e.g., Formula I, Formula II, or Formula III) and the substituent group.

TABLE 1

Substituents of Formula I

TABLE 1-continued
Substituents of Formula I
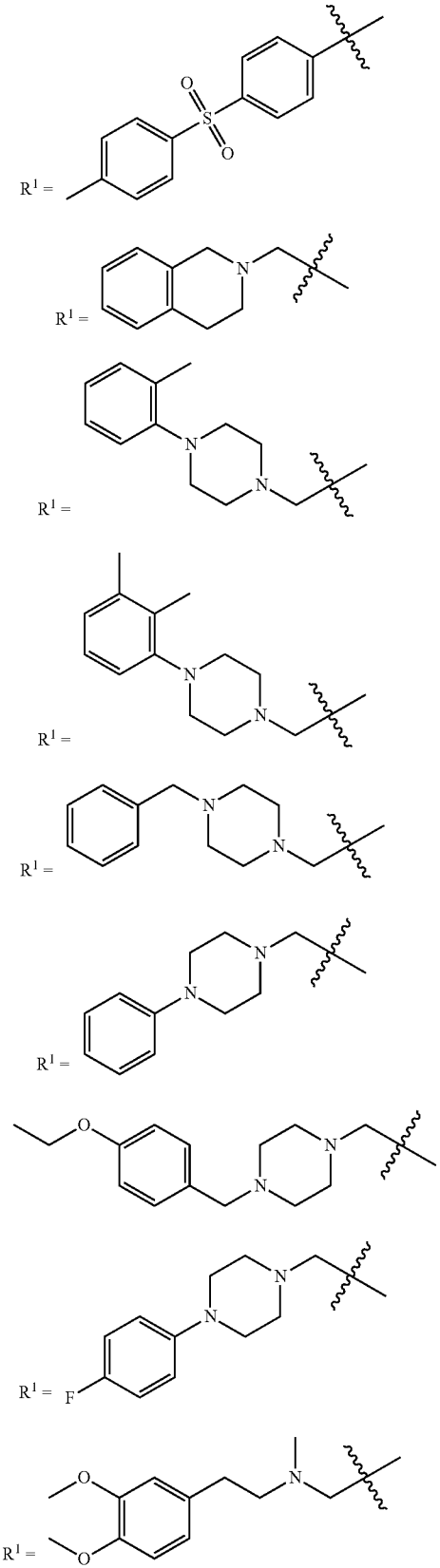
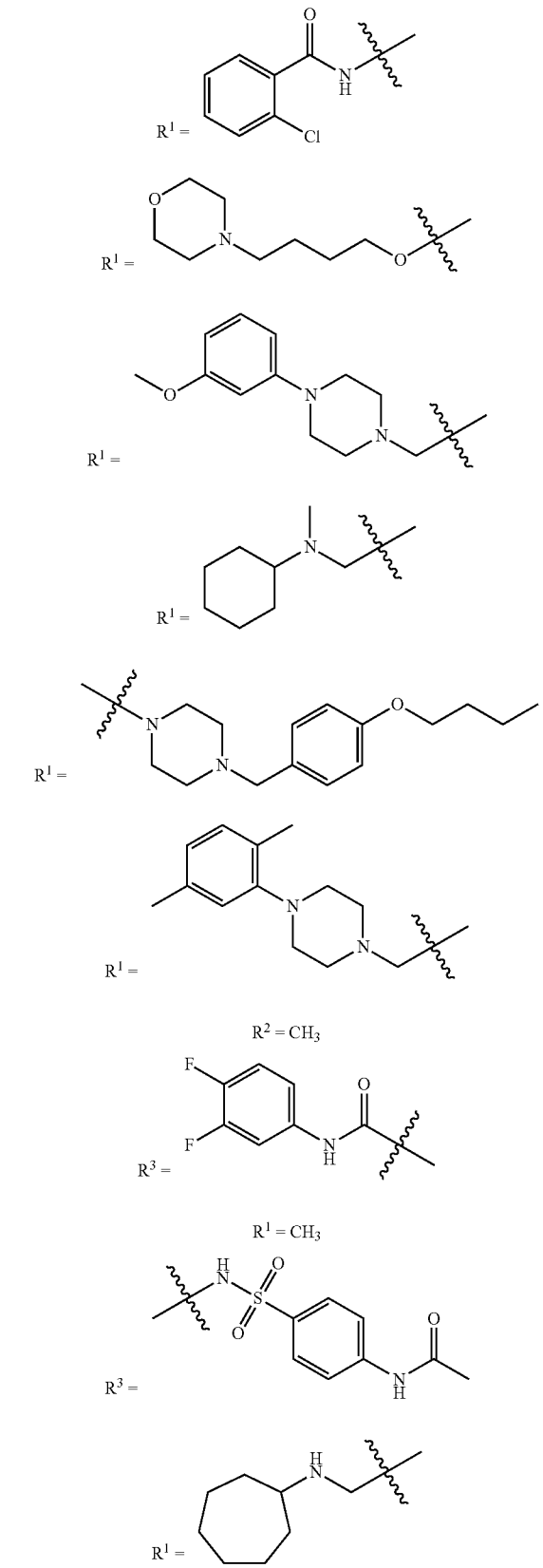

TABLE 1-continued
Substituents of Formula I
R¹ = 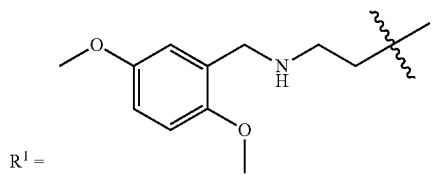 [SMILES: *CCNCc1cc(OC)ccc1OC]
R¹ = 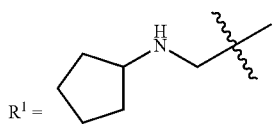 [SMILES: *CNC1CCCC1]
R³ = 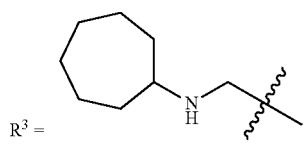 [SMILES: *CNC1CCCCCC1]
R¹ & R³ = 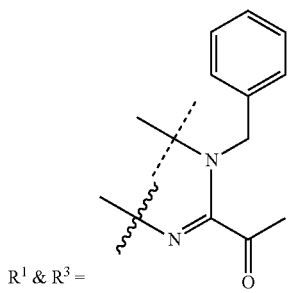
wherein:
----- refers to the bond connecting R¹ to Formula I; and
∿∿∿ refers to the bond connecting R³ to Formula I
R³ = 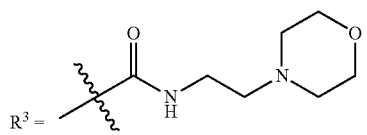
R⁴ = —OMe
R¹ = 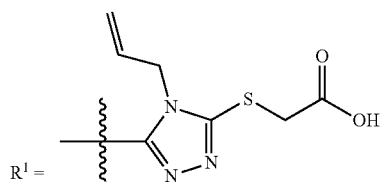 [SMILES: *c1nnc(SCC(=O)O)n1CC=C]
R¹ = 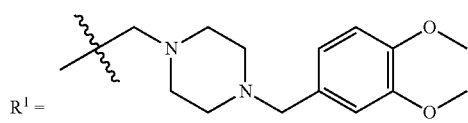 [SMILES: *CN1CCN(Cc2ccc(OC)c(OC)c2)CC1]
R¹ = 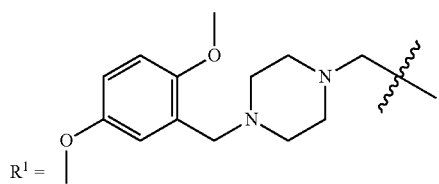 [SMILES: *CN1CCN(Cc2cc(OC)ccc2OC)CC1]
TABLE 1-continued
Substituents of Formula I
R¹ = 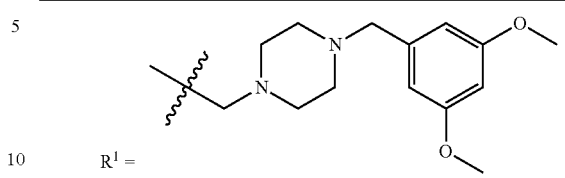
R¹ = 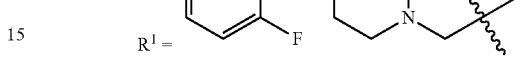
R¹ = 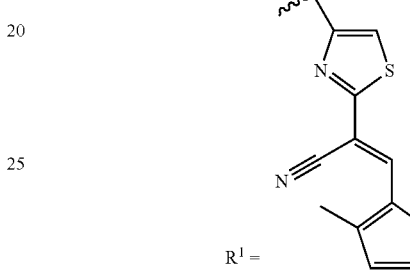
R¹ = 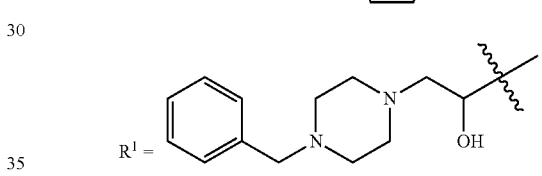
R¹ = 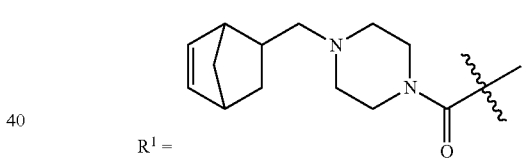
R¹ = 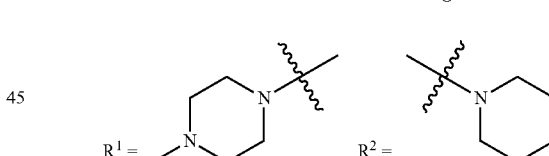   R² = 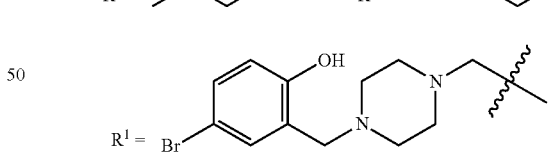
R¹ = 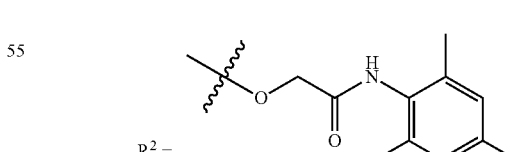
R² = 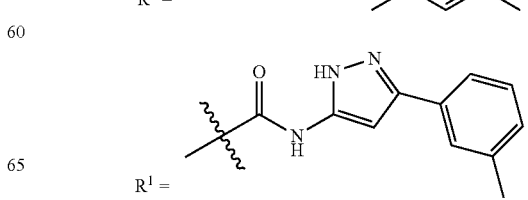
R¹ = 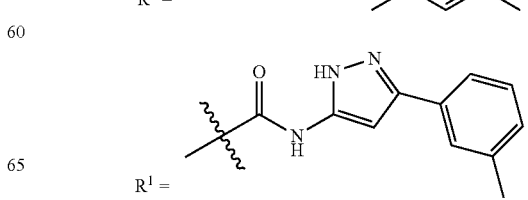

TABLE 1-continued
Substituents of Formula I
R¹ = 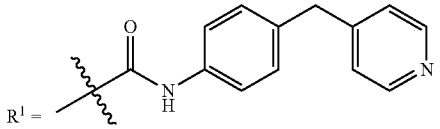
R⁵ = Cl
R¹ = 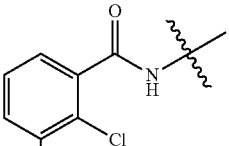
R² = 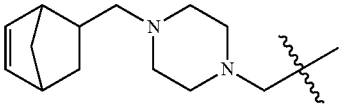
R¹ = 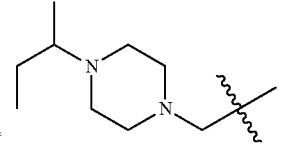
R¹ = 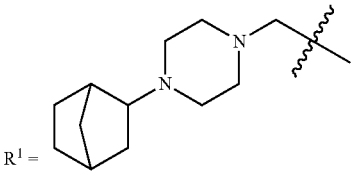 [SMILES: *CN1CCN(C2CC3CCC2C3)CC1]
R¹ = 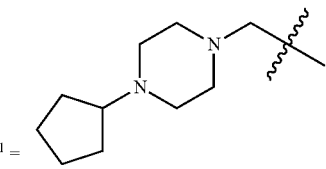
R¹ = 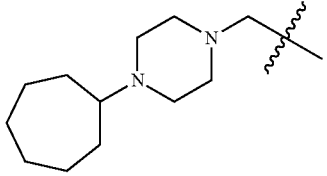
R² = 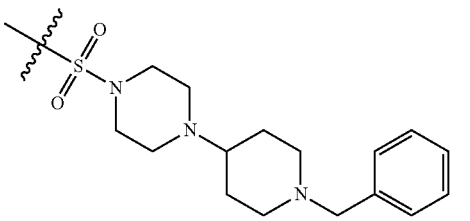
TABLE 1-continued
Substituents of Formula I
R² = 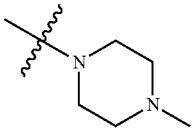
R⁵ = 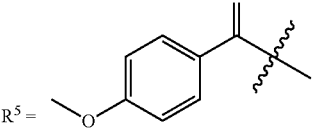
R³ = 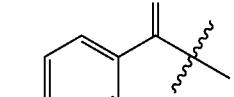
R⁴ = 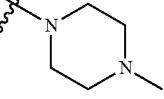
R² = CH₃
R³ = 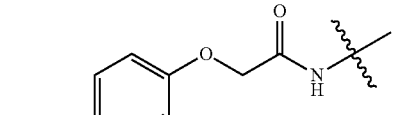
R⁵ = 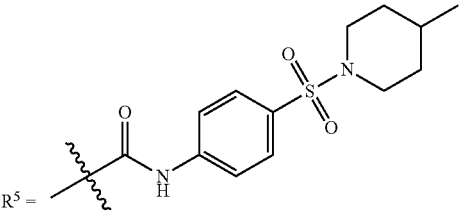 [SMILES: *C(=O)Nc1ccc(S(=O)(=O)N2CCC(C)CC2)cc1]
R² = 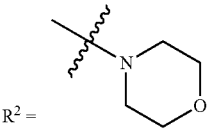
R⁵ = 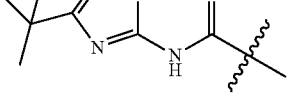
R³ = 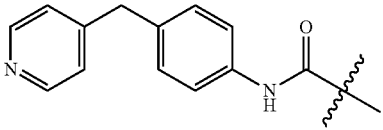
R⁴ = —SCH₂CH₃

TABLE 1-continued

Substituents of Formula I

R³ = —OCH₃
R⁴ = [3-cyclohexylpropanamide group]

R3 = —CH₃
R⁴ = [morpholine-ethyl-O-ethyl-O- group]

R¹ = [acetamido-benzamide-N-benzyl group]

R² = CH₃
R⁵ = [acetamido-benzamide-N-isopropyl group]

R² = CH₃
R³ = [acetamido-benzamide-N-benzyl group]

R¹ = [pentafluorobenzamide group]

R² = [2-ethylpiperidinyl carbonyl group]
R⁵ = Cl

R¹ = [tetrahydroisoquinoline-succinimide group]

R¹ = [2,3,4,5,6-pentafluorobenzamide group]

R₅ = —OCH₃

R² = [propanamide-N-(2,2,6,6-tetramethylpiperidin-4-yl) group]

R⁵ = [3,5-dichloro-4-ethoxybenzamide group]

The present application further provides a compound of Formula Ia:

$$\underset{\text{Ia}}{\begin{array}{c}(R^{Cy})_p \\ | \\ Cy^1-L\end{array}} \begin{array}{c}R^3 \\ \diagup \\ \diagdown \\ R^4\end{array} NO_2$$

or a pharmaceutically acceptable salt thereof, wherein:

L is selected from the group consisting of a bond, $C_{1-4}$ alkylene, $C_{1-4}$ hydroxyalkylene, $C_{1-4}$ alkyleneoxy, —($C_{1-4}$ alkylene)-NR$^L$—($C_{1-4}$ alkylene)$_n$-, C(=O), and C(=O)NH;

$R^L$ is selected from the group consisting of H and methyl;

$R^3$ is H or $C_{1-4}$ alkoxy;

$R^4$ is selected from the group consisting of H and piperidinyl;

$Cy^1$ is selected from the group consisting of phenyl, $C_{3-8}$ cycloalkyl, 4-6 membered heterocycloalkyl, and 4-10 membered heteroaryl;

$R^{Cy}$ is selected from the group consisting of halo, $C_{1-4}$ alkyl, $C_{1-4}$ alkoxy, phenyl, —($C_{1-4}$ alkylene)-(phenyl), $C_{3-10}$ cycloalkyl, and —($C_{1-4}$ alkylene)-($C_{3-10}$ cyloalkyl), wherein each phenyl and the phenyl group of —($C_{1-4}$ alkylene)-(phenyl) is optionally substituted by 1 or 2 substituents independently selected from the group consisting of OH, halo, $C_{1-4}$ alkyl, and $C_{1-4}$ alkoxy;

n is 0 or 1; and p is 0, 1, 2, 3, 4, or 5.

In some embodiments, L is selected from the group consisting of a bond, —CH$_2$—, —CH(OH)CH$_2$—, —CH$_2$CH$_2$NR$^L$CH$_2$—, —CH$_2$NR$^L$CH$_2$CH$_2$—, —OCH$_2$CH$_2$CH$_2$CH$_2$—, —CH$_2$NH—, C(=O), and C(=O)NH. In some embodiments, L is selected from the group consisting of a bond, —CH$_2$—, —CH(OH)CH$_2$—, —CH$_2$CH$_2$NHCH$_2$—, —CH$_2$N(CH$_3$)CH$_2$CH$_2$—, —OCH$_2$CH$_2$CH$_2$CH$_2$—, —CH$_2$NH—, C(=O), and C(=O)NH. In some embodiments, L is CH$_2$.

In some embodiments, $R^3$ is selected from the group consisting of H and methoxy. In some embodiments, $R^3$ is H. In some embodiments, $R^3$ is methoxy.

In some embodiments, $R^4$ is H. In some embodiments, $R^4$ is piperidinyl.

In some embodiments, $Cy^1$ is phenyl. In some embodiments, $Cy^1$ is $C_{3-8}$ cycloalkyl. In some embodiments, $Cy^1$ is $C_{5-8}$ cycloalkyl. In some embodiments, $Cy^1$ is a $C_{3-8}$ cycloalkyl selected from the group consisting of cyclopentyl, cyclohexyl, and cycloheptyl. In some embodiments, $Cy^1$ is a 4-6 membered heterocycloalkyl. In some embodiments, $Cy^1$ is a 4-6 membered heterocycloalkyl selected from the group consisting of piperazinyl, and morpholinyl. In some embodiments, $Cy^1$ is piperazinyl. In some embodiments, $Cy^1$ is a 4-10 membered heteroaryl. In some embodiments, $Cy^1$ is a 4-6 membered heteroaryl. In some embodiments, $Cy^1$ is an 8-10 membered heteroaryl. In some embodiments, $Cy^1$ is a 4-10 membered heteroaryl selected from the group consisting of:

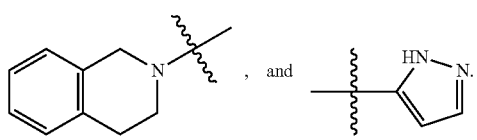 [SMILES: *N1CCc2ccccc2C1 ; *c1ccn[nH]1]

In some embodiments, $R^{Cy}$ is selected from the group consisting of halo, $C_{1-4}$ alkyl, $C_{1-4}$ alkoxy, phenyl, —CH$_2$-(phenyl), $C_{5-7}$ cycloalkyl, and —(CH$_2$)—($C_{5-7}$ cycloalkyl). In some embodiments, $R^{Cy}$ is selected from the group consisting of fluoro, methyl, 2-butyl, methoxy, phenyl, —CH$_2$-(phenyl), cyclopentyl, cycloheptyl,

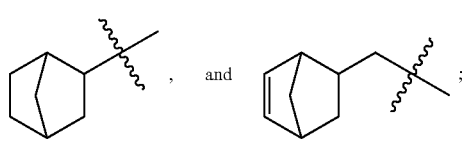 [SMILES: *C1CC2CCC1C2 ; *CC1CC2C=CC1C2]

wherein each phenyl and the phenyl group of —CH$_2$-(phenyl) is optionally substituted by 1 or 2 substituents independently selected from the group consisting of OH, halo, $C_{1-4}$ alkyl, and $C_{1-4}$ alkoxy. In some embodiments, each phenyl and the phenyl group of —CH$_2$-(phenyl) is optionally substituted by 1 or 2 substituents independently selected from the group consisting of OH, fluoro, bromo, methyl, methoxy, ethoxy, and butoxy.

In some embodiments, n is 0. In some embodiments, n is 1. In some embodiments, p is 1, 2, or 3. In some embodiments, p is 3, 4, or 5. In some embodiments, p is 1 or 2. In some embodiments, p is 1. In some embodiments, p is 2. In some embodiments, p is 3. In some embodiments, p is 4. In some embodiments, p is 5.

In some embodiments, the compound of Formula Ia is selected from the group of compounds provided in Table 1A.

TABLE 1A

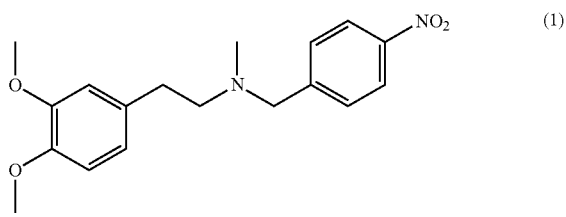 (1)

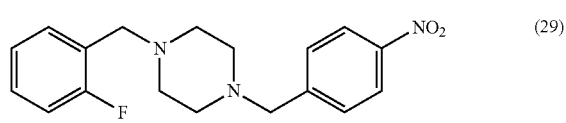 (29)

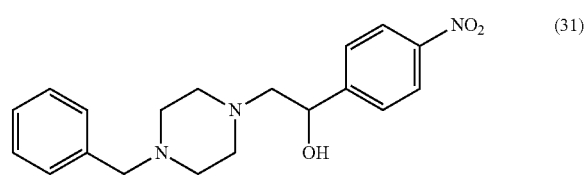 (31)

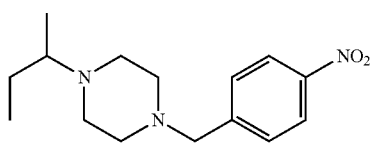 [SMILES: CCC(C)N1CCN(Cc2ccc([N+](=O)[O-])cc2)CC1] (40)

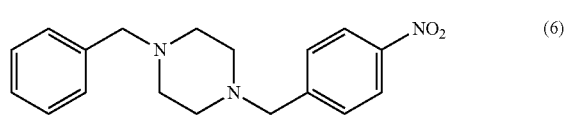 (6)

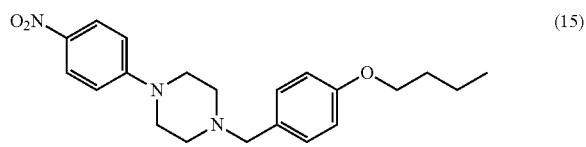 (15)

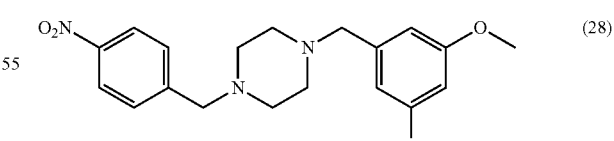 (28)

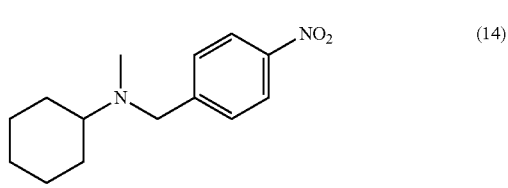 (14)

TABLE 1A-continued
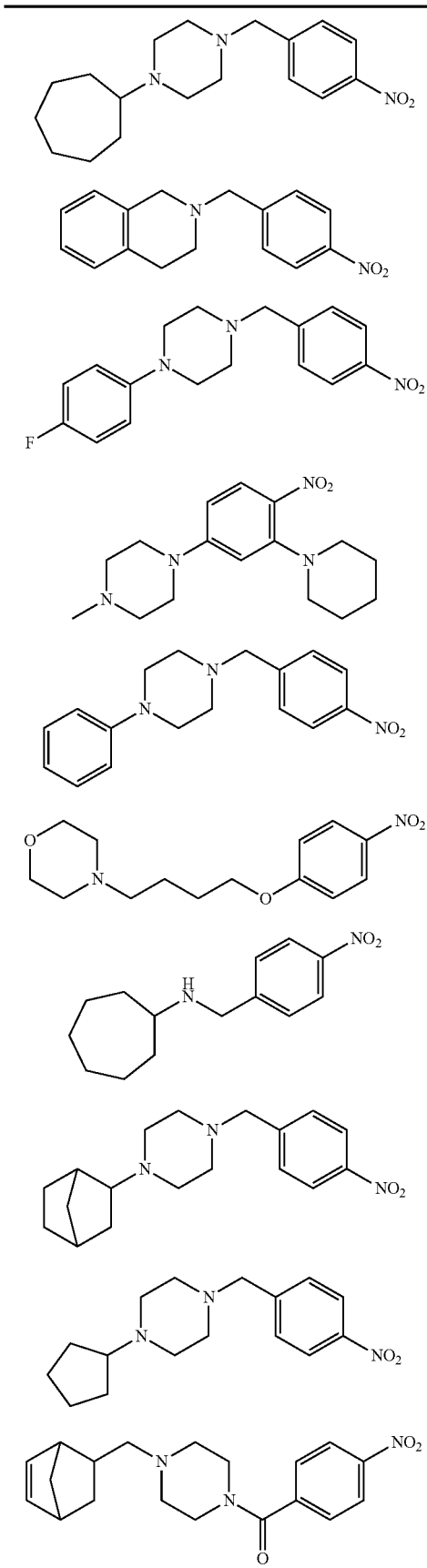
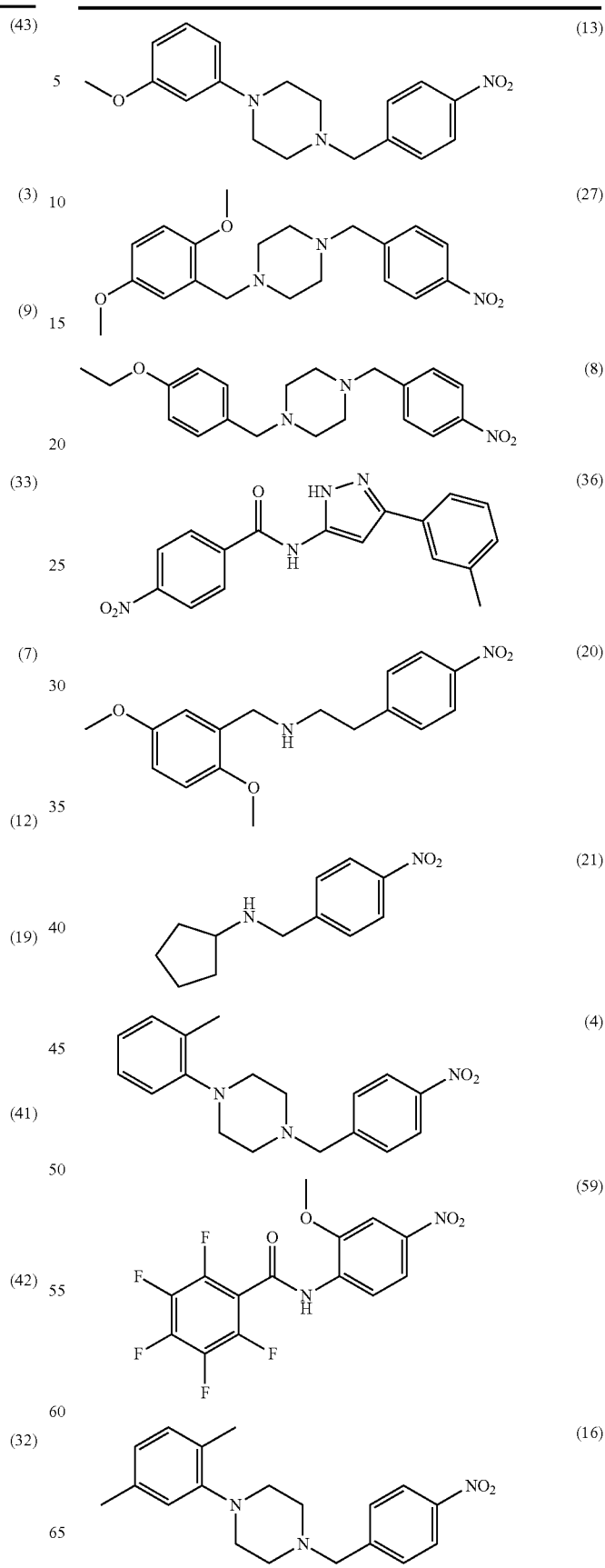

TABLE 1A-continued

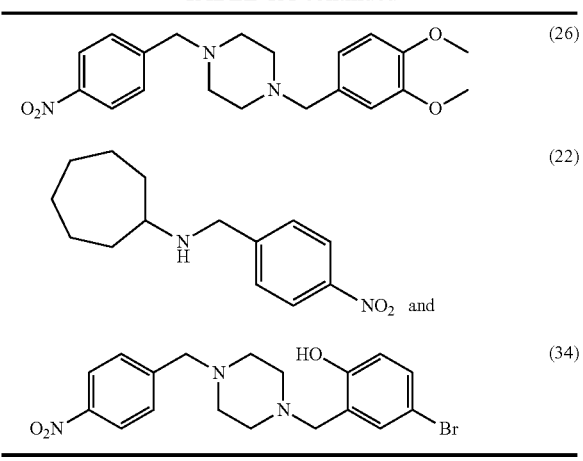

or a pharmaceutically acceptable salt thereof. In some embodiments, the pharmaceutically acceptable salt is a hydrochloride salt.

In some embodiments, provided herein is a compound of Formula Ib:

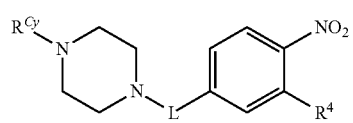

or a pharmaceutically acceptable salt thereof, wherein, L, $R^4$, and $R^{Cy}$ are as defined above for compounds of Formula Ia.

In some embodiments, the compound is a compound of Formula Ib, or a pharmaceutically acceptable salt thereof, wherein:

L is selected from the group consisting of a bond, $C_{1-4}$ alkylene, $C_{1-4}$ hydroxyalkylene, and C(=O);

$R^4$ is selected from the group consisting of H and piperidinyl; and $R^{Cy}$ is selected from the group consisting of $C_{1-4}$ alkyl, phenyl, —($C_{1-4}$ alkylene)-(phenyl), $C_{3-10}$ cycloalkyl, and —($C_{1-4}$ alkylene)-($C_{3-10}$ cyloalkyl), wherein each phenyl and the phenyl group of —($C_{1-4}$ alkylene)-(phenyl) is optionally substituted by 1 or 2 substituents independently selected from the group consisting of OH, halo, $C_{1-4}$ alkyl, and $C_{1-4}$ alkoxy.

In some embodiments, L is a bond. In some embodiments, L is $CH_2$. In some embodiments, L is C(=O). In some embodiments, L is CH(OH)CH$_2$.

In some embodiments, $R^4$ is H. In some embodiments, $R^4$ is piperidinyl.

In some embodiments, $R^{Cy}$ is selected from the group consisting of $C_{1-4}$ alkyl, phenyl, —CH$_2$-(phenyl), $C_{5-7}$ cycloalkyl, and —(CH$_2$)—($C_{5-7}$ cycloalkyl), wherein each phenyl and the phenyl group of —CH$_2$-(phenyl) is optionally substituted by 1 or 2 substituents independently selected from the group consisting of OH, halo, $C_{1-4}$ alkyl, and $C_{1-4}$ alkoxy. In some embodiments, $R^{Cy}$ is selected from the group consisting of methyl, 2-butyl, phenyl, —CH$_2$-(phenyl), cyclopentyl, cycloheptyl,

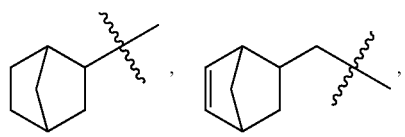 [SMILES: *C1CC2CCC1C2 ; *CC1CC2C=CC1C2]

wherein each phenyl and the phenyl group of —CH$_2$-(phenyl) is optionally substituted by 1 or 2 substituents independently selected from the group consisting of OH, halo, $C_{1-4}$ alkyl, and $C_{1-4}$ alkoxy. In some embodiments, each phenyl and the phenyl group of —CH$_2$-(phenyl) is optionally substituted by 1 or 2 substituents independently selected from the group consisting of OH, fluoro, bromo, methyl, methoxy, ethoxy, and butoxy.

In some embodiments, the compound of Formula Ib is selected from the group of compounds provided in Table 1B.

TABLE 1B

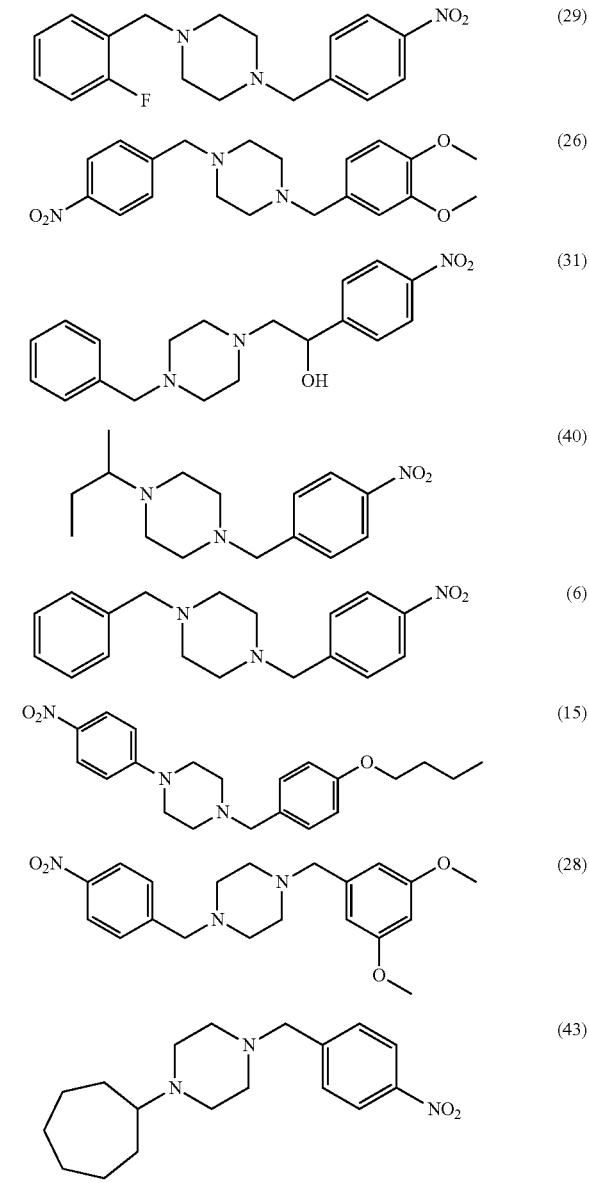

TABLE 1B-continued

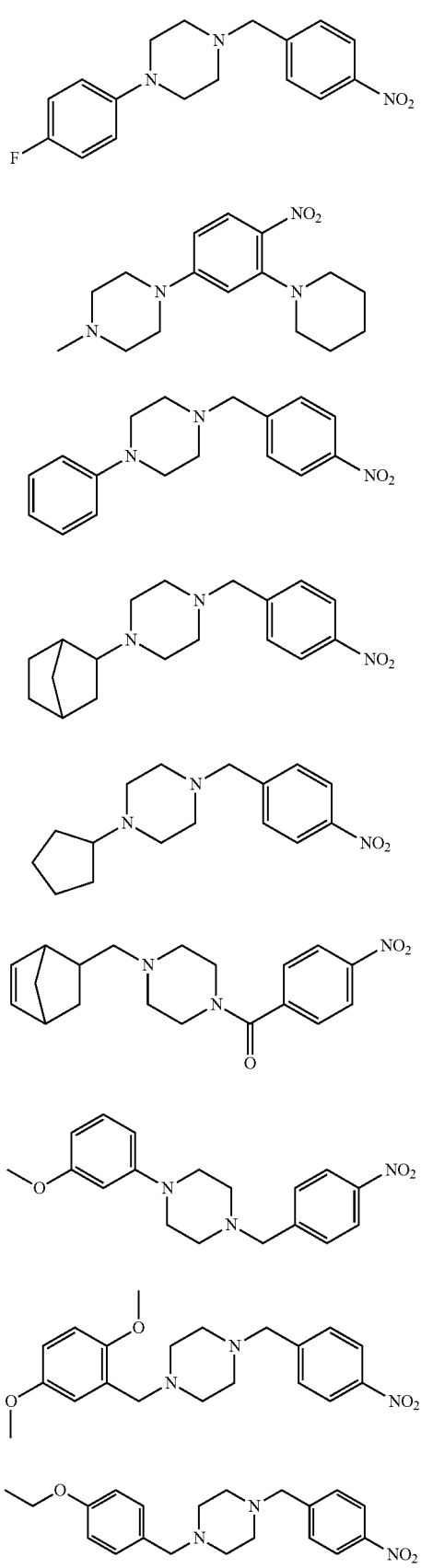

(9)

(33)

(7)

(41)

(42)

(32)

(13)

(27)

(8)

TABLE 1B-continued

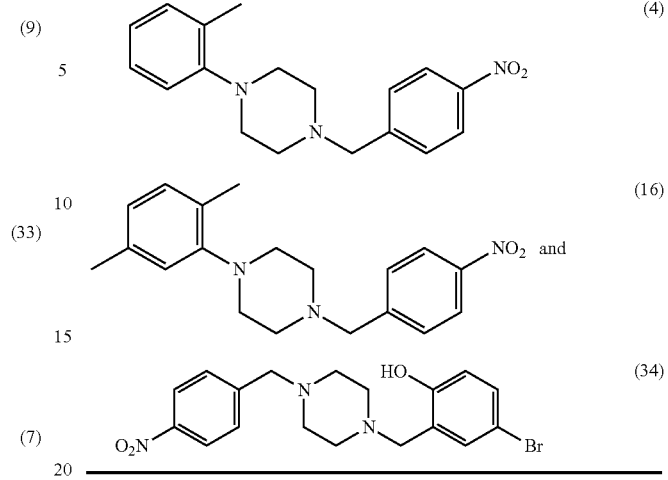

(4)

(16)

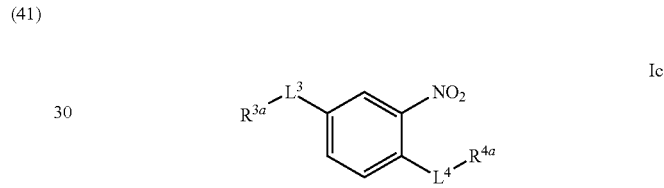

(34)

or a pharmaceutically acceptable salt thereof. In some embodiments, the pharmaceutically acceptable salt is a hydrochloride salt.

The present application further provides a compound of Formula Ic:

$$R^{3a}-L^3 \underset{L^4-R^{4a}}{\overset{NO_2}{\bigoplus}}$$

Ic or a pharmaceutically acceptable salt thereof, wherein:

$L^3$ is selected from the group consisting of a bond and C(O)NH;

$R^{3a}$ is selected from the group consisting of H, $C_{1-4}$ alkyl, $C_{1-4}$ alkoxy, -phenyl-($C_{1-4}$ alkylene)-$R^b$, -(phenyl)-$SO_2R^b$, and 5-6 membered heteroaryl, wherein the 5-6 membered heteroaryl is optionally substituted with a $C_{1-4}$ alkyl group;

$R^b$ is selected from the group consisting of 5-6 membered heteroaryl and 5-6 membered heterocycloalkyl, wherein the 5-6 membered heterocycloalkyl is optionally substituted by a $C_{1-4}$ alkyl group;

$L^4$ is selected from the group consisting of a bond, S, C(=O)NH, $C_{1-6}$ alkyleneoxy, and $SO_2$-$Cy^2$-$Cy^3$;

$Cy^2$ and $Cy^3$ are each an independently selected 5-6 membered heterocycloalkyl group; and $R^{4a}$ is selected from the group consisting of H, $C_{1-4}$ alkyl, —($C_{1-4}$ alkylene)-($C_{3-6}$ cycloalkyl), 5-6 membered heterocyloalkyl, and —($C_{1-4}$ alkylene)-(phenyl).

In some embodiments, $L^3$ is a bond. In some embodiments, $L^3$ is C(O)NH.

In some embodiments, $R^{3a}$ is H. In some embodiments, $L^3$ is a bond and $R^{3a}$ is H. In some embodiments, $R^{3a}$ is $C_{1-4}$ alkoxy. In some embodiments, $R^{3a}$ is methoxy. In some embodiments, $L^3$ is a bond and $R^{3a}$ is methoxy. In some embodiments, $R^{3a}$ is -phenyl-($C_{1-4}$ alkylene)-$R^b$. In some embodiments, $R^{3a}$ is -phenyl-($CH_2$)—$R^b$. In some embodiments, $R^{3a}$ is -(phenyl)-$SO_2R^b$. In some embodiments, $R^b$ is selected from the group consisting of 5-6 membered heteroaryl and 5-6 membered heterocycloalkyl substituted by a $C_{1-4}$ alkyl group. In some embodiments, $R^b$ is selected from the group consisting of pyridyl and 4-methylpiperidinyl. In some embodiments, $R^{3a}$ is a 5-6 membered heteroaryl substituted with a $C_{1-4}$ alkyl group. In some embodiments, $R^{3a}$ is 4-tert-butylthiazolyl.

In some embodiments, $L^4$ is selected from the group consisting of a bond, S, C(=O)NH, —OCH₂CH₂OCH₂CH₂—, and SO₂-Cy²-Cy³. In some embodiments, $L^4$ is a bond. In some embodiments, $L^4$ is S. In some embodiments, $L^4$ is C(=O)NH. In some embodiments, $L^4$ is $C_{1-6}$ alkyleneoxy. In some embodiments, $L^4$ is —OCH₂CH₂OCH₂CH₂—. In some embodiments, $L^4$ is SO₂-Cy²-Cy³. In some embodiments, Cy² is a 6-membered heterocycloalkyl group comprising two ring heteroatoms which are nitrogen. In some embodiments, Cy² is piperazinyl. In some embodiments, Cy³ is a 6-membered heterocycloalkyl group comprising one ring heteroatom which is nitrogen. In some embodiments, Cy³ is piperidinyl.

In some embodiments, $R^{4a}$ is H. In some embodiments, $L^4$ is a bond and $R^{4a}$ is H. In some embodiments, $R^{4a}$ is $C_{1-4}$ alkyl. In some embodiments, $R^4$ is methyl. In some embodiments, $L^4$ is a bond and $R^{4a}$ is methyl. In some embodiments, $R^{4a}$ is —($C_{1-4}$ alkylene)-($C_{3-6}$ cycloalkyl). In some embodiments, $R^{4a}$ is —(CH₂CH₂)—($C_{5-6}$ cycloalkyl). In some embodiments, $R^{4a}$ is —(CH₂CH₂)-(cyclohexyl). In some embodiments, $R^{4a}$ is a 5-6 membered heterocyloalkyl group comprising one ring heteroatom which is nitrogen and one ring heteroatom which is oxygen. In some embodiments, $R^{4a}$ is morpholinyl. In some embodiments, $R^{4a}$ is —($C_{1-4}$ alkylene)-(phenyl). In some embodiments, $R^{4a}$ is —(CH₂)-(phenyl).

In some embodiments, the compound of Formula Ic is selected from the group of compounds provided in Table 1C.

TABLE 1C

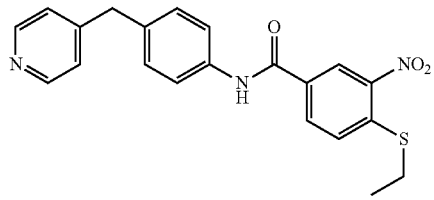 [SMILES: CCSc1ccc(C(=O)Nc2ccc(Cc3ccncc3)cc2)cc1[N+](=O)[O-]]
(50)

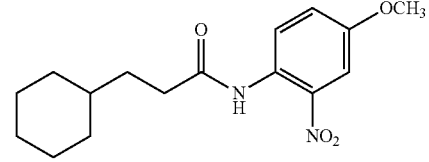 [SMILES: COc1ccc(NC(=O)CCC2CCCCC2)c([N+](=O)[O-])c1]
(51)

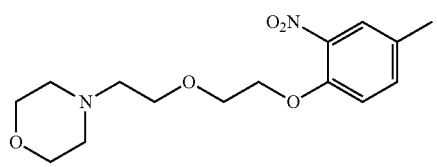 [SMILES: Cc1ccc(OCCOCCN2CCOCC2)c([N+](=O)[O-])c1]
(52)

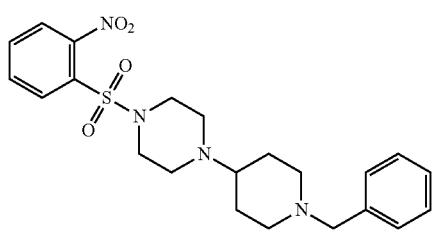 [SMILES: O=[N+]([O-])c1ccccc1S(=O)(=O)N1CCN(C2CCN(Cc3ccccc3)CC2)CC1]
(44)

TABLE 1C-continued

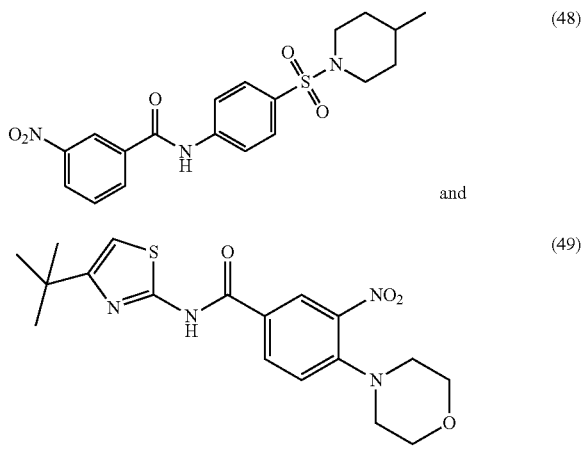
(48)

and (49)

or a pharmaceutically acceptable salt thereof. In some embodiments, the pharmaceutically acceptable salt is a hydrochloride salt.

The present application further provides a compound of Formula II:

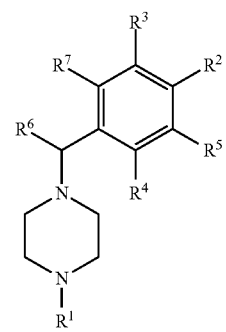
II or a pharmaceutically acceptable salt thereof, wherein substituents $R^1$, $R^2$, $R^3$, $R^4$, $R^5$, $R^6$, and $R^7$ of Formula II are as defined herein.

In some embodiments, each $R^1$, $R^2$, $R^3$, $R^4$, $R^5$, $R^6$, and $R^7$, unless specified otherwise in Table 2, is selected from the group consisting of H, OH, SH, CN, NO₂, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkyl)-($C_{1-6}$ alkoxy), —($C_{1-6}$ alkoxy)-($C_{1-6}$ alkoxy), $C_{1-6}$ haloalkoxy, $C_{3-10}$ cycloalkyl, $C_{6-10}$ aryl, 5-10 membered heteroaryl, 4-10 membered heterocycloalkyl, amino, $C_{1-6}$ alkylamino, di($C_{1-6}$ alkyl)amino, carbamyl, $C_{1-6}$ alkylcarbamyl, di($C_{1-6}$ alkyl)carbamyl, carbamoyl, $C_{1-6}$ alkylcarbamoyl, di($C_{1-6}$ alkyl)carbamoyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino. In some embodiments, each $R^1$, $R^2$, $R^3$, $R^4$, $R^5$, $R^6$, and $R^7$, unless specified otherwise in Table 2, is H. In some embodiments, at least one of $R^1$, $R^2$, $R^3$, $R^4$, $R^5$, $R^6$, and $R^7$, is not H.

TABLE 2
Substituents of Formula II
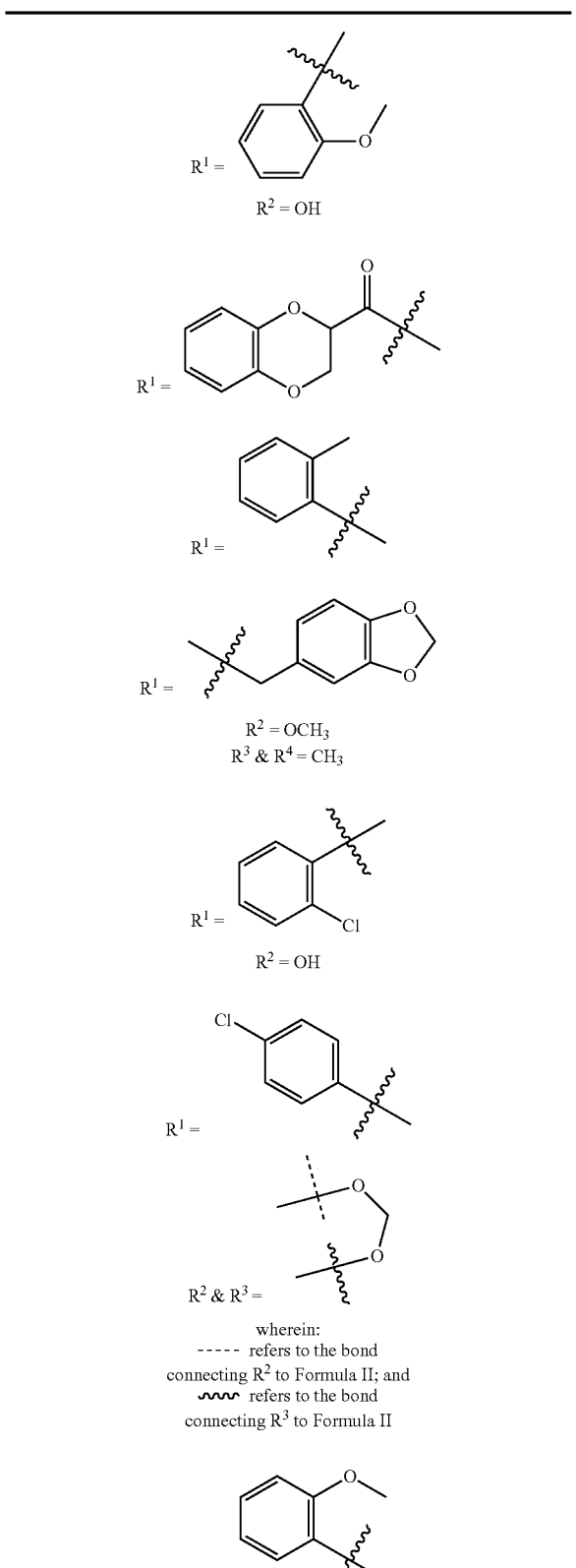
TABLE 2-continued
Substituents of Formula II
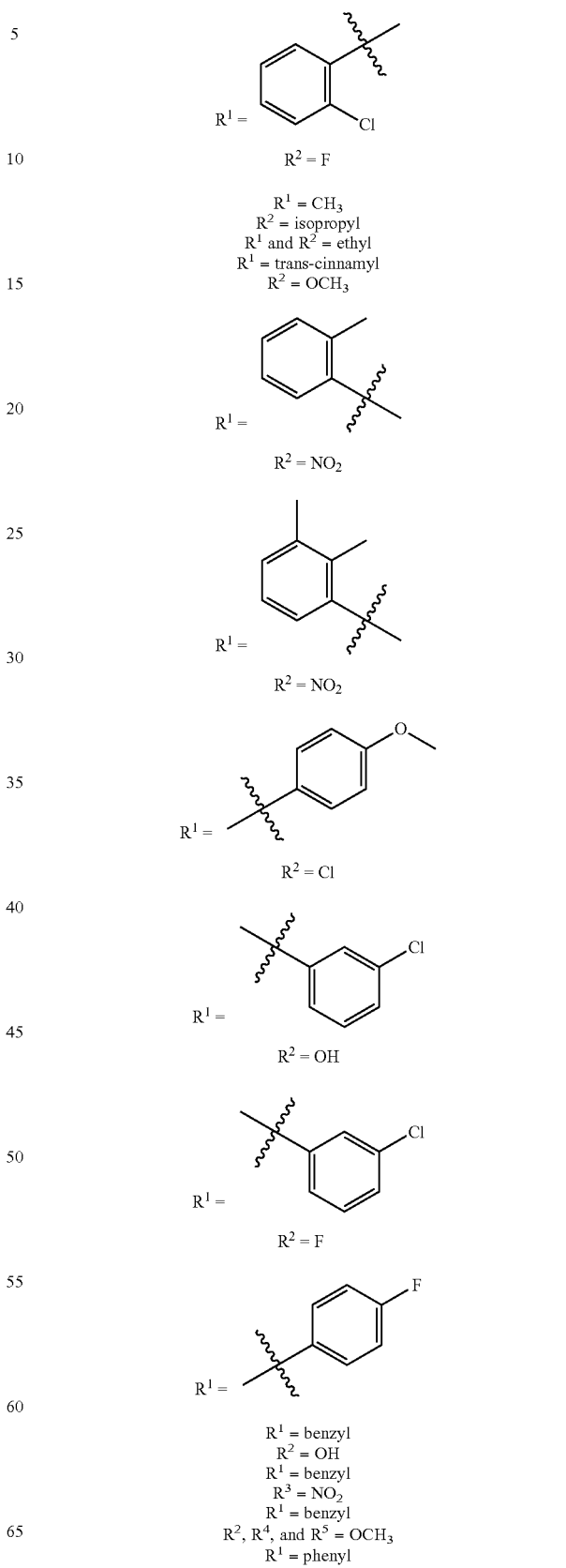

TABLE 2-continued

Substituents of Formula II

R² = OH

R¹ = CH₃

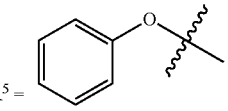
R⁵ =

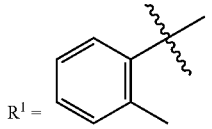
R¹ =

R² = ethyl

R¹ = phenyl
R² = NO₂
R¹ = phenyl
R² = Br
R¹ = p-nitrophenyl
R² = —OCH₂CH₃

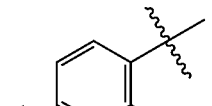
R¹ =

R² = —OCH₂CH₃

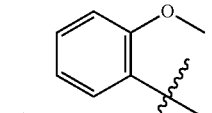
R¹ =

R² = OH

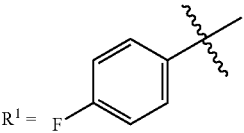
R¹ = F

R² = CH₃

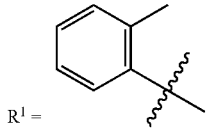
R¹ =

R² = F

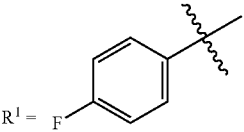
R¹ = F

R² = NO₂

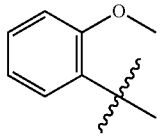
R¹ =

R² = CH₃

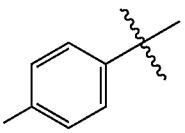
R¹ = F

R² = —OCH₂CH₃

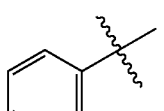
R¹ =

R² = —OCH₂CH₃

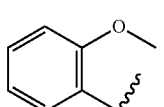
R¹ =

R² = F

R¹ = —CH₂CH₂OH
R² = isopropyl
R¹ = —CH₂CH₂OH
R² = ethyl
R¹ = benzyl
R³ & R⁵ = OCH₃
R¹ = —CH₂CH₂OH
R² = CH₃

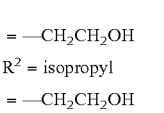
R¹ =

R², R³, and R⁵ = —OCH₃

R⁶ = (═O)

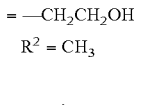
R¹ =

R² = NO₂

TABLE 2-continued

Substituents of Formula II

R¹ = CH₃

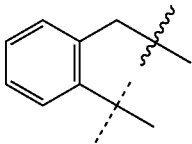

R² & R³ = wherein:
----- refers to the bond connecting R² to Formula II; and
∿∿∿ refers to the bond connecting R³ to Formula II R¹ = ethyl
R² = —N(ethyl)₂
R¹ = p-nitrophenyl
R² = —OCH₂CH₂CH₂CH₃

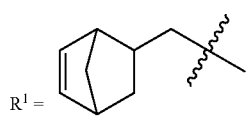 [SMILES: *CC1CC2C=CC1C2]

R¹ =

R¹ = benzyl
R⁵ = Cl
R⁷ = OH

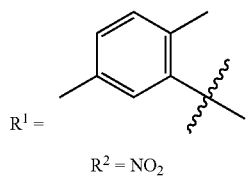

R¹ =

R² = NO₂

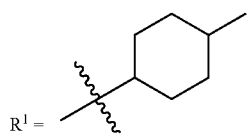

R¹ =

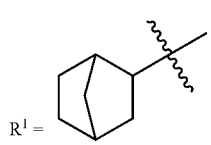 [SMILES: *C1CC2CCC1C2]

R¹ =

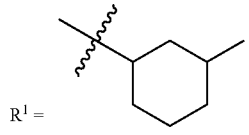 [SMILES: *C1CCCC(C)C1]

R¹ =

TABLE 2-continued

Substituents of Formula II

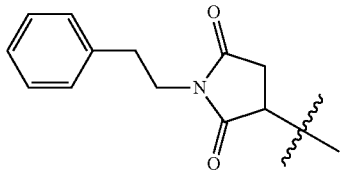

R¹ =

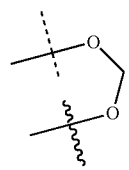

R² & R³ = wherein:
----- refers to the bond connecting R² to Formula II; and
∿∿∿ refers to the bond connecting R³ to Formula II

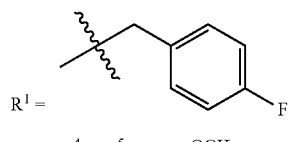

R¹ =

R⁴ & R⁵ = —OCH₃

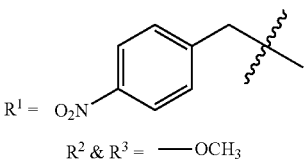

R¹ = O₂N

R² & R³ = —OCH₃

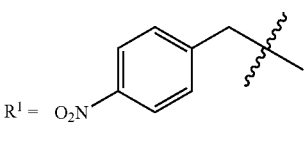

R¹ = O₂N

R³ & R⁴ = OCH₃

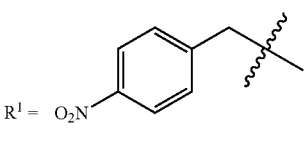

R¹ = O₂N

R² & R⁴ = —OCH₃

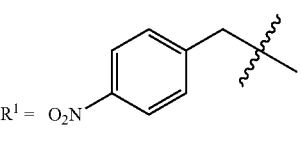

R¹ = O₂N

R⁷ = F

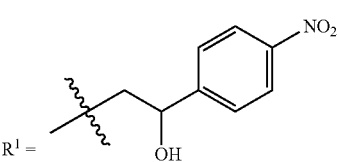 [SMILES: *CC(O)c1ccc([N+](=O)[O-])cc1]

R¹ =

TABLE 2-continued

Substituents of Formula II

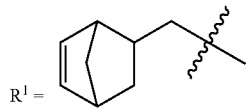

R² = NO₂
R⁶ = (═O)

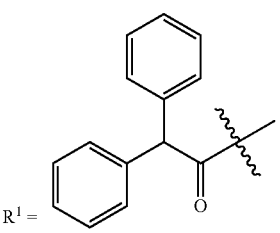

R⁶ = O
R⁷ = OCH₃

R¹ = cyclohexyl

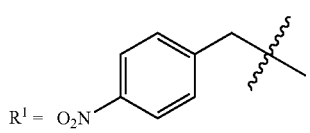

R⁵ = Br
R⁷ = OH

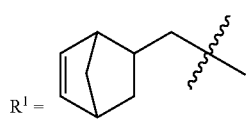

R⁵ = Br
R⁷ = OH

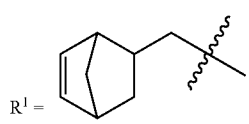

R⁷ = NO₂

R¹ = sec-butyl
R² = NO₂

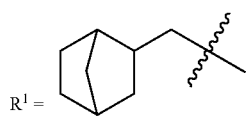

R² = NO₂

R¹ = cyclopentyl
R² = NO₂
R¹ = cycloheptyl
R² = NO₂
R¹ = ethyl
R² = tert-butyl
R⁶ = O TABLE 2-continued Substituents of Formula II

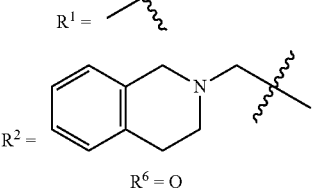

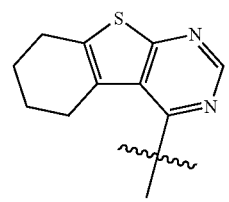

R⁶ = O

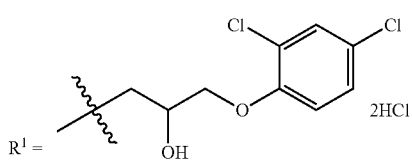 [SMILES: *CC(O)COc1ccc(Cl)cc1Cl]

R² = —OCH₃

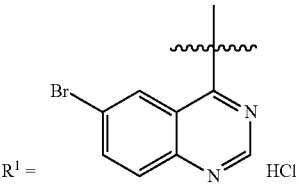 [SMILES: *c1ncnc2ccc(Br)cc12 ; Cl]

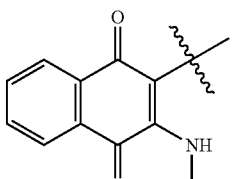

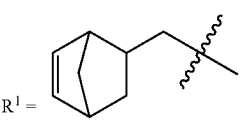

R² & R³ = —OCH₃

The present application further provides a compound of Formula IIa:

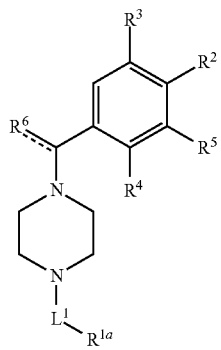

IIa

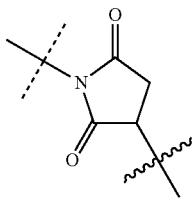

wherein:

〰️ indicates the bond between $L^1$ and the piperazine group of Formula IIa; and ------ indicates the bond between $L^1$ and $R^{1a}$.

In some embodiments, $R^{1a}$ is OH. In some embodiments, $L^1$ is a bond and $R^{1a}$ is OH. In some embodiments, $R^{1a}$ is a $C_{1-4}$ alkyl group. In some embodiments, $L^1$ is a bond and $R^{1a}$ is a $C_{1-4}$ alkyl group. In some embodiments, $R^{1a}$ is selected from the group consisting of methyl and ethyl. In some embodiments, $R^{1a}$ is a $C_{5-10}$ cycloalkyl group which is optionally substituted by one $C_{1-4}$ alkyl group. In some embodiments, $R^{1a}$ is a $C_{5-7}$ cycloalkyl group which is optionally substituted by one $C_{1-4}$ cycloalkyl group. In some embodiments, $R^{1a}$ is a $C_{8-10}$ cycloalkyl group. In some embodiments, $R^{1a}$ is selected from the group consisting of cyclopentyl, cyclohexyl, 3-methylcyclohexyl, cycloheptyl, and

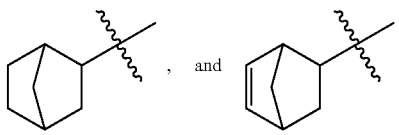

In some embodiments, $R^{1a}$ is a 8-10 membered heteroaryl group. In some embodiments, $R^{1a}$ is a 8-10 membered heteroaryl group comprising two ring heteroatoms which are oxygen. In some embodiments, $R^{1a}$ is a 10-membered heteroaryl group comprising two ring heteroatoms which are oxygen. In some embodiments, $R^{1a}$ is:

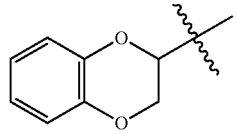

or a pharmaceutically acceptable salt thereof, wherein:

$L^1$ is selected from the group consisting of a bond, $C_{1-4}$ alkylene, $C_{2-4}$ alkenylene, $C_{1-4}$ hydroxyalkylene, $C_{1-4}$ alkyleneoxy, 4-6 membered heterocycloalkylene, and C(=O), wherein the $C_{1-4}$ alkyleneoxy is further optionally substituted by one OH group;

$R^{1a}$ is selected from the group consisting of OH, $C_{1-4}$ alkyl, $C_{5-10}$ cycloalkyl, 8-10 membered heteroaryl, phenyl, —($C_{1-4}$ alkylene)-(phenyl), and 10-13 membered heteroaryl, wherein the $C_{5-10}$ cycloalkyl, phenyl, and the phenyl group of the —($C_{1-4}$ alkylene)-(phenyl) are each optionally substituted by 1, 2, or 3 substituents independently selected from the group consisting of halo, OH, $NO_2$, $C_{1-4}$ alkyl, and $C_{1-4}$ alkoxy, and wherein the 10-13 membered heteroaryl is optionally substituted by one halo group;

$R^2$ is selected from the group consisting of H, halo, OH, $NO_2$, $C_{1-4}$ alkyl, $C_{1-4}$ alkoxy, and —($C_{1-4}$ alkylene)-(8-10 membered heteroaryl);

$R^3$ is selected from the group consisting of H, halo, $C_{1-4}$ alkoxy, and phenoxy; or alternatively, $R^2$ and $R^3$ come together, in combination with the carbon atoms to which they are attached, to form a 5-6 membered heterocycloalkyl or a $C_{6-10}$ aryl;

$R^4$ is selected from the group consisting of H, OH, and $C_{1-4}$ alkoxy;

$R^5$ is selected from the group consisting of H, halo, $C_{1-4}$ alkoxy, and phenoxy; and $R^6$ is selected from the group consisting of H and oxo.

In some embodiments, $L^1$ is a bond. In some embodiments, $L^1$ is a $C_{1-4}$ alkylene. In some embodiments, $L^1$ is selected from the group consisting of methylene and ethylene. In some embodiments, $L^1$ is $C_{2-4}$ alkenylene. In some embodiments, $L^1$ is propenylene. In some embodiments, $L^1$ is —$CH_2CH=CH$—. In some embodiments, $L^1$ is $C_{1-4}$ hydroxyalkylene. In some embodiments, $L^1$ is —$CH_2CH$(OH)—. In some embodiments, $L^1$ is a $C_{1-4}$ alkyleneoxy which is further substituted by one OH group. In some embodiments, $L^1$ is a propoxy group which is further substituted by one OH group. In some embodiments, $L^1$ is —$CH_2CH(OH)CH_2O$—. In some embodiments, $L^1$ is C(=O). In some embodiments, $L^1$ is a 4-6 membered heterocycloalkylene. In some embodiments, $L^1$ is a 4-6 membered heterocycloalkylene comprising one ring heteroatom which is nitrogen. In some embodiments, $L^1$ is a 5-membered heterocycloalkylene comprising one ring heteroatom which is nitrogen. In some embodiments, $L^1$ is:

In some embodiments, $R^{1a}$ is phenyl or —($C_{1-4}$ alkylene)-(phenyl), wherein the phenyl and the phenyl group of the —($C_{1-4}$ alkylene)-(phenyl) are each optionally substituted by 1, 2, or 3 substituents independently selected from the group consisting of halo, OH, $NO_2$, $C_{1-4}$ alkyl, and $C_{1-4}$ alkoxy. In some embodiments, $R^{1a}$ is phenyl or —($C_{1-4}$ alkylene)-(phenyl), wherein the phenyl and the phenyl group of the —($C_{1-4}$ alkylene)-(phenyl) are each optionally substituted by 1, 2, or 3 substituents independently selected from the group consisting of halo, OH, $NO_2$, $C_{1-4}$ alkyl, and $C_{1-4}$ alkoxy. In some embodiments, $R^{1a}$ is selected from the group consisting of phenyl, —($CH_2$)-(phenyl), and —($CH_2CH_2$)-(phenyl), wherein the phenyl and the phenyl group of the —($CH_2$)-(phenyl) and —($CH_2CH_2$)-(phenyl) are each optionally substituted by 1, 2, or 3 substituents independently selected from the group consisting of halo, OH, $NO_2$, $C_{1-4}$ alkyl, and $C_{1-4}$ alkoxy. In some embodiments, the phenyl and the phenyl group of the —(CH$_2$)-(phenyl) and —(CH$_2$CH$_2$)-(phenyl) are unsubstituted. In some embodiments, the phenyl and the phenyl group of the —(CH$_2$)-(phenyl) and —(CH$_2$CH$_2$)-(phenyl) are substituted by 1, 2, or 3 substituents independently selected from the group consisting of halo, OH, NO$_2$, C$_{1-4}$ alkyl, and C$_{1-4}$ alkoxy. In some embodiments, the phenyl and the phenyl group of the —(CH$_2$)-(phenyl) and —(CH$_2$CH$_2$)-(phenyl) are substituted by 1, 2, or 3 substituents independently selected from the group consisting of fluoro, chloro, bromo, OH, NO$_2$, methyl, ethyl, 2-butyl, and methoxy.

In some embodiments, R$^{1a}$ is a 10-13 membered heteroaryl group which is optionally substituted by one halo group. In some embodiments, R$^{1a}$ is 10-membered heteroaryl which is substituted by one halo group. In some embodiments, R$^{1a}$ is 10-membered heteroaryl which is substituted by one halo group and wherein the 10-membered heteroaryl comprises two ring heteroatoms which are nitrogen. In some embodiments, R$^{1a}$ is a 13-membered heteroaryl group. In some embodiments, R$^{1a}$ is a 13-membered heteroaryl group comprising two ring heteroatoms which are nitrogen and one ring heteroatom which is sulfur. In some embodiments, R$^{1a}$ is selected from the group consisting of:

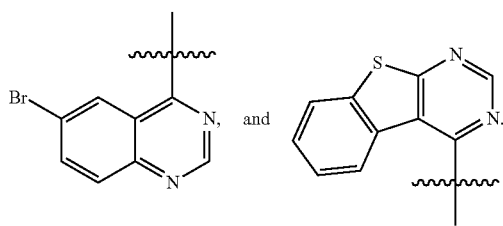 [SMILES: *c1ncnc2ccc(Br)cc12 ; *c1ncnc2sc3ccccc3c12]

In some embodiments, R$^2$ is H. In some embodiments, R$^2$ is halo. In some embodiments, R$^2$ is selected from the group consisting of F and Cl. In some embodiments, R$^2$ is OH. In some embodiments, R$^2$ is C$_{1-4}$ alkyl. In some embodiments, R$^2$ is selected from the group consisting of methyl, ethyl, isopropyl, and tert-butyl. In some embodiments, R$^2$ is NO$_2$. In some embodiments, R$^2$ is C$_{1-4}$ alkoxy. In some embodiments, R$^2$ is selected from the group consisting of methoxy, ethoxy, and butoxy.

In some embodiments, R$^2$ is —(C$_{1-4}$ alkylene)-(8-10 membered heteroaryl). In some embodiments, R$^2$ is —(C$_{1-4}$ alkylene)-(8-10 membered heteroaryl), wherein the 8-10 membered heteroaryl group comprises one ring heteroatom which is nitrogen. In some embodiments, R$^2$ is —(CH$_2$)-(8-10 membered heteroaryl), wherein the 8-10 membered heteroaryl group comprises one ring heteroatom which is nitrogen. In some embodiments, R$^2$ is —(CH$_2$)-(10-membered heteroaryl), wherein the 10-membered heteroaryl group comprises one ring heteroatom which is nitrogen. In some embodiments, R$^2$ is:

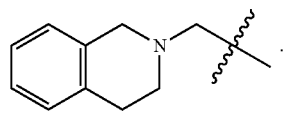 [SMILES: *CN1CCc2ccccc2C1]

In some embodiments, R$^3$ is H. In some embodiments, R$^3$ is halo. In some embodiments, R$^3$ is selected from the group consisting of Cl and Br. In some embodiments, R$^3$ is C$_{1-4}$ alkoxy or phenoxy. In some embodiments, R$^3$ is methoxy or phenoxy.

In some embodiments, R$^2$ and R$^3$ come together, in combination with the carbon atoms to which they are attached, to form a 5-6 membered heterocycloalkyl or a C$_{6-10}$ aryl. In some embodiments, R$^2$ and R$^3$ come together, in combination with the carbon atoms to which they are attached, to form a 5-6 membered heterocycloalkyl. In some embodiments, R$^2$ and R$^3$ come together, in combination with the carbon atoms to which they are attached, to form a 5-6 membered heterocycloalkyl wherein the 5-6 membered heterocycloalkyl comprises two ring atoms which are oxygen. In some embodiments, R$^2$ and R$^3$ come together, in combination with the carbon atoms to which they are attached, to form a C$_{6-10}$ aryl. In some embodiments, R$^2$ and R$^3$ come together, in combination with the carbon atoms to which they are attached, to form a C$_7$ aryl. In some embodiments, R$^2$ and R$^3$ come together, in combination with the carbon atoms to which they are attached, to form a group selected from:

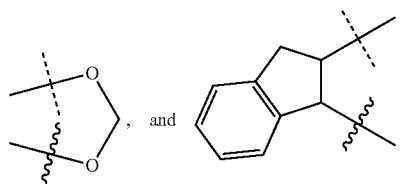

wherein:

------ indicates the bond formed by R$^2$ and the phenyl group; and

∿∿∿ indicates the bond formed by R$^3$ and the phenyl group.

In some embodiments, R$^4$ is H. In some embodiments, R$^4$ is OH. In some embodiments, R$^4$ is methoxy.

In some embodiments, R$^5$ is H. In some embodiments, R$^5$ is halo. In some embodiments, R$^5$ is selected from the group consisting of Cl and Br. In some embodiments, R$^5$ is C$_{1-4}$ alkoxy or phenoxy. In some embodiments, R$^5$ is methoxy or phenoxy.

In some embodiments, R$^6$ is H. In some embodiments, R$^6$ is oxo (i.e., =O).

In some embodiments, the compound of Formula IIa is selected from the group of compounds provided in Table 2A.

TABLE 2A

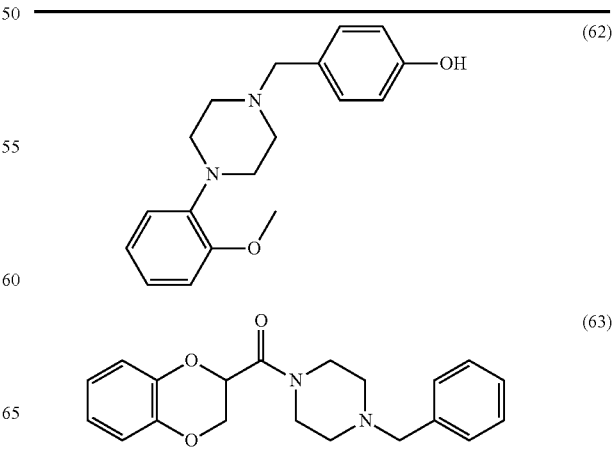

TABLE 2A-continued
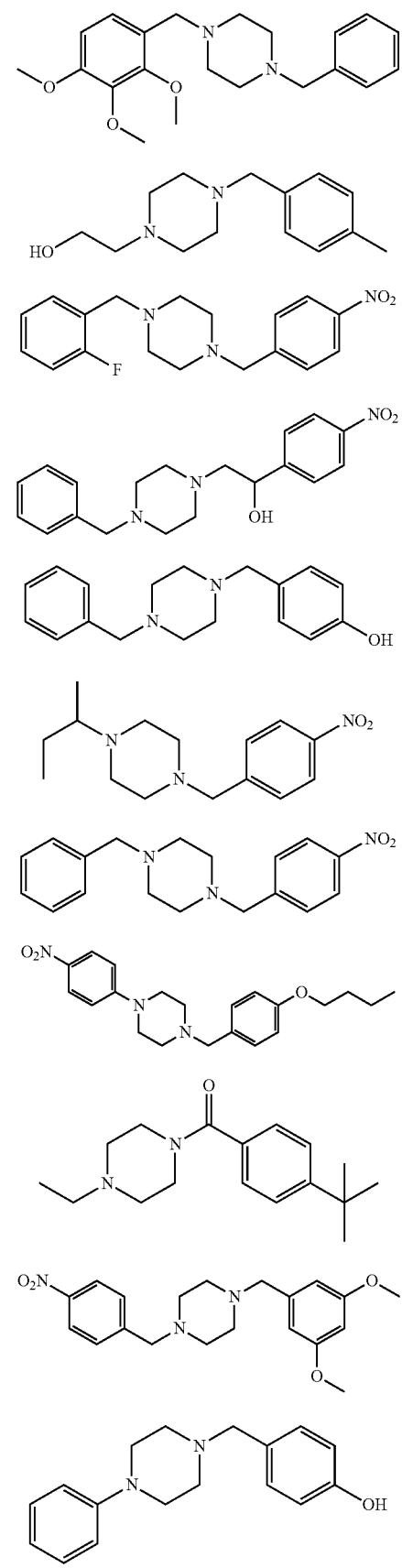
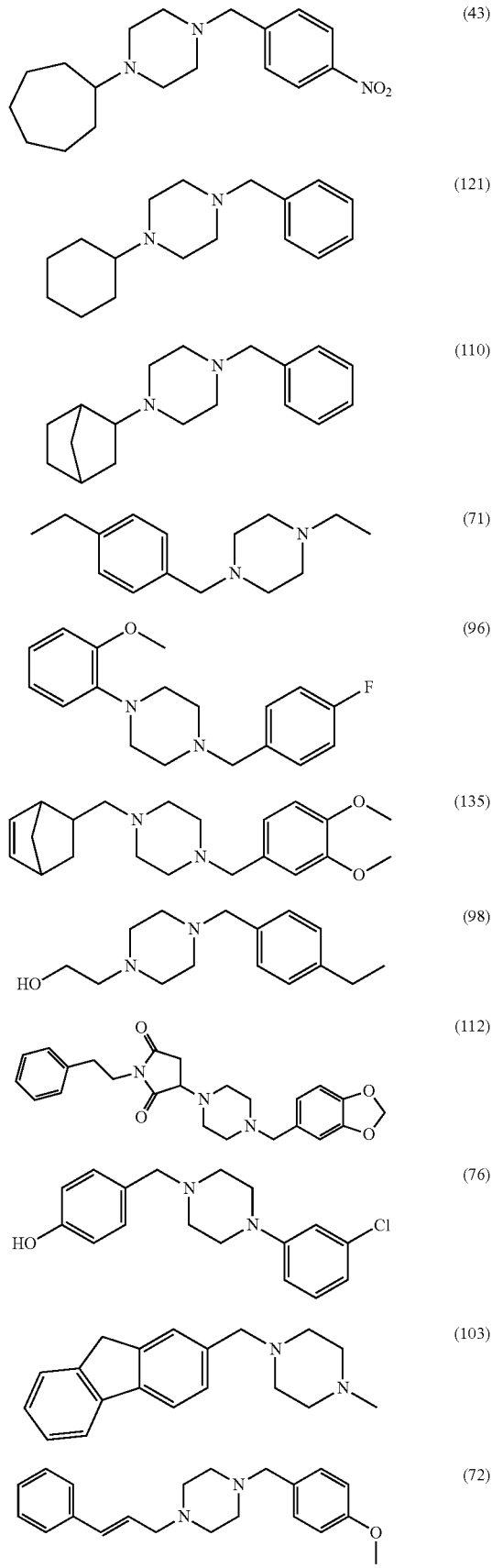

TABLE 2A-continued
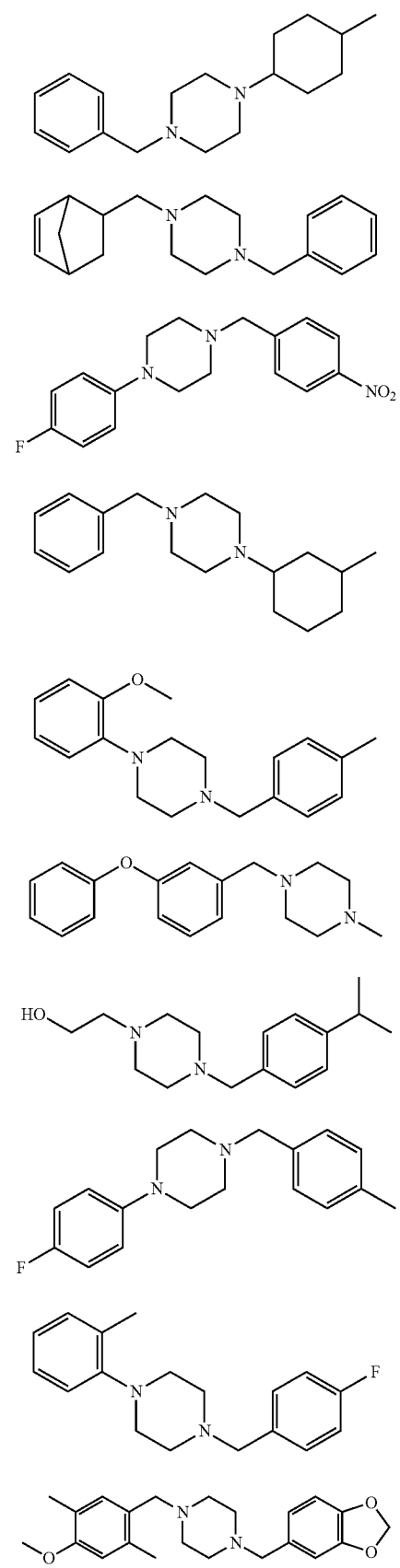
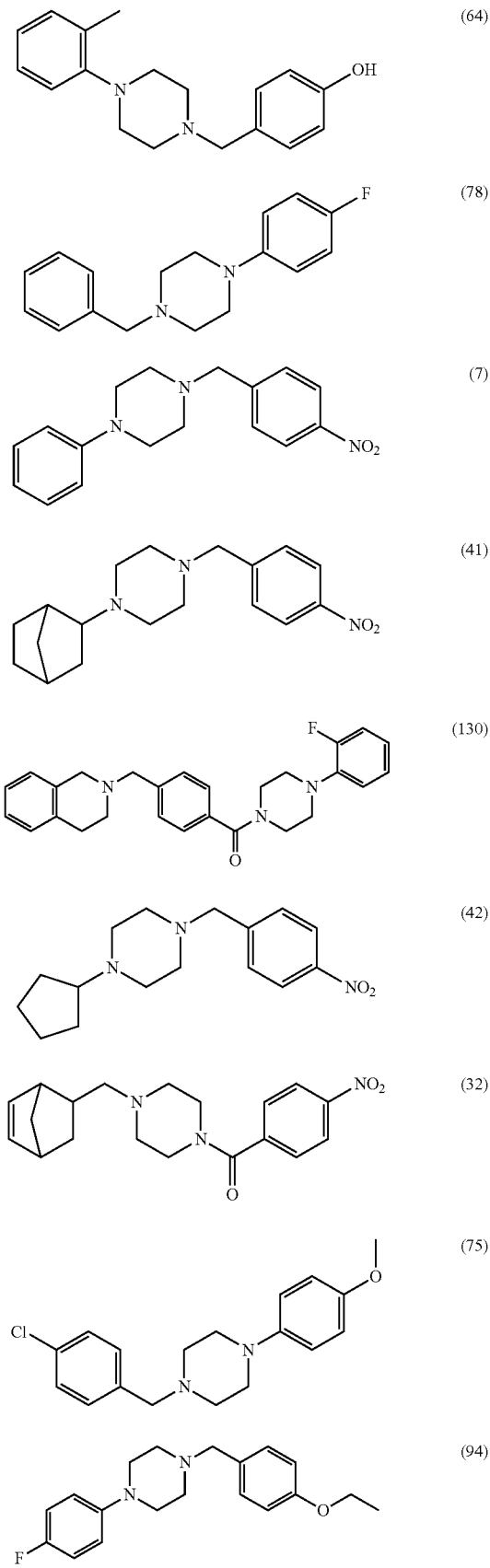

TABLE 2A-continued
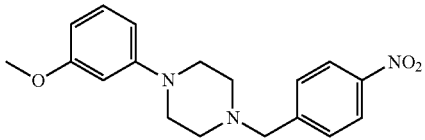 [SMILES: COc1cccc(N2CCN(Cc3ccc([N+](=O)[O-])cc3)CC2)c1] (13)
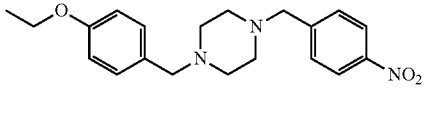 [SMILES: CCOc1ccc(CN2CCN(Cc3ccc([N+](=O)[O-])cc3)CC2)cc1] (8)
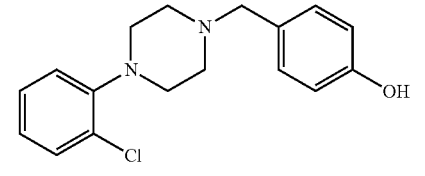 [SMILES: Oc1ccc(CN2CCN(c3ccccc3Cl)CC2)cc1] (66)
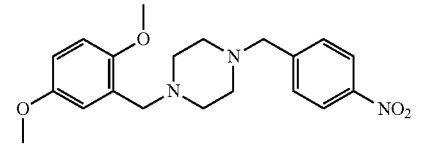 [SMILES: COc1ccc(OC)c(CN2CCN(Cc3ccc([N+](=O)[O-])cc3)CC2)c1] (27)
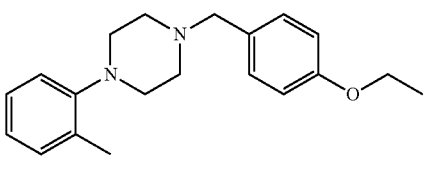 [SMILES: CCOc1ccc(CN2CCN(c3ccccc3C)CC2)cc1] (88)
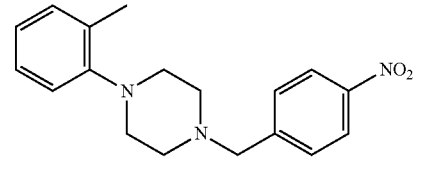 [SMILES: Cc1ccccc1N1CCN(Cc2ccc([N+](=O)[O-])cc2)CC1] (4)
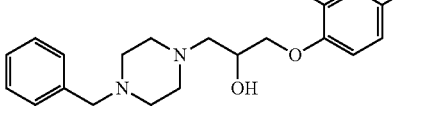 (132)
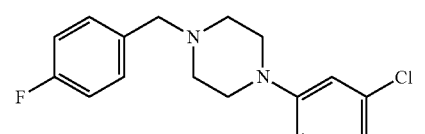 (77)
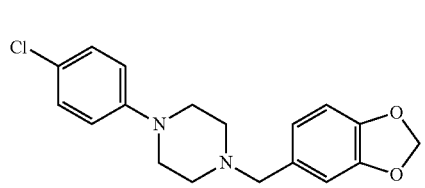 [SMILES: Clc1ccc(N2CCN(Cc3ccc4c(c3)OCO4)CC2)cc1] (67)
TABLE 2A-continued
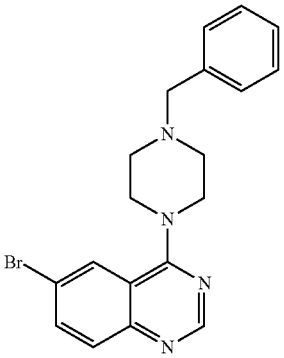 [SMILES: Brc1ccc2ncnc(N3CCN(Cc4ccccc4)CC3)c2c1] (133)
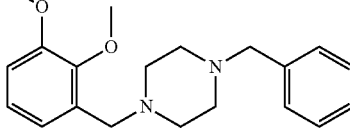 (113)
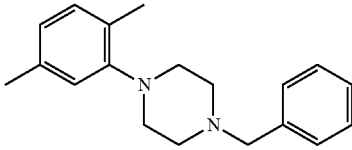 (16)
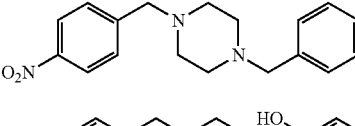 (26)
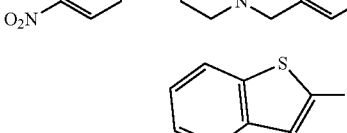 (34)
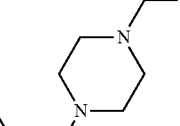 (131)
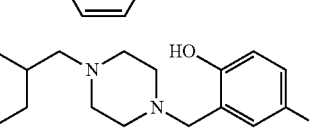 (123)
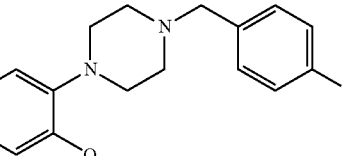 and
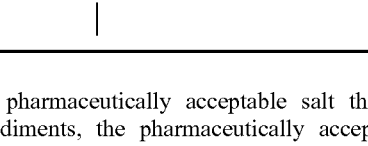 (95)
or a pharmaceutically acceptable salt thereof. In some embodiments, the pharmaceutically acceptable salt is a hydrochloride salt.

The present application further provides a compound of Formula III:

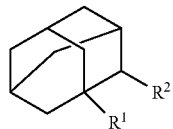

or a pharmaceutically acceptable salt thereof, wherein $R^1$ and $R^2$ of Formula III are as defined herein.

In some embodiments, each $R^1$ and $R^2$, unless specified otherwise in Table 3, is selected from the group consisting of H, OH, SH, CN, $NO_2$, halo, oxo, $C_{1-6}$ alkyl, $C_{2-6}$ alkenyl, $C_{2-6}$ alkynyl, $C_{1-6}$ haloalkyl, $C_{1-6}$ cyanoalkyl, $C_{1-6}$ hydroxyalkyl, $C_{1-6}$ alkoxy, —($C_{1-6}$ alkyl)-($C_{1-6}$ alkoxy), —($C_{1-6}$ alkoxy)-($C_{1-6}$ alkoxy), $C_{1-6}$ haloalkoxy, $C_{3-10}$ cycloalkyl, $C_{6-10}$ aryl, 5-10 membered heteroaryl, 4-10 membered heterocycloalkyl, amino, $C_{1-6}$ alkylamino, di($C_{1-6}$ alkyl)amino, carbamyl, $C_{1-6}$ alkylcarbamyl, di($C_{1-6}$ alkyl)carbamyl, carbamoyl, $C_{1-6}$ alkylcarbamoyl, di($C_{1-6}$ alkyl)carbamoyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonyl amino, $C_{1-6}$ alkylaminocarbonylamino, and di($C_{1-6}$ alkyl)aminocarbonylamino. In some embodiments, each $R^1$ and $R^2$ unless specified otherwise in Table 3, is H. In some embodiments, at least one of $R^1$ and $R^2$ is not H.

TABLE 3

Substituents of Formula III $R^1 =$ 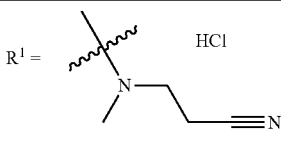 HCl $R^2 =$ 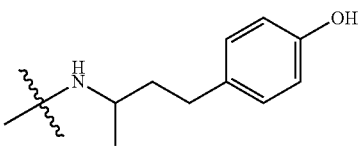

$R^2 =$ 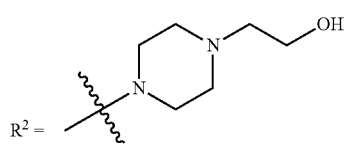 [SMILES: *N1CCN(CCO)CC1]

$R^2 =$ 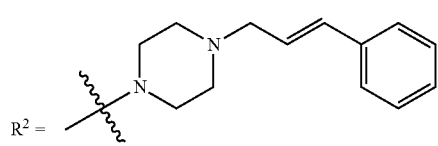 [SMILES: *N1CCN(C/C=C/c2ccccc2)CC1]

$R^2 =$ 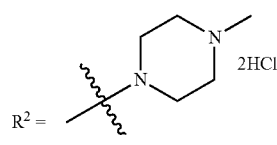 2HCl

TABLE 3-continued

Substituents of Formula III $R^1 =$ 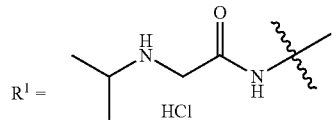 HCl $R^1 =$ 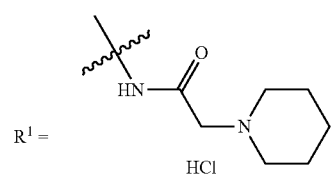 [SMILES: *NC(=O)CN1CCCCC1 ; Cl] HCl $R^1 =$ 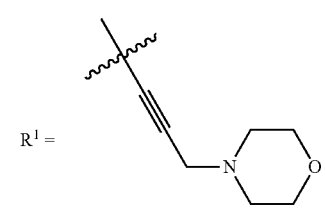 [SMILES: *C#CCN1CCOCC1]

$R^2 =$ 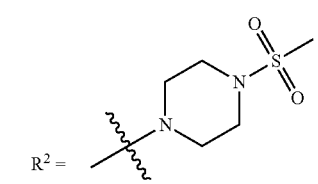 [SMILES: *N1CCN(S(C)(=O)=O)CC1]

$R^1 =$ 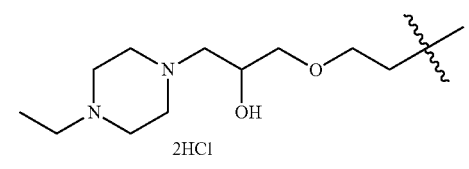 2HCl $R^1 =$ 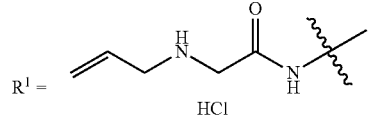 HCl $R^1 =$ 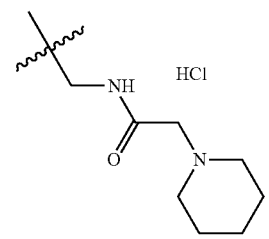 HCl $R^1 =$ 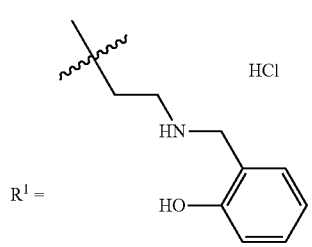 [SMILES: *CCNCc1ccccc1O ; Cl] HCl TABLE 3-continued Substituents of Formula III

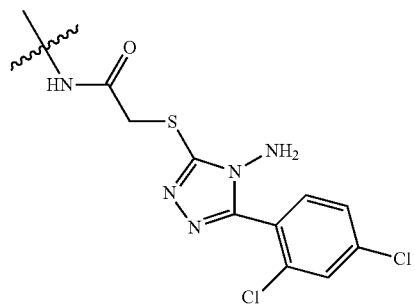

R¹ =

The present application further provides a compound of Formula IIIa:

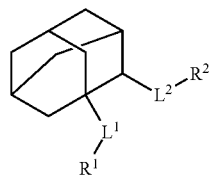

IIIa or a pharmaceutically acceptable salt thereof, wherein:
L¹ is selected from the group consisting of a bond, NH, N($C_{1-4}$ alkyl), $C_{2-4}$ alkynyl, NHC(=O)($C_{1-4}$ thioalkyl), $C_{1-6}$ alkyleneoxy, 5-6 membered heterocycloalkyl, NHC(=O)$C_{1-4}$ alkylene, and ($C_{1-4}$ alkylene)-NHC(=O)—($C_{1-4}$ alkylene)-, wherein the $C_{1-6}$ alkyleneoxy is further optionally substituted by one OH group;
$R^{1a}$ is selected from the group consisting of H, $C_{1-4}$ alkyl, $C_{2-4}$ alkenyl, $C_{1-4}$ cyanoalkylene, 5-6 membered heterocycloalkyl, 5-6 membered heteroaryl, NH($C_{1-4}$ alkyl), and NH($C_{2-4}$ alkenyl), wherein the $C_{1-4}$ alkyl and $C_{2-4}$ alkenyl are each optionally substituted by one substituent selected from the group consisting of phenyl and hydroxyphenyl, and wherein the 5-6 membered heterocycloalkyl and 5-6 membered heteroaryl are each optionally substituted by 1 or 2 substituents independently selected from the group consisting of $C_{1-4}$ alkyl, $NH_2$ and di-halo substituted phenyl;
L² is selected from the group consisting of a bond and 5-6 membered heterocycloalkyl; and
$R^{2a}$ is selected from the group consisting of H, $C_{1-4}$ hydroxyalkyl, —$SO_2$($C_{1-4}$ alkyl).
In some embodiments, L¹ is a bond. In some embodiments, L¹ is selected from the group consisting of NH and N($C_{1-4}$ alkyl). In some embodiments, L¹ is selected from the group consisting of NH and N($CH_3$). In some embodiments, L¹ is $C_{2-4}$ alkynyl. In some embodiments, L¹ is —C≡C$CH_2$—. In some embodiments, L¹ is NHC(=O)($C_{1-4}$ thioalkyl). In some embodiments, L¹ is L¹ is NHC(=O)$CH_2$S—. In some embodiments, L¹ is $C_{1-6}$ alkyleneoxy which is further substituted by one OH group. In some embodiments, L¹ is —$CH_2CH_2OCH_2CH(OH)CH_2$. In some embodiments, L¹ is a 5-6 membered heterocycloalkyl group. In some embodiments, L¹ is a 5-6 membered heterocycloalkyl group wherein the 5-6 membered heterocycloalkyl group comprises two ring heteroatoms which are nitrogen. In some embodiments, L¹ is piperazinyl. In some embodiments, L¹ is selected from the group consisting of NHC(=O)$C_{1-4}$ alkylene and ($C_{1-4}$ alkylene)-NHC(=O)—($C_{1-4}$ alkylene)-. In some embodiments, L¹ is selected from the group consisting of —NHC(=O)$CH_2$— and —$CH_2$NHC(=O)$CH_2$—.

In some embodiments, $R^{1a}$ is H. In some embodiments, L¹ is a bond and $R^{1a}$ is H. In some embodiments, $R^{1a}$ is selected from the group consisting of $C_{1-4}$ alkyl, $C_{2-4}$ alkenyl, and $C_{1-4}$ cyanoalkyl, wherein the $C_{1-4}$ alkyl and $C_{2-4}$ alkenyl are each optionally substituted by one substituent selected from the group consisting of phenyl and hydroxyphenyl. In some embodiments, $R^{1a}$ is selected from the group consisting of $CH_2CH_2CN$,

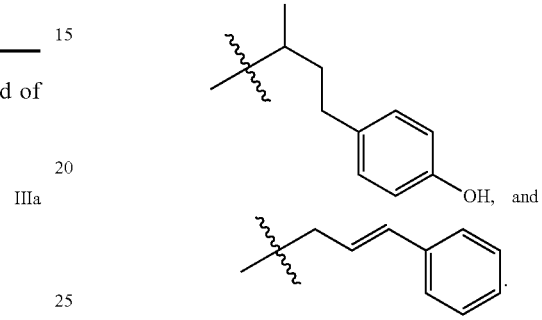

In some embodiments, $R^{1a}$ is selected from the group consisting of 5-6 membered heterocycloalkyl and 5-6 membered heteroaryl, wherein the 5-6 membered heterocycloalkyl and 5-6 membered heteroaryl are each optionally substituted by 1 or 2 substituents independently selected from the group consisting of $C_{1-4}$ alkyl, $NH_2$ and di-halo substituted phenyl. In some embodiments, $R^{1a}$ is selected from the group consisting of 6-membered heterocycloalkyl and 5-membered heteroaryl, wherein the 6-membered heterocycloalkyl and 5-membered heteroaryl are each optionally substituted by 1 or 2 substituents independently selected from the group consisting of methyl, ethyl, $NH_2$ and di-halo substituted phenyl. In some embodiments, $R^{1a}$ is selected from the group consisting of:

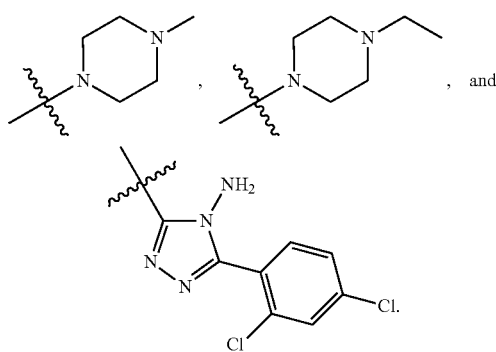

In some embodiments, $R^{1a}$ is selected from the group consisting of NH($C_{1-4}$ alkyl) and NH($C_{2-4}$ alkenyl). In some embodiments, $R^{1a}$ is NH(CH($CH_3$)$_2$). In some embodiments, $R^{1a}$ is NH($CH_2$CH=$CH_2$).
In some embodiments, L² is a bond. In some embodiments, L² is a 5-6 membered heterocycloalkyl group. In some embodiments, L² is a 5-6 membered heterocycloalkyl group, wherein the 5-6 membered heterocycloalkyl group comprises two ring heteroatoms which are nitrogen. In some embodiments, L² is a 6-membered heterocycloalkyl group, wherein the 6-membered heterocycloalkyl group comprises two ring heteroatoms which are nitrogen. In some embodiments, $L^2$ is piperazinyl.

In some embodiments, $R^{2a}$ is H. In some embodiments, $L^2$ is a bond and $R^{2a}$ is H. In some embodiments, $R^{2a}$ is $SO_2(C_{1-4}$ alkyl). In some embodiments, $R^{2a}$ is $SO_2CH_3$. In some embodiments, $R^{2a}$ is $C_{1-4}$ hydroxyalkyl. In some embodiments, $R^{2a}$ is $CH_2CH_2OH$.

In some embodiments, the compound of Formula IIIa is selected from the group of compounds provided in Table 3A.

TABLE 3A

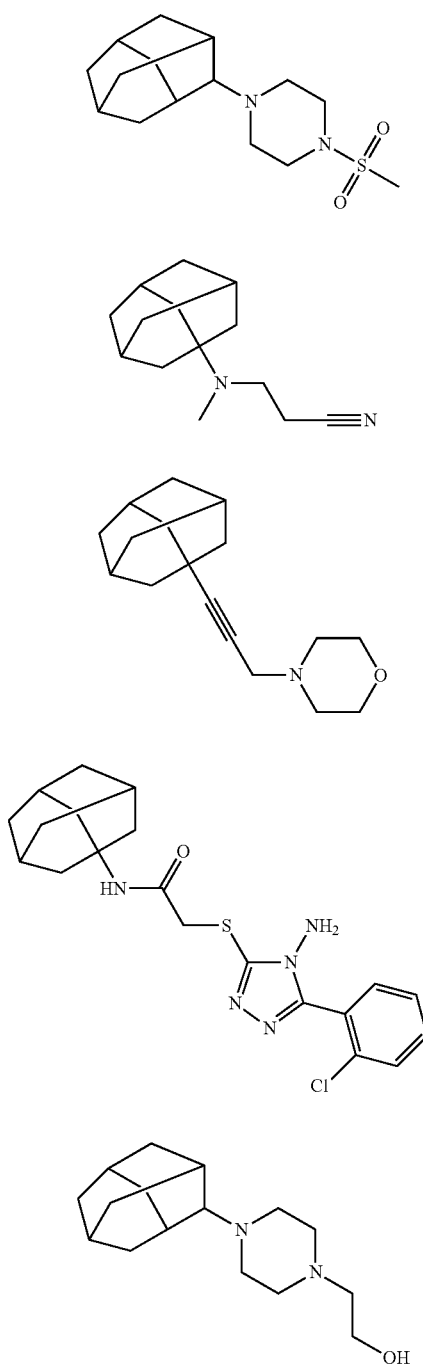

TABLE 3A-continued

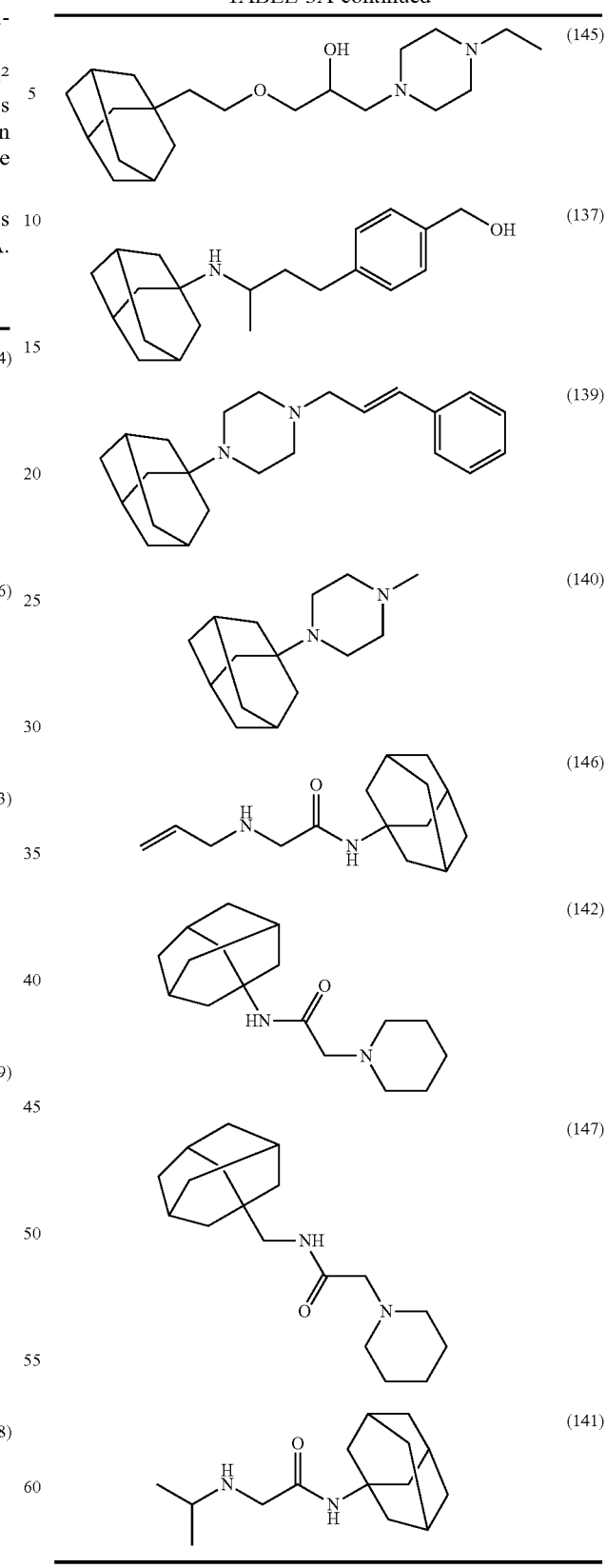

or a pharmaceutically acceptable salt thereof. In some embodiments, the pharmaceutically acceptable salt is a hydrochloride salt.

In some embodiments, the compound is selected from the group provided in Table 4, or a pharmaceutically acceptable salt thereof. Unless specified otherwise, each R group of Table 4 is H.

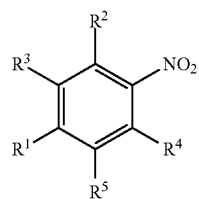

TABLE 4

| Cmpd # | Substituent Groups |
|---|---|
| 1 | R¹ = 3,4-dimethoxyphenethyl-N(CH₃)- |
| 2 | R¹ = 4-methylphenyl-SO₂-4-phenyl- |
| 3 | R¹ = 1,2,3,4-tetrahydroisoquinolin-2-yl |
| 4 | R¹ = 4-(2-methylphenyl)piperazin-1-yl |
| 5 | R¹ = 4-(2,3-dimethylphenyl)piperazin-1-yl |
| 6 | R¹ = 4-benzylpiperazin-1-yl |
| 7 | R¹ = 4-phenylpiperazin-1-yl |
| 8 | R¹ = 4-(4-ethoxybenzyl)piperazin-1-yl |
| 9 | R¹ = 4-(4-fluorophenyl)piperazin-1-yl |
| 11 | R¹ = 2-chlorobenzamido |
| 12 | R¹ = 4-morpholinobutoxy |
| 13 | R¹ = 4-(3-methoxyphenyl)piperazin-1-yl |
| 14 | R¹ = cyclohexyl-N(CH₃)- |
| 15 | R¹ = 4-(4-butoxybenzyl)piperazin-1-yl |
| 16 | R¹ = 4-(2,5-dimethylphenyl)piperazin-1-yl |

TABLE 4-continued
| Cmpd # | Substituent Groups |
|---|---|
| 17 | R² = CH₃<br>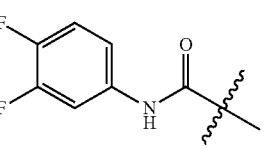<br>R³ = |
| 18 | R¹ = CH₃<br>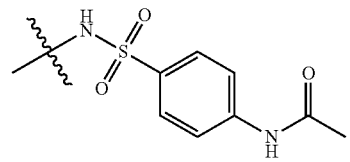<br>R³ = |
| 19 | 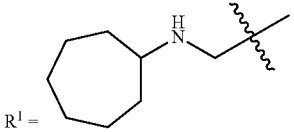<br>R¹ = |
| 20 | 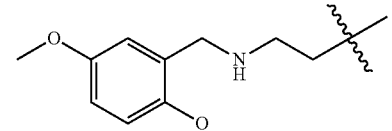<br>R¹ = |
| 21 | 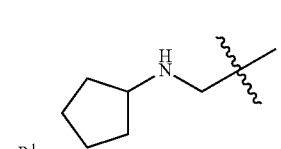<br>R¹ = |
| 22 | 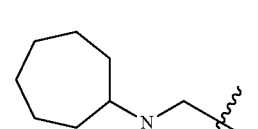<br>R³ = |
| 23 | 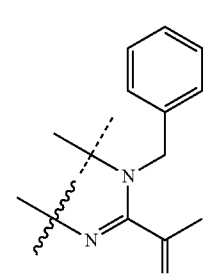<br>R¹ & R³ = |
wherein:
- - - - refers to the bond connecting R¹ to Formula I; and
∿∿∿ refers to the bond connecting R³ to Formula I
| Cmpd # | Substituent Groups |
|---|---|
| 24 | 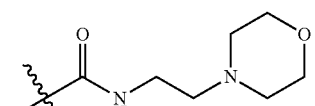<br>R³ =<br>R⁴ = —OMe |
| 25 | 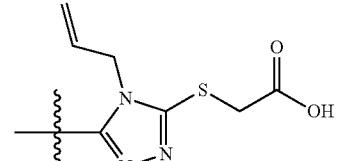<br>R¹ = |
| 26 | 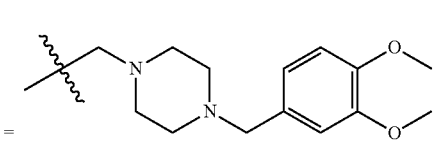<br>R¹ = |
| 27 | 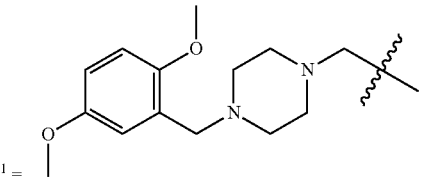<br>R¹ = |
| 28 | 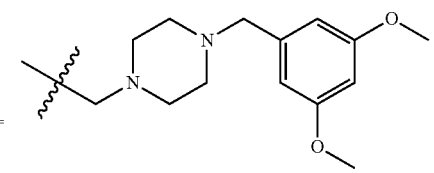<br>R¹ = |
| 29 | 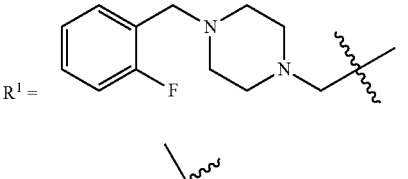<br>R¹ = |
| 30 | 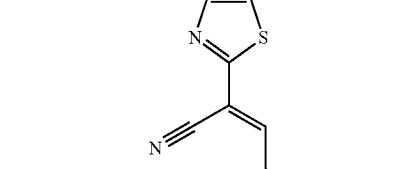<br>R¹ = |
| 31 | 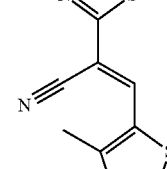<br>R¹ = |

TABLE 4-continued
| Cmpd # | Substituent Groups |
|---|---|
| 32 | R¹ = 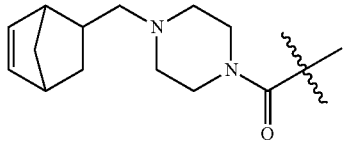 |
| 33 | R¹ = 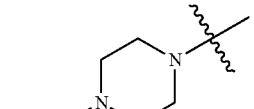  R² = 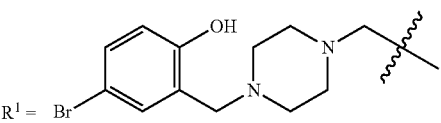 [SMILES: *CN1CCN(Cc2cc(Br)ccc2O)CC1] |
| 34 | R¹ = 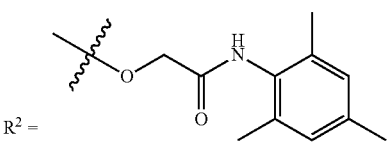 [SMILES: *OCC(=O)Nc1c(C)cc(C)cc1C] |
| 35 | R² = 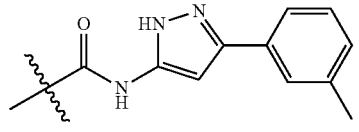 |
| 36 | R¹ = 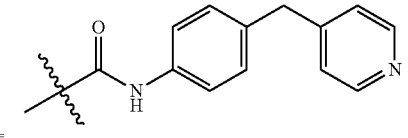 |
| 37 | R¹ = 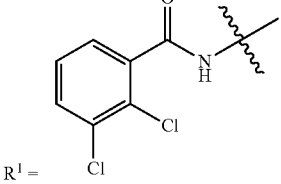  R⁵ = Cl |
| 38 | R¹ = 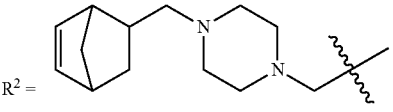 [SMILES: *CN1CCN(CC2CC3C=CC2C3)CC1] |
| 39 | R² = 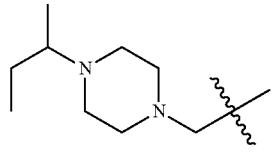 |
| 40 | R¹ = 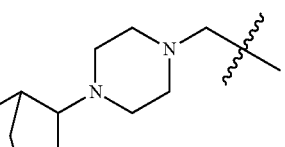 |
| 41 | R¹ = 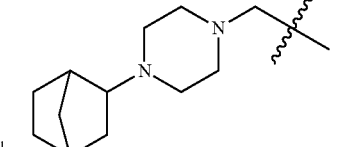 |
| 42 | R¹ = 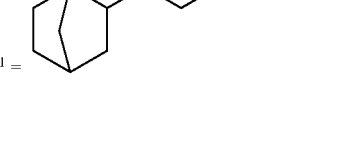 |
| 43 | R¹ = 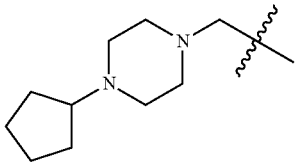 |
| 44 | R² = 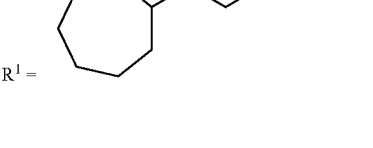 |
| 45 | R² = 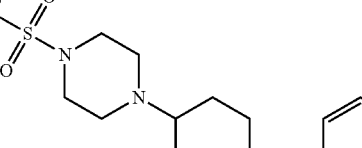  R⁵ = 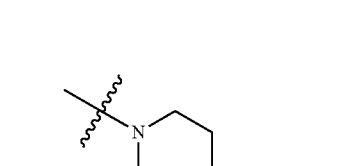 |

TABLE 4-continued
| Cmpd # | Substituent Groups |
|---|---|
| 46 |  |
| 47 | R² = CH₃ 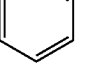 |
| 48 |  |
| 49 | 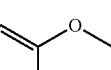 |
| 50 |  R⁴ = —SCH₂CH₃ |
| 51 | R³ = —OCH₃  |
| 52 | R³ = CH₃  |
| 53 | 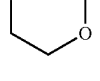 |
| 54 | R² = CH₃  |
| 55 | R² = CH₃  |
| 56 |  |
| 57 |  R⁵ = Cl |

TABLE 4-continued

| Cmpd # | Substituent Groups |
|---|---|
| 58 | $R^1$ = [3-(1,2,3,4-tetrahydroisoquinolin-2-yl)-2,5-dioxopyrrolidin-1-yl] |
| 59 | $R^1$ = pentafluorobenzamido<br>$R_5$ = —OCH$_3$ |
| 60 | $R^2$ = [3-oxo-3-((2,2,6,6-tetramethylpiperidin-4-yl)amino)propyl] |
| 61 | $R^5$ = [3,5-dichloro-4-ethoxybenzamido] |

In some embodiments, the compound is selected from the group provided in Table 5, or a pharmaceutically acceptable salt thereof. Unless specified otherwise, each R group of Table 5 is H.

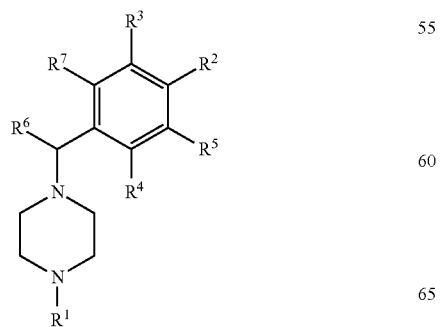

TABLE 5

| Cmpd # | Substituent Groups |
|---|---|
| 4 | $R^1$ = o-tolyl<br>$R^2$ = NO$_2$ |
| 6 | $R^1$ = benzyl<br>$R^3$ = NO$_2$ |
| 7 | $R^1$ = phenyl<br>$R^2$ = NO$_2$ |
| 8 | $R^1$ = p-nitrophenyl<br>$R^2$ = —OCH$_2$CH$_3$ |
| 9 | $R^1$ = 4-fluorophenyl<br>$R^2$ = NO$_2$ |
| 13 | $R^1$ = 3-methoxyphenyl<br>$R^2$ = NO$_2$ |
| 15 | $R^1$ = p-nitrophenyl<br>$R^2$ = —OCH$_2$CH$_2$CH$_2$CH$_3$ |
| 16 | $R^1$ = 2,4-dimethylphenyl<br>$R^2$ = NO$_2$ |
| 24 | $R^1$ = 4-nitrobenzyl<br>$R^2$ & $R^3$ = —OCH$_3$ |
| 27 | $R^1$ = 4-nitrobenzyl<br>$R^3$ & $R^4$ = OCH$_3$ |
| 28 | $R^1$ = 4-nitrobenzyl<br>$R^2$ & $R^4$ = —OCH$_3$ |

TABLE 5-continued

| Cmpd # | Substituent Groups |
|---|---|
| 29 | R¹ = 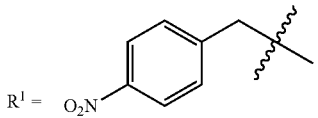<br>R⁷ = F |
| 31 | R¹ = 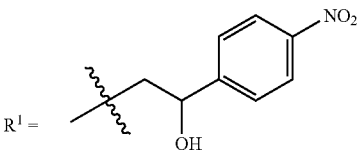 [SMILES: *CC(O)c1ccc([N+](=O)[O-])cc1] |
| 32 | R¹ = 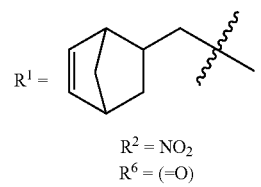<br>R² = NO₂<br>R⁶ = (=O) |
| 34 | R¹ = 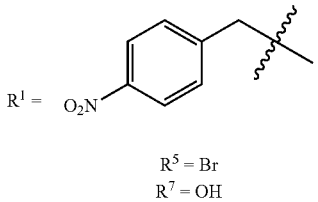 [SMILES: *Cc1ccc([N+](=O)[O-])cc1]<br>R⁵ = Br<br>R⁷ = OH |
| 40 | R¹ = sec-butyl<br>R² = NO₂ |
| 41 | R¹ = 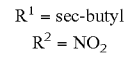<br>R² = NO₂ |
| 42 | R¹ = cyclopentyl<br>R² = NO₂ |
| 43 | R¹ = cycloheptyl<br>R² = NO₂ |
| 62 | R¹ = 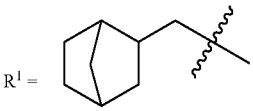<br>R² = OH |
| 63 | R¹ = 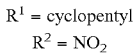 |

TABLE 5-continued

| Cmpd # | Substituent Groups |
|---|---|
| 64 | R¹ = 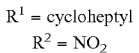 |
| 65 | R¹ = 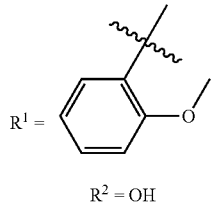 [SMILES: *c1ccccc1OC]<br>R² = OCH₃<br>R³ & R⁴ = CH₃ |
| 66 | R¹ = 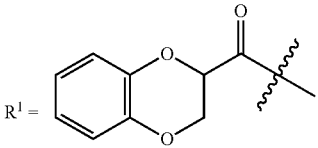 [SMILES: *C(=O)C1COc2ccccc2O1]<br>R² = OH |
| 67 | R¹ = 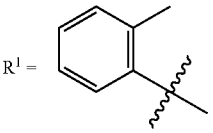 |
|  | R² & R³ = 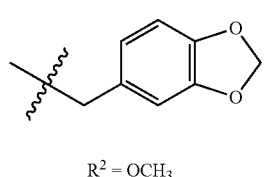<br>wherein:<br>----- refers to the bond connecting R² to Formula II; and<br>∿∿∿ refers to the bond connecting R³ to Formula II |
| 68 | R¹ = 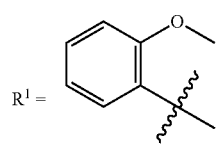<br>R² = Cl |
| 69 | R¹ = 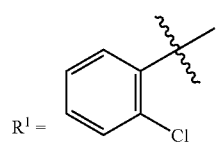<br>R² = F |
| 70 | R¹ = CH₃<br>R² = isopropyl |
| 71 | R¹ and R² = ethyl |
| 72 | R¹ = trans-cinnamyl<br>R² = OCH₃ |

TABLE 5-continued

| Cmpd # | Substituent Groups |
|---|---|
| 74 | 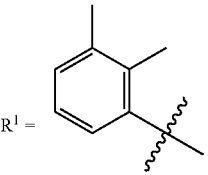 R¹ =<br>R² = NO₂ |
| 75 | 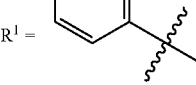 R¹ =<br>R² = Cl |
| 76 | 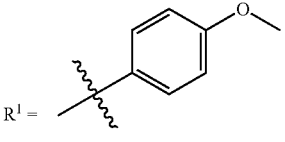 R¹ =<br>R² = OH |
| 77 | 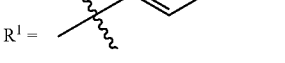 R¹ =<br>R² = F |
| 78 | 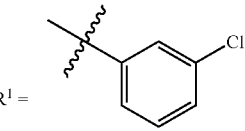 R¹ =<br>R² = F |
| 79 | R¹ = benzyl<br>R² = OH |
| 81 | R¹ = benzyl<br>R², R⁴, and R⁵ = OCH₃ |
| 82 | R¹ = phenyl<br>R² = OH |
| 83 | R¹ = CH₃<br>R⁵ = 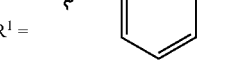 |
| 84 | 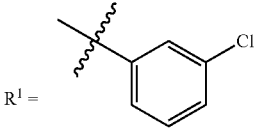 R¹ =<br>R² = ethyl |
| 86 | R¹ = phenyl<br>R² = Br |

TABLE 5-continued

| Cmpd # | Substituent Groups |
|---|---|
| 88 | 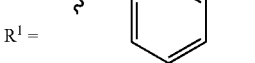 R¹ =<br>R² = —OCH₂CH₃ |
| 90 | 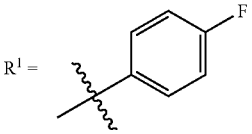 [SMILES: *c1ccc(F)cc1] R¹ =<br>R² = CH₃ |
| 91 | 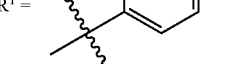 R¹ =<br>R² = F |
| 93 | 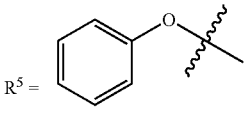 R¹ =<br>R² = CH₃ |
| 94 | 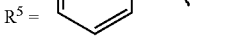 R¹ =<br>R² = —OCH₂CH₃ |
| 95 | 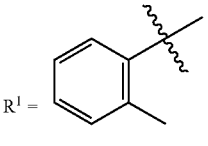 R¹ =<br>R² = —OCH₂CH₃ |
| 96 | 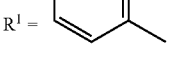 R¹ =<br>R² = F |
| 97 | R¹ = —CH₂CH₂OH<br>R² = isopropyl |
| 98 | R¹ = —CH₂CH₂OH<br>R² = ethyl |
| 99 | R¹ = benzyl<br>R³ & R⁵ = OCH₃ |
| 100 | R¹ = —CH₂CH₂OH<br>R² = CH₃ |

TABLE 5-continued

| Cmpd # | Substituent Groups |
|---|---|
| 101 | R¹ = 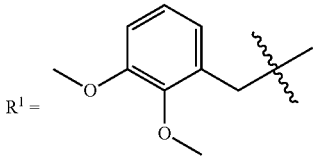<br>R², R³, and R⁵ = —OCH$_3$<br>R⁶ = (=O) |
| 103 | R¹ = CH$_3$<br>R² & R³ = 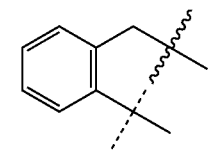<br>wherein:<br>- - - - refers to the bond connnecting R² to Formula II; and<br>∿∿∿ refers to the bond connnecting R³ to Formula II |
| 104 | R¹ = ethyl<br>R² = —N(ethyl)$_2$ |
| 106 | R¹ = 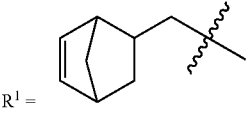 |
| 107 | R¹ = benzyl<br>R⁵ = Cl<br>R⁷ = OH |
| 109 | R¹ = 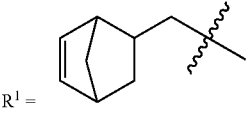 |
| 110 | R¹ = 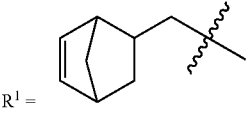 |
| 111 | R¹ = 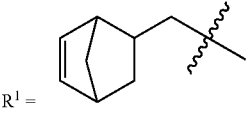 |
| 112 | R¹ = 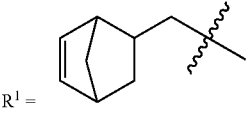<br>R² & R³ = 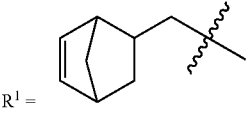<br>wherein:<br>- - - - refers to the bond connecting R² to Formula II; and<br>∿∿∿ refers to the bond connecting R³ to Formula II |
| 113 | R¹ = 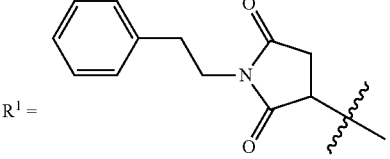<br>R⁴ & R⁵ = —OCH$_3$ |
| 120 | R¹ = 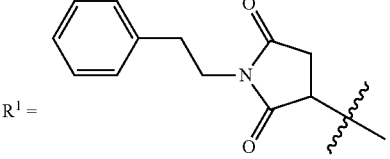<br>R⁶ = O<br>R⁷ = OCH$_3$ |
| 121 | R¹ = cyclohexyl |
| 123 | R¹ = 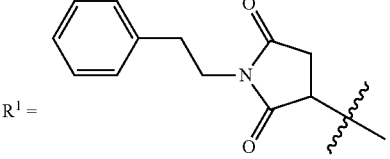<br>R⁵ = Br<br>R⁷ = OH |
| 124 | R¹ = 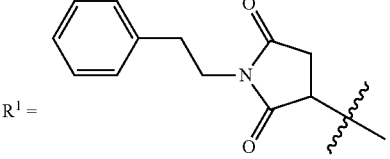<br>R⁷ = NO$_2$ |
| 129 | R¹ = ethyl<br>R² = tert-butyl<br>R⁶ = O |

TABLE 5-continued

| Cmpd # | Substituent Groups |
|---|---|
| 130 | R¹ = 2-fluorophenyl; R² = 1,2,3,4-tetrahydroisoquinolin-2-ylmethyl; R⁶ = O |
| 131 | R¹ = 5,6,7,8-tetrahydro[1]benzothieno[2,3-d]pyrimidin-4-yl; R² = —OCH₃ |
| 132 | R¹ = 3-(2,4-dichlorophenoxy)-2-hydroxypropyl; 2HCl |
| 133 | R¹ = 6-bromoquinazolin-4-yl; HCl |
| 134 | R¹ = 3-acetamido-1,4-dioxo-1,4-dihydronaphthalen-2-yl |
| 135 | R¹ = bicyclo[2.2.1]hept-5-en-2-ylmethyl; R² = R³ = —OCH₃ |

In some embodiments, the compound is selected from the group provided in Table 6, or a pharmaceutically acceptable salt thereof. Unless specified otherwise, each R group of Table 6 is H.

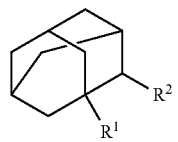

TABLE 6

| Cmpd # | Substituent Groups |
|---|---|
| 136 | R¹ = —N(CH₃)CH₂CH₂CN; HCl |
| 137 | R² = —NHCH(CH₃)CH₂-(4-hydroxyphenyl) |
| 138 | R² = 4-(2-hydroxyethyl)piperazin-1-yl |
| 139 | R² = 4-cinnamylpiperazin-1-yl |
| 140 | R² = 4-methylpiperazin-1-yl; 2HCl |
| 141 | R¹ = —NHC(O)CH₂NH-iPr; HCl |
| 142 | R¹ = —NHC(O)CH₂-(piperidin-1-yl); HCl |
| 143 | R¹ = —C≡C—CH₂-(morpholin-4-yl) |

TABLE 6-continued

| Cmpd # | Substituent Groups |
|---|---|
| 144 | 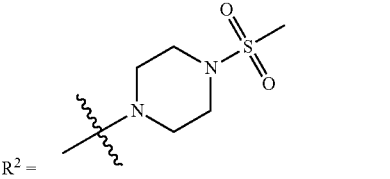 [SMILES: *N1CCN(S(C)(=O)=O)CC1] R² = |
| 145 | 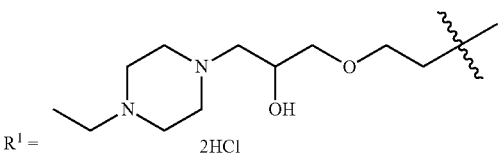 [SMILES: *CCOCC(O)CN1CCN(CC)CC1] R¹ = 2HCl |
| 146 | 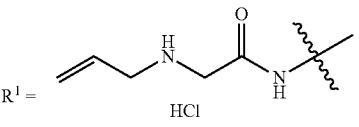 R¹ = HCl |
| 147 | 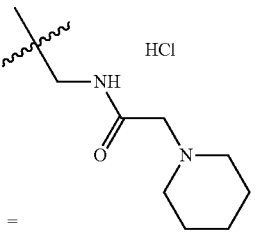 R¹ = |
| 148 | 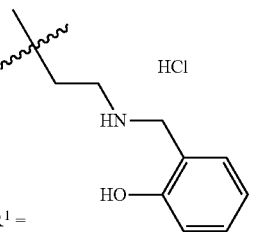 R¹ = |
| 149 | 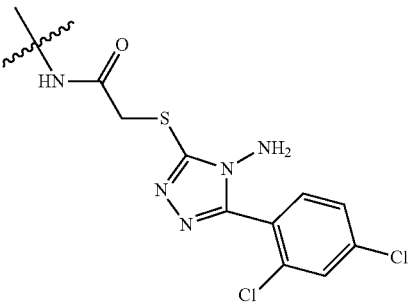 R¹ = |

In some embodiments, the compound is selected from the group of compounds provided in Table 1A, Table 1B, Table 1C, Table 2A, Table 3A, Table 4, Table 5, and Table 6, or a pharmaceutically acceptable salt thereof.

In some embodiments, the compound is selected from the group consisting of:
2-(3,4-dimethoxyphenyl)-N-methyl-N-(4-nitrobenzyl) ethan-1-amine;
N-methyl-N-(4-nitrobenzyl)cyclohexanamine;
3-(adamantan-1-yl(methyl)amino)propanenitrile;
1-(adamantan-2-yl)-4-(methylsulfonyl)piperazine;
4-((4-(2-methoxyphenyl)piperazin-1-yl)methyl)phenol;
(4-benzylpiperazin-1-yl)(2,3-dihydrobenzo[b] 1,4]dioxin-2-yl) methanone;
1-cinnamyl-4-(4-methoxybenzyl)piperazine;
1-(4-fluorobenzyl)-4-(o-tolyl)piperazine; and
1-benzyl-4-(bicyclo[2.2.1]heptan-2-yl)piperazine;
or a pharmaceutically acceptable salt thereof.

In some embodiments, the compound is selected from the group consisting of:
2-(3,4-dimethoxyphenyl)-N-methyl-N-(4-nitrobenzyl) ethan-1-amine; N-methyl-N-(4-nitrobenzyl)cyclohexanamine;
3-(adamantan-1-yl(methyl)amino)propanenitrile hydrochloride;
1-(adamantan-2-yl)-4-(methylsulfonyl)piperazine;
4-((4-(2-methoxyphenyl)piperazin-1-yl)methyl)phenol;
(4-benzylpiperazin-1-yl)(2,3-dihydrobenzo[b] 1,4]dioxin-2-yl) methanone hydrochloride;
1-cinnamyl-4-(4-methoxybenzyl)piperazine;
1-(4-fluorobenzyl)-4-(o-tolyl)piperazine; and
1-benzyl-4-(bicyclo[2.2.1]heptan-2-yl)piperazine.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile hydrochloride).

The phrase "pharmaceutically acceptable" is employed herein to refer to those compounds or salts which are suitable for use in contact with cells (e.g., eukaryotic cells or cyanobacteria) without excessive toxicity or other problem or complication (i.e., the contacting does not affect the viability of the cell).

Methods of Use

The present application further provides a method of increasing lipid accumulation in a cell, comprising contacting the cell with an effective amount of a compound provided herein (e.g. a compound of any one of Formulae I, Ia, Ib, Ic, II, IIa, III, and IIIa, or a pharmaceutically acceptable salt thereof). In some embodiments, the compound is a compound of Formula Ia, or a pharmaceutically acceptable salt thereof, or a compound of Formula Ib, or a pharmaceutically acceptable salt thereof, or a compound of Formula Ic, or a pharmaceutically acceptable salt thereof, or a compound of Formula IIa, or a pharmaceutically acceptable salt thereof, or a compound of Formula IIIa, or a pharmaceutically acceptable salt thereof. In some embodiments, the compound is a compound of Formula I, or a pharmaceutically acceptable salt thereof. In some embodiments, the compound is a compound of Formula II, or a pharmaceutically acceptable salt thereof. In some embodiments, the compound is a compound of Formula III, or a pharmaceutically acceptable salt thereof. In some embodiments, the compound is selected from the group of compounds provided in Table 1A, Table 1B, Table 1C, Table 2A, Table 3A, Table 4, Table 5, and Table 6, or a pharmaceutically acceptable salt thereof.

In some embodiments, the compound is selected from the group consisting of:
2-(3,4-dimethoxyphenyl)-N-methyl-N-(4-nitrobenzyl)ethan-1-amine;
N-methyl-N-(4-nitrobenzyl)cyclohexanamine;
3-(adamantan-1-yl(methyl)amino)propanenitrile;
1-(adamantan-2-yl)-4-(methylsulfonyl)piperazine;
4-((4-(2-methoxyphenyl)piperazin-1-yl)methyl)phenol;
(4-benzylpiperazin-1-yl)(2,3-dihydrobenzo[b] 1,4]dioxin-2-yl) methanone;
1-cinnamyl-4-(4-methoxybenzyl)piperazine;
1-(4-fluorobenzyl)-4-(o-tolyl)piperazine; and
1-benzyl-4-(bicyclo[2.2.1]heptan-2-yl)piperazine;
or a pharmaceutically acceptable salt thereof.

In some embodiments, the compound is selected from the group consisting of:
2-(3,4-dimethoxyphenyl)-N-methyl-N-(4-nitrobenzyl)ethan-1-amine;
N-methyl-N-(4-nitrobenzyl)cyclohexanamine;
3-(adamantan-1-yl(methyl)amino)propanenitrile hydrochloride;
1-(adamantan-2-yl)-4-(methylsulfonyl)piperazine;
4-((4-(2-methoxyphenyl)piperazin-1-yl)methyl)phenol;
(4-benzylpiperazin-1-yl)(2,3-dihydrobenzo[b] 1,4]dioxin-2-yl) methanone hydrochloride;
1-cinnamyl-4-(4-methoxybenzyl)piperazine;
1-(4-fluorobenzyl)-4-(o-tolyl)piperazine; and
1-benzyl-4-(bicyclo[2.2.1]heptan-2-yl)piperazine.

In some embodiments, the compound is selected from the group consisting of:
(2-(3,4-dimethoxyphenyl)-N-methyl-N-(4-nitrobenzyl)ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl)ethan-1-amine);
(4-((4-(2-methoxyphenyl)piperazin-1-yl)methyl)phenol); and
(3-(adamantan-1-yl(methyl)amino)propanenitrile hydrochloride).

In some embodiments, the cell is a eukaryotic cell or a cyanobacteria. In some embodiments, the cell is a eukaryotic cell. In some embodiments, the cell is a cyanobacteria. In some embodiments, the cell is selected from the group consisting of an algal cell, a *drosophila* cell, a yeast cell, or a fungus cell.

Example algal cells include, but are not limited to, *Chlamydomonas reinhardtii, Chlorella sorokiniana, Tetrachlorella alterans, C. protothecoides, C. vulgaris, Nannochloropsis* sp., *P. tricornutum, N. salina, Nannochloris* sp., *N. oculata, Clostridium acetobutylicum, Botryococcus braunii, Dunaliella tertiolecta, Gracilaria, Chlorella* sp., *Pleurochrysis carterae, Sargassum, Ankistrodesmus,*

Example yeast cells include, but are not limited to, *Yarrowia hpolytica, Saccharomyces cerevisiae, Brettanomyces bruxellensis, Candida stellata, Schizosaccharomyces pombe, Torulaspora delbrueckii,* and *Zygosaccharomyces bailii.*

Example fungus cells include, but are not limited to, *Gliocladium roseum, Cunninghamella japonica*, and *Tricoderma reesei.*

In some embodiments, the cell is an algal cell. In some embodiments, the cell is selected from the group consisting of:
*Chlamydomonas reinhardtii;*
*Chlorella sorokiniana;*
*Tetrachlorella alterans;*
*C. protothecoides;*
*C. vulgaris;* and
*Nannochloropsis* sp.

In some embodiments, the cell is an algal cell. In some embodiments, the cell is selected from the group consisting of:
*Chlamydomonas reinhardtii* CC125;
*Chlorella sorokiniana* UTEX 1230;
*Tetrachlorella alterans* UTEX 2453;
*C. protothecoides;*
*C. vulgaris* UTEX 395; and
*Nannochloropsis* sp.

In some embodiments, the increasing lipid accumulation comprises increasing fatty acid accumulation. In some embodiments, the increasing fatty acid accumulation comprises increasing $C_{10-30}$ fatty acid accumulation. In some embodiments, the increasing fatty acid accumulation comprises increasing $C_{10-20}$ fatty acid accumulation. In some embodiments, the increasing fatty acid accumulation comprises increasing $C_{16-18}$ fatty acid accumulation. In some embodiments, increasing lipid accumulation comprises increasing polyunsaturated fatty acid accumulation. In some embodiments, the increasing polyunsaturated fatty acid accumulation comprises increasing $C_{10-30}$ polyunsaturated fatty acid accumulation. In some embodiments, the increasing polyunsaturated fatty acid accumulation comprises increasing $C_{10-20}$ polyunsaturated fatty acid accumulation. In some embodiments, the increasing polyunsaturated fatty acid accumulation comprises increasing $C_{16-18}$ polyunsaturated fatty acid accumulation.

In some embodiments, the increasing lipid accumulation comprises increasing triacylglycerol accumulation. In some embodiments, the increasing triacylglycerol accumulation comprises increasing $C_{30-60}$ triacylglycerol accumulation. In some embodiments, the increasing triacylglycerol accumulation comprises increasing $C_{40-60}$ triacylglycerol accumulation. In some embodiments, the triacylglycerol comprises fatty acids of $C_{10-20}$ in chain length. In some embodiments, the triacylglycerol comprises fatty acids of $C_{15-20}$ in chain length. In some embodiments, the triacylglycerol comprises fatty acids of 16 carbons in chain length. In some embodiments, the triacylglycerol comprises fatty acids of 18 carbons in chain length. In some embodiments, the triacylglycerol comprises fatty acids of 16 carbons and 18 carbons in chain length.

In some embodiments, the increasing lipid accumulation comprises increasing fatty acid accumulation and increasing triacylglycerol accumulation. In some embodiments, the increasing lipid accumulation comprises increasing polyunsaturated fatty acid accumulation and increasing triacylglycerol accumulation.

In some embodiments, the method further comprises increasing carbohydrate accumulation in the cell. For example, the carbohydrate accumulation may be increased by about 1.1 to about 5 fold, from about 1.25 to about 5 fold, from about 1.5 to about 5 fold, from about 1.75 to about 5 fold, from about 2 to about 5 fold, from about 2.25 to about 5 fold, from about 2.5 to about 5 fold, from about 2.75 to about 5 fold, from about 3 to about 5 fold, from about 3.25 to about 5 fold, from about 3.5 to about 5 fold, from about 3.75 to about 5 fold, from about 4 to about 5 fold, from about 4.25 to about 5 fold, from about 4.5 to about 5 fold, or from about 4.75 to about 5 fold. In some embodiments, the method further comprises increasing carbohydrate accumulation in the cell by about 1.25 to about 3.25 fold. In some embodiments, the method further comprises increasing carbohydrate accumulation in the cell by about 1.25 fold. In some embodiments, the method further comprises increasing carbohydrate accumulation in the cell by about 2 fold. In some embodiments, the method further comprises increasing carbohydrate accumulation in the cell by about 3.2 fold.

In some embodiments, the method further comprises increasing carbohydrate production in the cell. For example, the carbohydrate production may be increased by about 1.1 to about 5 fold, from about 1.25 to about 5 fold, from about 1.5 to about 5 fold, from about 1.75 to about 5 fold, from about 2 to about 5 fold, from about 2.25 to about 5 fold, from about 2.5 to about 5 fold, from about 2.75 to about 5 fold, from about 3 to about 5 fold, from about 3.25 to about 5 fold, from about 3.5 to about 5 fold, from about 3.75 to about 5 fold, from about 4 to about 5 fold, from about 4.25 to about 5 fold, from about 4.5 to about 5 fold, or from about 4.75 to about 5 fold. In some embodiments, the method further comprises increasing carbohydrate production in the cell by about 1.25 to about 3.25 fold. In some embodiments, the method further comprises increasing carbohydrate production in the cell by about 1.25 fold. In some embodiments, the method further comprises increasing carbohydrate production in the cell by about 2 fold. In some embodiments, the method further comprises increasing carbohydrate production in the cell by about 3.2 fold.

In some embodiments, the method further comprises increasing carbohydrate accumulation in the cell and increasing carbohydrate production in the cell.

In some embodiments, the lipid accumulation is increased by greater than about 1.5 fold as compared to a cell that has not been contacted by the compound, for example, greater than about 1.5 fold, greater than about 2 fold, greater than about 2.5 fold, greater than about 3 fold, greater than about 3.5 fold, greater than about 4 fold, greater than about 4.5 fold, or greater than about 5 fold as compared to a cell that has not been contacted by the compound. In some embodiments, the lipid accumulation is increased by greater than about 2-fold as compared to a cell that has not been contacted by the compound. In some embodiments, the lipid accumulation is increased by greater than about 2.5-fold as compared to a cell that has not been contacted by the compound.

In some embodiments, the contacting the cell with the compound does not reduce the rate of cellular growth compared to a cell that has not been contacted by the compound.

In some embodiments, contacting the cell with the compound does not reduce the rate of photosynthesis of the cell compared to a cell that has not been contacted by the compound. For example, the rate of photosynthesis of the cell is not reduced if the amount of Chlorophyll A and B, carotenoid, and RuBisCO (Ribulose-1,5-bisphosphate carboxylase/oxygenase) in a cell contacted by a compound provided herein are about equivalent to a cell that has not been contacted by the compound. In some embodiments, the amount of Chlorophyll A and B, carotenoid, and RuBisCO (Ribulose-1,5-bisphosphate carboxylase/oxygenase) in a cell that has been contacted by a compound provided herein are about equivalent to a cell that has not been contacted by the compound.

In some embodiments, the contacting does not adversely affect the viability of the cell. For example, the viability of the cell may include, but is not limited to, cellular growth, total cellular protein levels, the level of Chlorophyll A in a cell, the level of Chlorophyll B in a cell, the level of carotenoid in a cell, the level of RuBisCO (Ribulose-1,5-bisphosphate carboxylase/oxygenase) in a cell, the level of carbohydrates in a cell, the level of nitrogen in a cell, the level of sulfur in a cell, and the level of metal content in a cell, or any combination thereof.

In some embodiments, the lipid accumulation is increased without exposing the cell to environmental stress. As used herein, the term "environmental stress" refers to a stress upon the cell that may result in a decrease or loss of cell viability. In some embodiments, the environmental stress comprises nutrient deprivation. In some embodiments, the environmental stress comprises depriving the cell of nitrogen, depriving the cell of sulfur, depriving the cell of metal, or any combination thereof.

The present application further provides a method of increasing lipid production in a cell, comprising contacting the cell with an effective amount of a compound provided herein (e.g. a compound of any one of Formulae I, Ia, Ib, Ic, II, IIa, III, and IIIa, or a pharmaceutically acceptable salt thereof). In some embodiments, the compound is a compound of Formula Ia, or a pharmaceutically acceptable salt thereof, or a compound of Formula Ib, or a pharmaceutically acceptable salt thereof, or a compound of Formula Ic, or a pharmaceutically acceptable salt thereof, or a compound of Formula IIa, or a pharmaceutically acceptable salt thereof, or a compound of Formula IIIa, or a pharmaceutically acceptable salt thereof. In some embodiments, the compound is a compound of Formula I, or a pharmaceutically acceptable salt thereof. In some embodiments, the compound is a compound of Formula II, or a pharmaceutically acceptable salt thereof. In some embodiments, the compound is a compound of Formula III, or a pharmaceutically acceptable salt thereof. In some embodiments, the compound is selected from the group of compounds provided in Table 1A, Table 1B, Table 1C, Table 2A, Table 3A, Table 4, Table 5, and Table 6, or a pharmaceutically acceptable salt thereof.

In some embodiments, the compound is selected from the group consisting of:
2-(3,4-dimethoxyphenyl)-N-methyl-N-(4-nitrobenzyl)
  ethan-1-amine;
N-methyl-N-(4-nitrobenzyl)cyclohexanamine;
3-(adamantan-1-yl(methyl)amino)propanenitrile;
1-(adamantan-2-yl)-4-(methylsulfonyl)piperazine;
4-((4-(2-methoxyphenyl)piperazin-1-yl)methyl)phenol;
(4-benzylpiperazin-1-yl)(2,3-dihydrobenzo[b] 1,4]dioxin-2-
  yl) methanone;
1-cinnamyl-4-(4-methoxybenzyl)piperazine;
1-(4-fluorobenzyl)-4-(o-tolyl)piperazine; and
1-benzyl-4-(bicyclo[2.2.1]heptan-2-yl)piperazine;
or a pharmaceutically acceptable salt thereof.

In some embodiments, the compound is selected from the group consisting of:
2-(3,4-dimethoxyphenyl)-N-methyl-N-(4-nitrobenzyl)
  ethan-1-amine;
N-methyl-N-(4-nitrobenzyl)cyclohexanamine;

3-(adamantan-1-yl(methyl)amino)propanenitrile hydrochloride;
1-(adamantan-2-yl)-4-(methylsulfonyl)piperazine;
4-((4-(2-methoxyphenyl)piperazin-1-yl)methyl)phenol;
(4-benzylpiperazin-1-yl)(2,3-dihydrobenzo[b] 1,4]dioxin-2-yl) methanone hydrochloride;
1-cinnamyl-4-(4-methoxybenzyl)piperazine;
1-(4-fluorobenzyl)-4-(o-tolyl)piperazine; and
1-benzyl-4-(bicyclo[2.2.1]heptan-2-yl)piperazine.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile hydrochloride).

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile hydrochloride).

In some embodiments, the cell is a eukaryotic cell or a cyanobacteria. In some embodiments, the cell is a eukaryotic cell. In some embodiments, the cell is a cyanobacteria. In some embodiments, the cell is selected from the group consisting of an algal cell, a *drosophila* cell, a yeast cell, or a fungus cell (e.g., an algal cell, a *drosophila* cell, a yeast cell, or a fungus cell provided herein).

In some embodiments, the cell is an algal cell. In some embodiments, the cell is selected from the group consisting of:
 *Chlamydomonas reinhardtii*;
 *Chlorella sorokiniana*;
 *Tetrachlorella alterans*;
 *C. protothecoides*;
 *C. vulgaris*; and
 *Nannochloropsis* sp.

In some embodiments, the cell is an algal cell. In some embodiments, the cell is selected from the group consisting of:
 *Chlamydomonas reinhardtii* CC125;
 *Chlorella sorokiniana* UTEX 1230;
 *Tetrachlorella alterans* UTEX 2453;
 *C. protothecoides*;
 *C. vulgaris* UTEX 395; and
 *Nannochloropsis* sp.

In some embodiments, the increasing lipid production comprises increasing fatty acid production. In some embodiments, the increasing fatty acid production comprises increasing $C_{10-30}$ fatty acid production. In some embodiments, the increasing fatty acid production comprises increasing $C_{10-20}$ fatty acid production. In some embodiments, the increasing fatty acid production comprises increasing $C_{16-18}$ fatty acid production. In some embodiments, increasing lipid production comprises increasing polyunsaturated fatty acid production. In some embodiments, the increasing polyunsaturated fatty acid production comprises increasing $C_{10-30}$ polyunsaturated fatty acid production. In some embodiments, the increasing polyunsaturated fatty acid production comprises increasing $C_{10-20}$ polyunsaturated fatty acid production. In some embodiments, the increasing polyunsaturated fatty acid production comprises increasing $C_{16-18}$ polyunsaturated fatty acid production.

In some embodiments, the increasing lipid production comprises increasing triacylglycerol production. In some embodiments, the increasing triacylglycerol production comprises increasing $C_{30-60}$ triacylglycerol production. In some embodiments, the increasing triacylglycerol production comprises increasing $C_{40-60}$ triacylglycerol production. In some embodiments, the triacylglycerol comprises fatty acids of $C_{10-20}$ in chain length. In some embodiments, the triacylglycerol comprises fatty acids of $C_{15-20}$ in chain length. In some embodiments, the triacylglycerol comprises fatty acids of 16 carbons in chain length. In some embodiments, the triacylglycerol comprises fatty acids of 18 carbons in chain length. In some embodiments, the triacylglycerol comprises fatty acids of 16 carbons and 18 carbons in chain length.

In some embodiments, the increasing lipid production comprises increasing fatty acid production and increasing triacylglycerol production. In some embodiments, the increasing lipid production comprises increasing polyunsaturated fatty acid production and increasing triacylglycerol production.

In some embodiments, the method further comprises increasing carbohydrate accumulation in the cell. For example, the carbohydrate accumulation may be increased by about 1.1 to about 5 fold, from about 1.25 to about 5 fold, from about 1.5 to about 5 fold, from about 1.75 to about 5 fold, from about 2 to about 5 fold, from about 2.25 to about 5 fold, from about 2.5 to about 5 fold, from about 2.75 to about 5 fold, from about 3 to about 5 fold, from about 3.25 to about 5 fold, from about 3.5 to about 5 fold, from about 3.75 to about 5 fold, from about 4 to about 5 fold, from about 4.25 to about 5 fold, from about 4.5 to about 5 fold, or from about 4.75 to about 5 fold. In some embodiments, the method further comprises increasing carbohydrate accumulation in the cell by about 1.25 to about 3.25 fold. In some embodiments, the method further comprises increasing carbohydrate accumulation in the cell by about 1.25 fold. In some embodiments, the method further comprises increasing carbohydrate accumulation in the cell by about 2 fold. In some embodiments, the method further comprises increasing carbohydrate accumulation in the cell by about 3.2 fold.

In some embodiments, the method further comprises increasing carbohydrate production in the cell. For example, the carbohydrate production may be increased by about 1.1 to about 5 fold, from about 1.25 to about 5 fold, from about 1.5 to about 5 fold, from about 1.75 to about 5 fold, from about 2 to about 5 fold, from about 2.25 to about 5 fold, from about 2.5 to about 5 fold, from about 2.75 to about 5 fold, from about 3 to about 5 fold, from about 3.25 to about 5 fold, from about 3.5 to about 5 fold, from about 3.75 to about 5 fold, from about 4 to about 5 fold, from about 4.25 to about 5 fold, from about 4.5 to about 5 fold, or from about 4.75 to about 5 fold. In some embodiments, the method further comprises increasing carbohydrate production in the cell by about 1.25 to about 3.25 fold. In some embodiments, the method further comprises increasing carbohydrate production in the cell by about 1.25 fold. In some embodiments, the method further comprises increasing carbohydrate production in the cell by about 2 fold. In some embodiments, the method further comprises increasing carbohydrate production in the cell by about 3.2 fold.

In some embodiments, the method further comprises increasing carbohydrate accumulation in the cell and increasing carbohydrate production in the cell.

In some embodiments, the lipid production is increased by greater than about 1.5 fold as compared to a cell that has not been contacted by the compound, for example, greater than about 1.5 fold, greater than about 2 fold, greater than about 2.5 fold, greater than about 3 fold, greater than about 3.5 fold, greater than about 4 fold, greater than about 4.5 fold, or greater than about 5 fold as compared to a cell that has not been contacted by the compound. In some embodiments, the lipid production is increased by greater than about 2-fold as compared to a cell that has not been contacted by the compound. In some embodiments, the lipid production is increased by greater than about 2.5-fold as compared to a cell that has not been contacted by the compound.

In some embodiments, the contacting the cell with the compound does not reduce the rate of cellular growth compared to a cell that has not been contacted by the compound.

In some embodiments, contacting the cell with the compound does not reduce the rate of photosynthesis of the cell compared to a cell that has not been contacted by the compound. For example, the rate of photosynthesis of the cell is not reduced if the amount of Chlorophyll A and B, carotenoid, and RuBisCO (Ribulose-1,5-bisphosphate carboxylase/oxygenase) in a cell contacted by a compound provided herein are about equivalent to a cell that has not been contacted by the compound. In some embodiments, the amount of Chlorophyll A and B, carotenoid, and RuBisCO (Ribulose-1,5-bisphosphate carboxylase/oxygenase) in a cell that has been contacted by a compound provided herein are about equivalent to a cell that has not been contacted by the compound.

In some embodiments, the contacting does not adversely affect the viability of the cell. For example, the viability of the cell may include, but is not limited to, cellular growth, total cellular protein levels, the level of Chlorophyll A in a cell, the level of Chlorophyll B in a cell, the level of carotenoid in a cell, the level of RuBisCO (Ribulose-1,5-bisphosphate carboxylase/oxygenase) in a cell, the level of carbohydrates in a cell, the level of nitrogen in a cell, the level of sulfur in a cell, and the level of metal content in a cell, or any combination thereof.

In some embodiments, the lipid production is increased without exposing the cell to environmental stress. In some embodiments, the environmental stress comprises nutrient deprivation. In some embodiments, the environmental stress comprises depriving the cell of nitrogen, depriving the cell of sulfur, depriving the cell of metal, or any combination thereof.

The present application further provides a method of producing biofuel, the method comprising:
a) contacting a cell with an effective amount of a compound provided herein (e.g., a compound of any one of Formulae I, Ia, Ib, Ic, II, IIa, III, and IIIa, or a pharmaceutically acceptable salt thereof);
b) waiting a time sufficient to allow for increased lipid accumulation; and
c) processing the cells into biofuel.

In some embodiments, the compound is a compound of Formula Ia, or a pharmaceutically acceptable salt thereof, or a compound of Formula Ib, or a pharmaceutically acceptable salt thereof, or a compound of Formula Ic, or a pharmaceutically acceptable salt thereof, or a compound of Formula IIa, or a pharmaceutically acceptable salt thereof, or a compound of Formula IIIa, or a pharmaceutically acceptable salt thereof. In some embodiments, the compound is a compound of Formula I, or a pharmaceutically acceptable salt thereof. In some embodiments, the compound is a compound of Formula II, or a pharmaceutically acceptable salt thereof. In some embodiments, the compound is a compound of Formula III, or a pharmaceutically acceptable salt thereof. In some embodiments, the compound is selected from the group of compounds provided in Table 1A, Table 1B, Table 1C, Table 2A, Table 3A, Table 4, Table 5, and Table 6, or a pharmaceutically acceptable salt thereof.

In some embodiments, the compound is selected from the group consisting of:
2-(3,4-dimethoxyphenyl)-N-methyl-N-(4-nitrobenzyl) ethan-1-amine;
N-methyl-N-(4-nitrobenzyl)cyclohexanamine;
3-(adamantan-1-yl(methyl)amino)propanenitrile;
1-(adamantan-2-yl)-4-(methylsulfonyl)piperazine;
4-((4-(2-methoxyphenyl)piperazin-1-yl)methyl)phenol;
(4-benzylpiperazin-1-yl)(2,3-dihydrobenzo[b] 1,4]dioxin-2-yl) methanone;
1-cinnamyl-4-(4-methoxybenzyl)piperazine;
1-(4-fluorobenzyl)-4-(o-tolyl)piperazine; and
1-benzyl-4-(bicyclo[2.2.1]heptan-2-yl)piperazine;
or a pharmaceutically acceptable salt thereof.

In some embodiments, the compound is selected from the group consisting of:
2-(3,4-dimethoxyphenyl)-N-methyl-N-(4-nitrobenzyl) ethan-1-amine;
N-methyl-N-(4-nitrobenzyl)cyclohexanamine;
3-(adamantan-1-yl(methyl)amino)propanenitrile hydrochloride;
1-(adamantan-2-yl)-4-(methylsulfonyl)piperazine;
4-((4-(2-methoxyphenyl)piperazin-1-yl)methyl)phenol;
(4-benzylpiperazin-1-yl)(2,3-dihydrobenzo[b] 1,4]dioxin-2-yl) methanone hydrochloride;
1-cinnamyl-4-(4-methoxybenzyl)piperazine;
1-(4-fluorobenzyl)-4-(o-tolyl)piperazine; and
1-benzyl-4-(bicyclo[2.2.1]heptan-2-yl)piperazine.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile hydrochloride).

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile;
or a pharmaceutically acceptable salt thereof.

In some embodiments, the compound is selected from the group consisting of:
(2-(3,4-dimethoxyphenyl)-N-methyl-N-(4-nitrobenzyl) ethan-1-amine);
(4-((4-(2-methoxyphenyl)piperazin-1-yl)methyl)phenol); and
(3-(adamantan-1-yl(methyl)amino)propanenitrile hydrochloride).

In some embodiments, the cell is a eukaryotic cell or a cyanobacteria. In some embodiments, the cell is a eukaryotic cell. In some embodiments, the cell is a cyanobacteria. In some embodiments, the cell is selected from the group consisting of an algal cell, a *drosophila* cell, a yeast cell, or a fungus cell (e.g., an algal cell, a *drosophila* cell, a yeast cell, or a fungus cell provided herein).

In some embodiments, the cell is an algal cell. In some embodiments, the cell is selected from the group consisting of:
*Chlamydomonas reinhardtii;*
*Chlorella sorokiniana;*
*Tetrachlorella alterans;*
*C. protothecoides;*
*C. vulgaris;* and
*Nannochloropsis* sp.

In some embodiments, the cell is an algal cell. In some embodiments, the cell is selected from the group consisting of:
*Chlamydomonas reinhardtii* CC125;
*Chlorella sorokiniana* UTEX 1230;
*Tetrachlorella alterans* UTEX 2453;
*C. protothecoides;*
*C. vulgaris* UTEX 395; and
*Nannochloropsis* sp.

In some embodiments, the time sufficient to allow for increased lipid accumulation is from about 1 hour to about 5 days, for example, from about 1 hour to about 5 days, from about 1 hour to about 4 days, from about 1 hour to about 3 days, from about 1 hour to about 2 days, from about 1 hour to about 1 day, from about 1 hour to about 18 hours, from about 1 hour to about 12 hours, from about 1 hour to about 6 hours, from about 1 hour to about 2 hours, from about 2 hours to about 4 days, from about 2 hours to about 3 days, from about 2 hours to about 2 days, from about 2 hours to about 1 day, from about 2 hours to about 18 hours, from about 2 hours to about 12 hours, from about 2 hours to about 6 hours, from about 6 hours to about 4 days, from about 6 hours to about 3 days, from about 6 hours to about 2 days, from about 6 hours to about 1 day, from about 6 hours to about 18 hours, from about 6 hours to about 12 hours, from about 12 hours to about 4 days, from about 12 hours to about 3 days, from about 12 hours to about 2 days, from about 12 hours to about 1 day, from about 12 hours to about 18 hours, from about 18 hours to about 4 days, from about 18 hours to about 3 days, from about 18 hours to about 2 days, from about 18 hours to about 1 day, from about 1 day to about 4 days, from about 1 day to about 3 days, from about 1 day to about 2 days, from about 2 days to about 4 days, from about 2 days to about 3 days, or from about 3 days to about 4 days. In some embodiments, the time sufficient to allow for increased lipid accumulation is about 1 day. In some embodiments, the time sufficient to allow for increased lipid accumulation is about 2 days. In some embodiments, the time sufficient to allow for increased lipid accumulation is about 3 days.

Methods of processing cells into biofuel are known in the art and would be readily understood by one of ordinary skill. For example, the cells may be processed into biofuels selected from the group consisting of biodiesel, bioalcohol (e.g., bioethanol, biopropanol, biobutanol), and cellulosic ethanol. Examples of methods for processing cells into biofuel may be found, e.g., in Pandey et al., *Biofuels from Algae*, 1$^{st}$ Ed., Elsevier B. V. (2014), the disclosure of which is incorporated herein in its entirety.

The present application further provides a nutraceutical comprising one or more lipids produced according to a method provided herein. In some embodiments, the one or more lipids is produced in a cell provided herein, wherein the cell has been contacted with a compound provided herein (e.g., a compound of any one of Formulae I, Ia, Ib, Ic, II, IIa, III, and IIIa, or a pharmaceutically acceptable salt thereof). In some embodiments, the lipid is docosahexaenoic acid (DHA). In some embodiments, the nutraceutical is formulated for oral administration, for example, as a pill, a tablet, a syrup, a drink, and the like.

Definitions

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkenylene", employed alone or in combination with other terms, refers to a divalent alkenyl linking group having n to m carbons. Examples of alkenylene groups include, but are not limited to, —CH=CH—, —CH=CHCH$_2$—, —CH$_2$CH$_2$CH=CHCH$_2$, and the like. In some embodiments, the alkylene moiety contains 2 to 6, 2 to 4, or 2 to 3 carbon atoms.

As used herein, the term "$C_{n-m}$ alkoxy", employed alone or in combination with other terms, refers to a group of formulae "—O-alkyl", or "—(O-alkylene)$_p$-", or "-(alkylene-O)$_p$—". wherein the alkyl or alkylene group has n to m carbons and p is an integer from 1 to 6. Example alkoxy groups include methoxy, ethoxy, propoxy (e.g., n-propoxy and isopropoxy), tert-butoxy, —(CH$_2$OCH$_2$OCH$_2$)—, —(CH$_2$CH$_2$OCH$_2$CH$_2$O)—, —(OCH$_2$)—, —(OCH$_2$OCH$_2$CH$_2$)—, —(CH$_2$CH$_2$OCH$_2$CH$_2$O)—, —(CH$_2$CH$_2$OCH$_2$CH$_2$OCH$_2$CH$_2$)— and the like. In some embodiments, the alkyl group has 1 to 6, 1 to 4, or 1 to 3 carbon atoms. In some embodiments, p is 1. In some embodiments, p is 2. In some embodiments, p is 3. In some embodiments, p is 4. In some embodiments, p is 5. In some embodiments, p is 6.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n\text{-}m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, a halo is F, Cl, or Br.

As used herein, the term "$C_{n\text{-}m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3\text{-}10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 5-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-13 ring atoms and 1, 2, 3 or 4 heteroatom ring members independently selected from nitrogen, sulfur and oxygen. For example, a five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring, for example, is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-10 membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1, 2, or 3 ring heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use,* Wiley-VCH, 2002.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. High Throughput Screening Assay

A large scale in vivo high throughput screen (HTS) was performed to identify small compounds that stimulate lipid production and accumulation using the model organism *Chlamydomonas reinhardtii.* The HTS employed a 384-well microplate format in which cells were allowed to grow in the presence of the test compounds at 10 μM final concentration for 72 hours. Accumulation of intracellular lipids was assessed using the lipophilic dye Nile Red to select high lipid producers and growth was monitored at $OD_{600}$ to select compounds that did not eliminate cellular growth.

The screening library included 43,736 compounds (ChemBridge, Corp). A total of 367 active compounds were identified that stimulated lipid accumulation to >2.5-fold and did not affect cell viability. A sub-set of compounds were retested using an 8-point dose response assay (0.25-30 μM). Compounds were further assessed visually using a Nikon Ti-inverted microscope (60×) to reconfirm lipid droplet accumulation was induced. The $EC_{50}$ (μM) values and microscopy images of compounds 1, 62, and 136 are shown in FIG. 1. Treatment of the cells with compounds 1, 62, and 136 does not disrupt major organelles including nucleus, endoplasmic reticulum, and chloroplast (FIG. 1).

Table 7 shows results of the 8-point dose response assay.

TABLE 7

| | Dose Response Assay | | | | | | | |
|---|---|---|---|---|---|---|---|---|
| | 30 μM | 15 μM | 10 μM | 5 μM | 2.5 μM | 1.25 μM | 0.625 μM | 0.25 μM |
| 1 | 21.1 | 15.48 | 4.46 | 9.79 | 3.08 | 1.43 | 1.01 | 0.84 |
| 2 | 2.11 | 1.34 | 1.53 | 1.1 | 0.99 | 0.94 | 1.01 | 0.96 |
| 3 | 10.85 | 3.96 | 2.39 | 2.15 | 1.69 | 1.19 | 0.99 | 0.92 |
| 4 | 4.75 | 10.37 | 10.31 | 10.65 | 11.42 | 10.05 | 1.8 | 0.94 |
| 5 | 2.81 | 1.96 | 2.07 | 1.28 | 0.91 | 0.80 | 0.85 | 0.97 |
| 6 | 15.14 | 17.67 | 7.75 | 9.91 | 3.31 | 1.99 | 1.51 | 0.94 |
| 7 | 7.55 | 9.14 | 7.39 | 10.8 | 9.26 | 8.75 | 8.84 | 7 |
| 8 | 5.94 | 13.62 | 9.43 | 12.88 | 3.48 | 1.57 | 1.07 | 1.02 |
| 9 | 9.66 | 11.32 | 6.34 | 9.14 | 5.29 | 4.88 | 7.65 | 3.47 |
| 11 | 1.78 | 2.28 | 2.78 | 1.46 | 0.93 | 0.97 | 1.12 | 1.02 |
| 12 | 7.51 | 5.88 | 3.39 | 5.03 | 1.36 | 0.85 | 0.78 | 1.19 |
| 13 | 6.01 | 4.05 | 7.68 | 7.65 | 10.91 | 9.67 | 2.46 | 1.17 |

TABLE 7-continued

| Dose Response Assay | | | | | | | | |
|---|---|---|---|---|---|---|---|---|
| | 30 µM | 15 µM | 10 µM | 5 µM | 2.5 µM | 1.25 µM | 0.625 µM | 0.25 µM |
| 14 | 13.04 | 16.13 | 8.91 | 11.61 | 4.45 | 11.44 | 3.73 | 1.39 |
| 15 | 14.89 | 7.24 | 10.5 | 10.92 | 3.11 | 1.39 | 1.02 | 0.92 |
| 16 | 2.95 | 2.7 | 2.78 | 11.47 | 10.51 | 2.5 | 1.36 | 0.99 |
| 17 | 1.67 | 1.04 | 0.92 | 1.07 | 0.89 | 0.89 | 1.03 | 1.09 |
| 18 | 1.29 | 1.31 | 1.19 | 1.17 | 1.13 | 0.89 | 0.97 | 1.01 |
| 19 | 7.47 | 15.55 | 9.8 | 10.55 | 9.13 | 3.4 | 2.2 | 2.39 |
| 20 | 5.51 | 4.02 | 2.85 | 10.58 | 13.55 | 11.38 | 2.97 | 1.15 |
| 21 | 2.91 | 5.67 | 4.65 | 9.6 | 7.76 | 3.64 | 4.2 | 1.63 |
| 22 | 4.28 | 8.64 | 7.47 | 12.27 | 7.88 | 6.68 | 2.51 | 2.53 |
| 23 | 1.15 | 1.43 | 1.1 | 1.04 | 0.78 | 0.79 | 1 | 1.02 |
| 24 | 1.25 | 1.19 | 1.18 | 0.99 | 0.97 | 0.84 | 0.87 | 1.13 |
| 25 | 1.34 | 1.33 | 1 | 1 | 1.02 | 0.99 | 1.13 | 1.15 |
| 26 | 2.94 | 4.06 | 6.43 | 12.5 | 3.9 | 1.03 | 0.97 | 1.08 |
| 27 | 5.68 | 3.65 | 3.57 | 12.11 | 14.97 | 1.86 | 1.22 | 1.17 |
| 28 | 13.49 | 19.07 | 7.39 | 11.25 | 9.91 | 4.38 | 5.73 | 3.06 |
| 29 | 17.22 | 20.41 | 7.81 | 8.14 | 2.38 | 2.19 | 1.43 | 0.81 |
| 30 | 1.73 | 1.37 | 0.82 | 0.99 | 0.84 | 1.16 | 1.05 | 1.15 |
| 31 | 17.01 | 15.24 | 3.34 | 4.4 | 3.61 | 1.68 | 0.92 | 0.86 |
| 32 | 7.09 | 8.09 | 3.63 | 4.84 | 2.51 | 0.95 | 0.78 | 0.93 |
| 33 | 7.79 | 10.01 | 4 | 1.58 | 1.18 | 0.81 | 0.89 | 0.82 |
| 34 | 2.35 | 3.78 | 3.65 | 10.44 | 3.5 | 1.84 | 1.01 | 0.93 |
| 35 | 2.51 | 2.5 | 2.65 | 1.91 | 1.96 | 1.23 | 1.49 | 1.09 |
| 36 | 5.31 | 8.49 | 2.72 | 3.47 | 1.89 | 1.95 | 0.94 | 0.93 |
| 37 | 1.15 | 1.16 | 1.76 | 1.93 | 1.85 | 1.39 | 0.97 | 1.04 |
| 38 | 2 | 2.61 | 2.94 | 2.64 | 2.23 | 1.23 | 1.38 | 1.06 |
| 39 | 1.38 | 1.57 | 0.88 | 1.18 | 1.18 | 0.99 | 1.13 | 1.17 |
| 40 | 15.88 | 17.74 | 4.07 | 3.53 | 3.94 | 2.25 | 1.26 | 1.06 |
| 41 | 7.43 | 7.85 | 8.37 | 15.71 | 3.33 | 1 | 0.99 | 1.01 |
| 42 | 7.26 | 6.28 | 4.24 | 11.32 | 6 | 10.94 | 10.42 | 2.01 |
| 43 | 12.59 | 14.28 | 5.78 | 8.39 | 7.57 | 9.14 | 9.13 | 2.35 |
| 44 | 10.81 | 13.88 | 2.68 | 5.1 | 1.82 | 0.95 | 1.01 | 1.05 |
| 45 | 1.56 | 2.06 | 2.02 | 3.61 | 2.3 | 1.57 | 0.99 | 0.93 |
| 46 | 1.78 | 2.63 | 2.75 | 2.31 | 1.61 | 0.94 | 0.96 | 1.23 |
| 47 | 1.19 | 1.27 | 1.37 | 0.95 | 1.3 | 0.91 | 0.81 | 0.90 |
| 48 | 6.94 | 10.55 | 4.43 | 8.42 | 1.69 | 0.75 | 0.66 | 0.80 |
| 49 | 3.07 | 8.51 | 8.98 | 10.46 | 2.42 | 1.94 | 0.93 | 1.15 |
| 50 | 13.02 | 8.62 | 7.3 | 10.74 | 3.25 | 0.90 | 1.19 | 1.1 |
| 51 | 11.93 | 13.34 | 6.57 | 9.13 | 3.34 | 3.47 | 3.9 | 1.09 |
| 52 | 11.4 | 10.15 | 9.09 | 7.75 | 6.48 | 0.91 | 0.92 | 1.12 |
| 53 | 2.49 | 1.61 | 1.57 | 1.42 | 1.1 | 1.13 | 1.38 | 1.06 |
| 54 | 1.58 | 1.78 | 1.73 | 2.79 | 2.32 | 2.13 | 1.53 | 1.05 |
| 55 | 2.77 | 2.26 | 2.04 | 2.23 | 2.27 | 2.01 | 1.77 | 1.3 |
| 56 | 1.92 | 1.74 | 2.71 | 2.58 | 1.8 | 1.34 | 1.2 | 1.2 |
| 57 | 1.87 | 1.15 | 1.11 | 1.28 | 0.90 | 1.01 | 1.06 | 0.99 |
| 58 | 1.56 | 1.42 | 1.15 | 1.22 | 0.90 | 1.14 | 0.94 | 1.06 |
| 59 | 3.84 | 3.04 | 2.52 | 2.54 | 2.18 | 2.02 | 1.91 | 1.28 |
| 60 | 1.65 | 1.35 | 1.4 | 1.22 | 1.1 | 1 | 1.07 | 1.07 |
| 61 | 1.14 | 1.24 | 0.91 | 1.04 | 0.95 | 0.92 | 0.96 | 0.90 |
| 62 | 21.07 | 19.19 | 8.95 | 10.44 | 8.17 | 3.11 | 3.12 | 1.05 |
| 63 | 21.78 | 20.48 | 10.18 | 9.63 | 3.92 | 2.53 | 1.61 | 0.98 |
| 64 | 7.98 | 3.48 | 7.63 | 10.61 | 10.14 | 7.72 | 11.51 | 5.81 |
| 65 | 8.07 | 11.17 | 8.09 | 9.72 | 5.42 | 3.84 | 2.04 | 1.03 |
| 66 | 5.72 | 4.89 | 5.36 | 9.73 | 12.08 | 9.49 | 4.1 | 1.31 |
| 67 | 3.6 | 6.33 | 7.75 | 10.08 | 13.05 | 3.09 | 2.29 | 1 |
| 68 | 2.03 | 2.74 | 1.95 | 2.1 | 2.15 | 1.28 | 1.05 | 1.07 |
| 69 | 2.54 | 3.49 | 3.49 | 2.44 | 3.01 | 1.29 | 0.96 | 1.05 |
| 70 | 11.07 | 11.05 | 7.57 | 8.64 | 4.4 | 2.19 | 1.55 | 0.87 |
| 71 | 11.83 | 12.08 | 8.37 | 7.95 | 2.29 | 1.22 | 1.15 | 0.89 |
| 72 | 9.85 | 10.08 | 9.28 | 2.81 | 2.21 | 0.99 | 1.03 | 1.22 |
| 74 | 2.81 | 1.96 | 2.07 | 1.28 | 0.91 | 0.80 | 0.85 | 0.97 |
| 75 | 6.95 | 2.89 | 2.35 | 2.25 | 2.08 | 1.22 | 1.02 | 0.90 |
| 76 | 10.01 | 11.14 | 8.88 | 5.17 | 10.31 | 8.1 | 8.99 | 2.09 |
| 77 | 4.05 | 10.93 | 2.78 | 2.28 | 10.74 | 2.6 | 1.41 | 1.06 |
| 78 | 7.85 | 10.45 | 9.94 | 8.34 | 10.24 | 1.64 | 1.41 | 0.83 |
| 79 | 16.86 | 15.62 | 8.1 | 9.69 | 6.13 | 1.83 | 1.08 | 0.87 |
| 81 | 18.89 | 18.42 | 3.75 | 3.32 | 1.97 | 0.88 | 0.85 | 0.91 |
| 82 | 13.39 | 17.76 | 8.09 | 10.46 | 7.09 | 8.56 | 8.43 | 4.74 |
| 83 | 8.83 | 15.98 | 6.89 | 1.14 | 1.01 | 0.76 | 0.79 | 0.98 |
| 84 | 1.34 | 2.19 | 1.64 | 2.05 | 2.5 | 1 | 0.89 | 0.92 |
| 86 | 3.76 | 3.38 | 2.71 | 2.29 | 2.39 | 1.69 | 1.01 | 0.98 |
| 88 | 4.8 | 15.2 | 8.16 | 10.2 | 8.96 | 4.98 | 2.14 | 1.04 |
| 90 | 8.7 | 13.43 | 6.74 | 8.56 | 6.5 | 2.86 | 8.53 | 2.39 |
| 91 | 8.29 | 16.37 | 6.76 | 10.52 | 11.82 | 2.82 | 1.37 | 0.95 |
| 93 | 8.86 | 12.09 | 8.59 | 7.33 | 3.6 | 1.49 | 0.96 | 0.97 |
| 94 | 6.35 | 11.58 | 9.97 | 16.62 | 11.42 | 10.23 | 10.57 | 5.93 |
| 95 | 1.81 | 1.74 | 4.03 | 14.02 | 10.7 | 1.78 | 1.5 | 1.03 |

TABLE 7-continued

Dose Response Assay

| | 30 µM | 15 µM | 10 µM | 5 µM | 2.5 µM | 1.25 µM | 0.625 µM | 0.25 µM |
|---|---|---|---|---|---|---|---|---|
| 96 | 11.77 | 17.34 | 10.03 | 10.24 | 6.91 | 3.17 | 1.51 | 0.87 |
| 97 | 8.76 | 7.56 | 3.46 | 9.14 | 3.15 | 3.67 | 3.14 | 1.1 |
| 98 | 11.04 | 10.69 | 8.92 | 3.28 | 3.5 | 2.25 | 1.57 | 1.39 |
| 99 | 4.22 | 3.37 | 2.96 | 1.96 | 1.4 | 0.97 | 0.84 | 0.98 |
| 100 | 18.12 | 9.57 | 3.77 | 3.04 | 2.26 | 1.12 | 0.95 | 1 |
| 101 | 1.75 | 1.43 | 1.04 | 1.58 | 0.88 | 1.14 | 1.08 | 1.03 |
| 103 | 9.86 | 10.84 | 5.85 | 1.17 | 1.1 | 0.94 | 0.85 | 0.99 |
| 104 | 3.69 | 3.28 | 2.81 | 4.04 | 5.27 | 3.96 | 3.68 | 1.23 |
| 106 | 9.7 | 12.36 | 5.08 | 6.74 | 3.68 | 2.46 | 2.12 | 1.02 |
| 107 | 3.06 | 3.07 | 2.48 | 2.31 | 2.05 | 1.23 | 1.01 | 0.98 |
| 109 | 9.73 | 12.09 | 5.27 | 5.91 | 6.87 | 2.89 | 1.93 | 1.42 |
| 110 | 12.43 | 14.61 | 7.3 | 3.69 | 3.61 | 3.52 | 1.76 | 0.89 |
| 111 | 9.13 | 12.3 | 6.41 | 8.78 | 7.07 | 8.14 | 2.59 | 1.04 |
| 112 | 10.17 | 7.57 | 12.3 | 12.95 | 3.53 | 1.3 | 0.86 | 0.86 |
| 113 | 3.03 | 4.24 | 5.96 | 11.79 | 11.03 | 10.63 | 2.27 | 1.15 |
| 120 | 1.02 | 3.19 | 2.15 | 1.07 | 1.12 | 0.89 | 0.64 | 0.91 |
| 121 | 12.49 | 11.68 | 5.87 | 9.06 | 1.93 | 3.47 | 1.31 | 0.92 |
| 123 | 1.83 | 3.09 | 3.7 | 4.8 | 10.38 | 7.48 | 4.34 | 1.86 |
| 124 | 1.38 | 1.57 | 0.88 | 1.18 | 1.18 | 0.99 | 1.13 | 1.17 |
| 129 | 14.66 | 14.1 | 3.85 | 15.81 | 12.76 | 2.18 | 1.34 | 0.95 |
| 130 | 7.38 | 15.13 | 6.34 | 4.88 | 1.03 | 0.94 | 0.96 | 1.13 |
| 131 | 1.87 | 4.36 | 9.13 | 3.8 | 1.66 | 1.08 | 1.02 | 0.99 |
| 132 | 4.57 | 5.24 | 2.62 | 2.87 | 1.91 | 1.16 | 1.19 | 1.02 |
| 133 | 3.44 | 14.41 | 9.72 | 12.58 | 7.4 | 2.81 | 2.02 | 1 |
| 134 | 2.14 | 1.97 | 1.31 | 1.77 | 1.32 | 0.93 | 1.06 | 0.97 |
| 135 | 11.19 | 16.64 | 10.02 | 9.84 | 2.47 | 1.09 | 0.88 | 0.86 |
| 136 | 19.83 | 18.82 | 8.7 | 12.81 | 3.51 | 1.82 | 1.32 | 0.88 |
| 137 | 4.85 | 12.33 | 7.15 | 10.2 | 2.77 | 3.13 | 1.91 | 1.09 |
| 138 | 12.1 | 16.27 | 9.72 | 9.85 | 2.75 | 3.51 | 2.28 | 1.09 |
| 139 | 2.8 | 6.14 | 3.04 | 2.27 | 2.68 | 0.86 | 1.09 | 1.18 |
| 140 | 7.63 | 5.97 | 4.8 | 3.05 | 1.26 | 1.1 | 1.33 | 0.98 |
| 141 | 4.1 | 3.53 | 4.5 | 13.19 | 11.63 | 9.16 | 3.57 | 1.39 |
| 142 | 7.36 | 4 | 6.3 | 6.53 | 10.4 | 10.17 | 13.32 | 9.79 |
| 143 | 14.27 | 17.97 | 9.99 | 9.45 | 9.14 | 2.68 | 1.39 | 0.85 |
| 144 | 19.74 | 22.79 | 11.58 | 12.44 | 10.13 | 4.03 | 1.64 | 0.86 |
| 145 | 11.88 | 13.65 | 7.27 | 8.15 | 7.77 | 9.73 | 2.56 | 0.81 |
| 146 | 6.76 | 5.68 | 6.61 | 4.14 | 4.38 | 1.93 | 1.3 | 1.01 |
| 147 | 2.84 | 3.72 | 5.17 | 9.42 | 11.21 | 9.71 | 11.86 | 2.58 |
| 148 | 1.45 | 1.65 | 1.39 | 1.63 | 1.32 | 0.88 | 1.04 | 0.94 |
| 149 | 8.77 | 16.41 | 3.82 | 5.3 | 3.45 | 1.18 | 0.84 | 0.84 |

Example 2. Cellular Growth

Figure 2B:
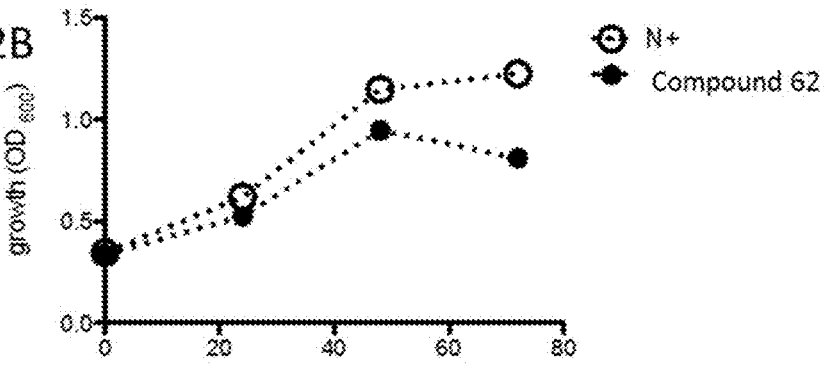
Figure 2C:
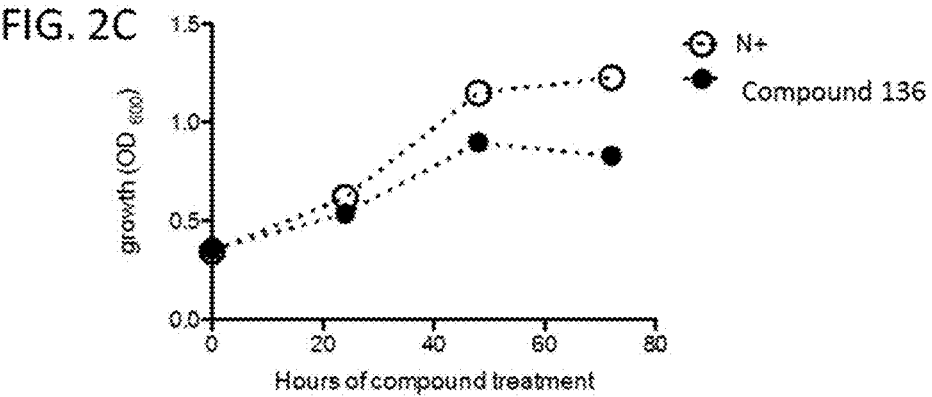

*Chlamydomonas reinhardtii* cells were grown in the presence of DMSO (control) or 30 µM of test compound for 72 hours. At the indicated times 200 µL cells were removed from each well and optical density and nile red fluorescence were measured. Results of the algal cell growth study are shown in FIG. 2A-2C.

Example 3. Lipid Accumulation

Figure 3:
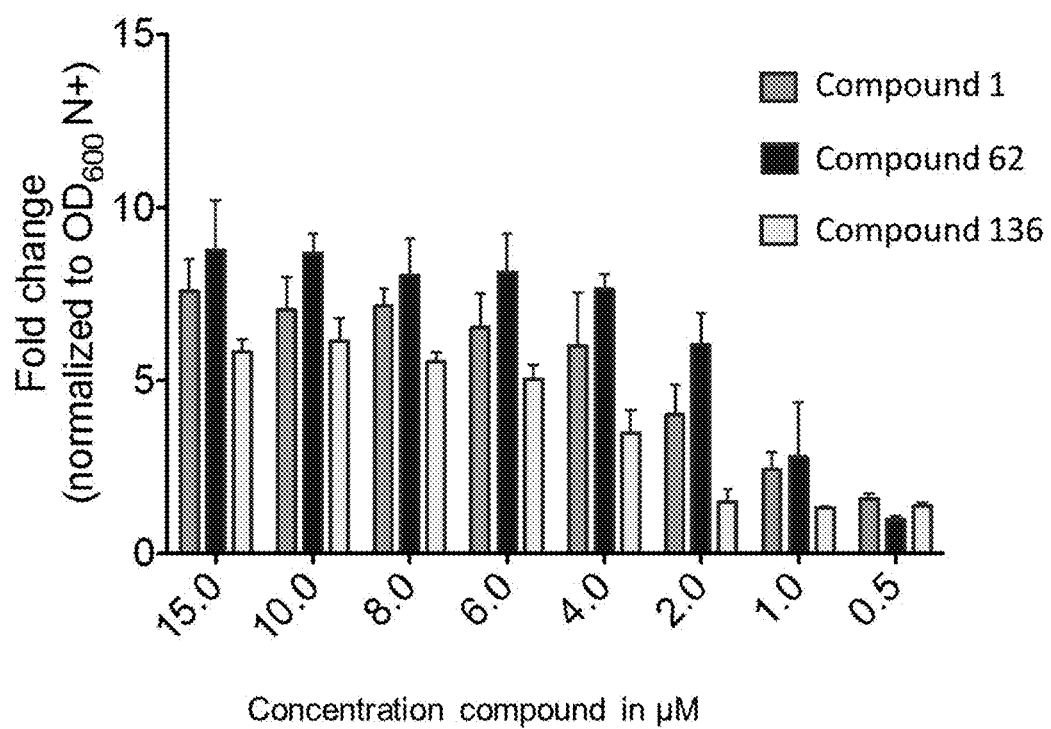
FIG. 3 shows increased lipid accumulation in cells in the presence of compounds 1, 62, and 136.
Figure 4:
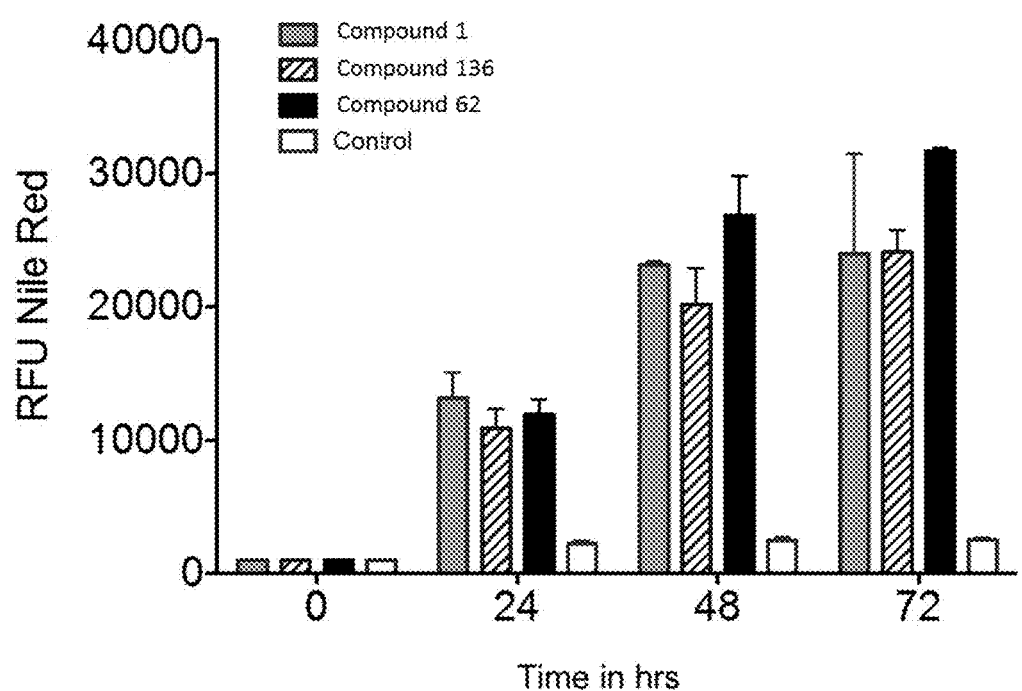
FIG. 4 shows increased lipid accumulation in cells over 72 hours in the presence of compounds 1, 62, and 136.
Figure 5:
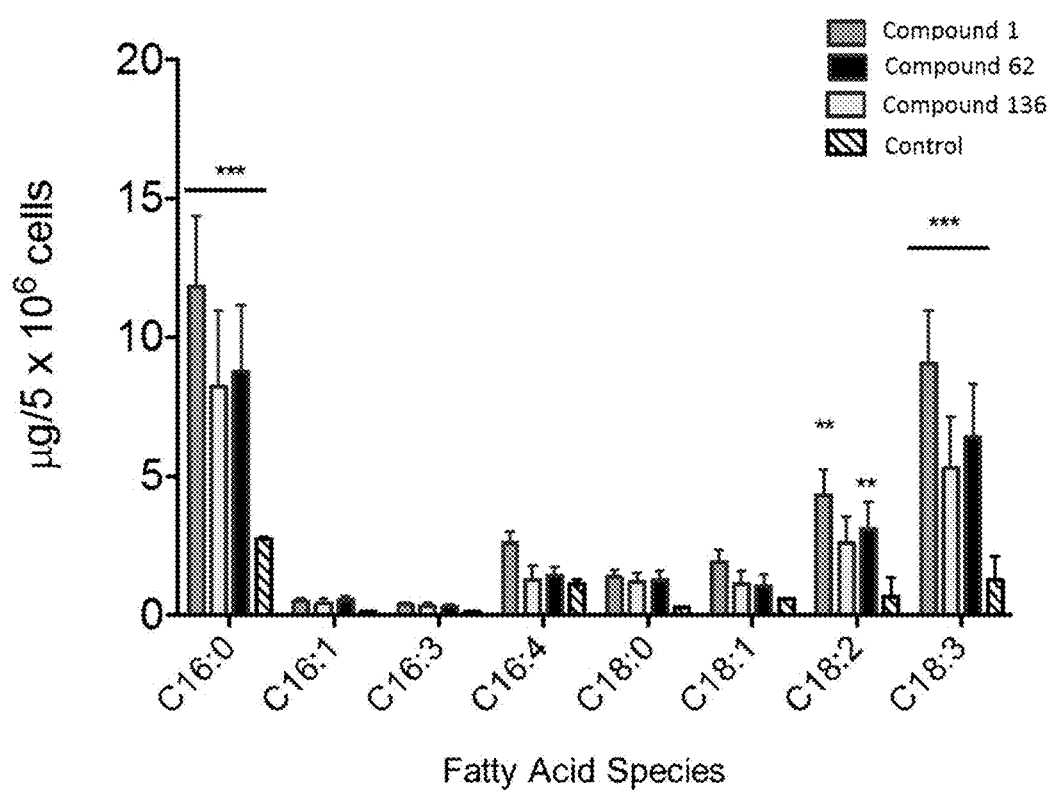
FIG. 5 shows increased fatty acid levels in cells in the presence of compounds 1, 62, and 136.
Figure 6:
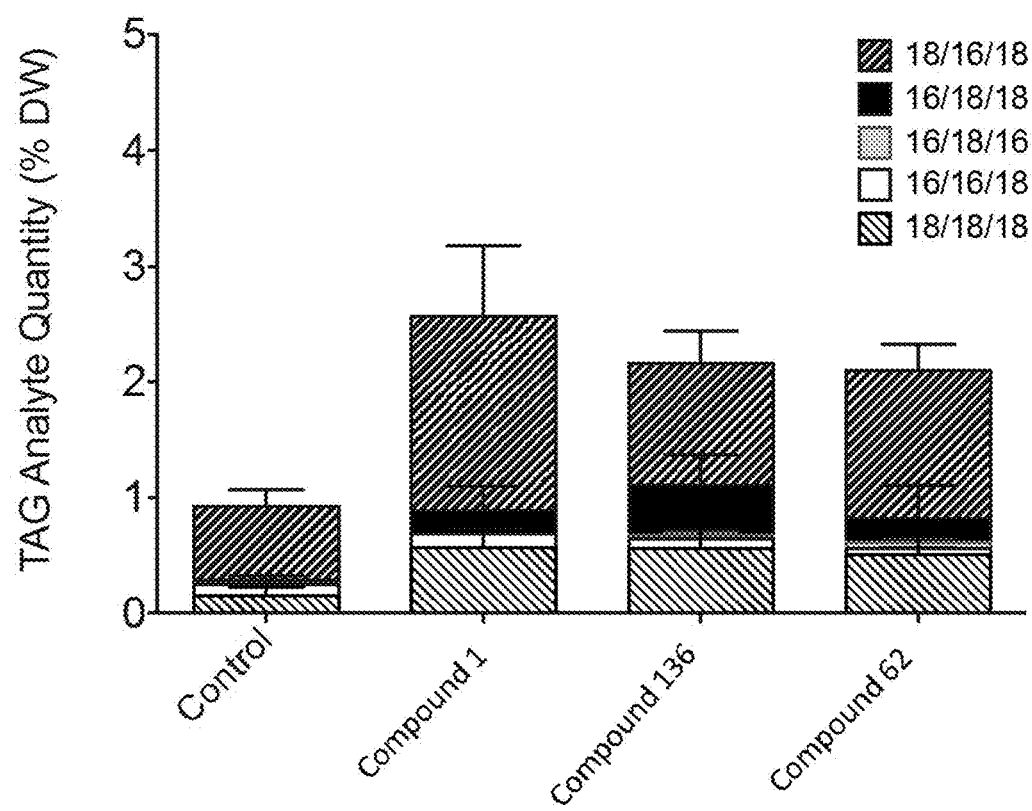
FIG. 6 shows increased triacylglyercol levels in cells in the presence of compounds 1, 62, and 136.
Figure 12A:
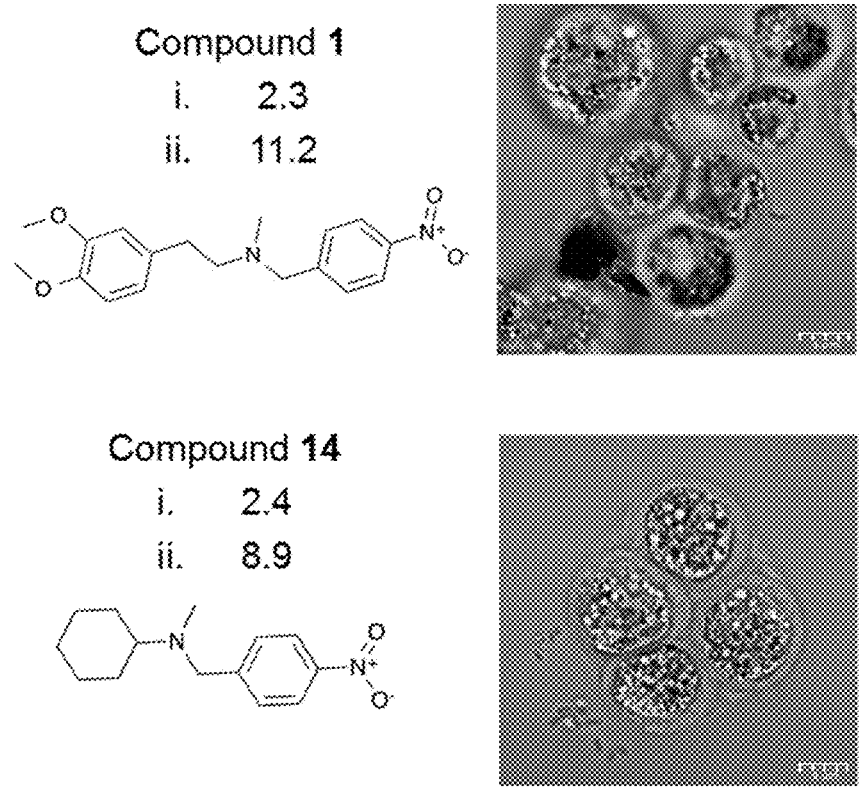
FIGS. 12A-12C show lipid body accumulation in *C. reinhardtii* cells using representative compounds of Formula Ia (FIG. 12A), Formula IIa (FIG. 12B), and Formula IIIa (FIG. 12C). Nile red fold-change values in the primary screening experiment at 10 µM final compound concentration (i) and Nile red fold-change values in the confirmatory screen at 10 μM compound concentration (ii) are provided for each compound. The scale bar of each image represents 5 μm.
Figure 12B:
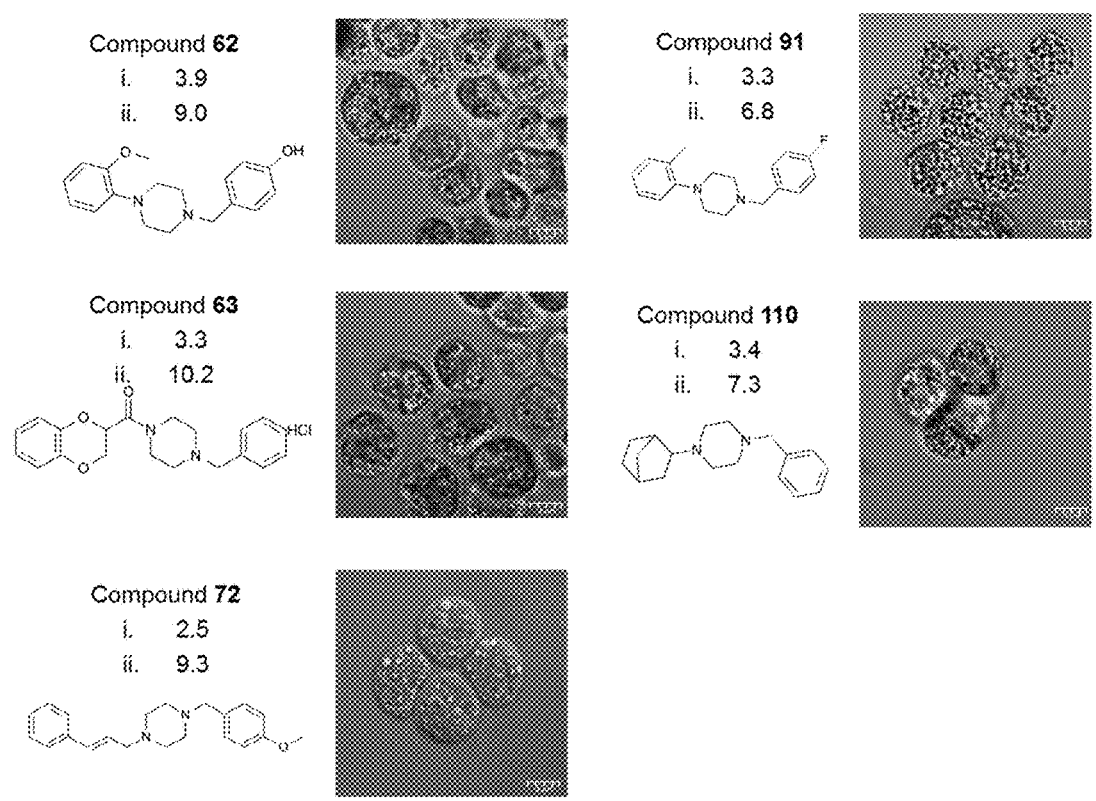
Figure 12C:
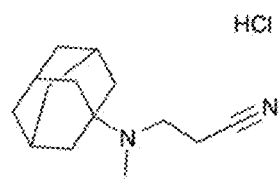
Figure 12C:
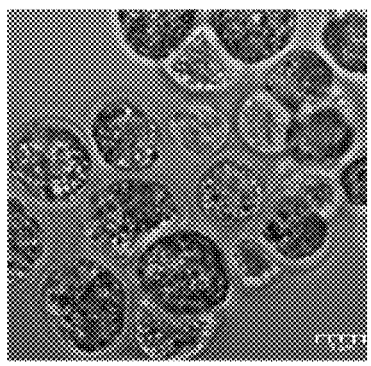
Figure 12C:
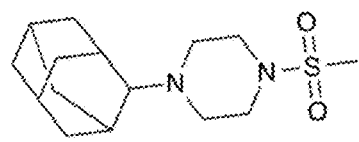
Figure 12C:
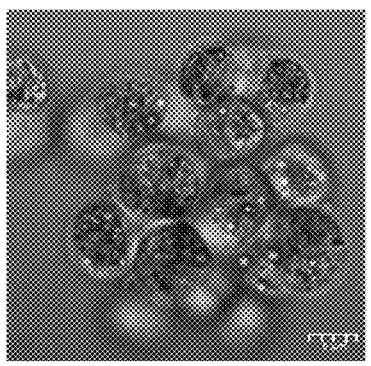

Representative compounds provided herein were shown to increase lipid accumulation using lipophilic dye Nile Red at concentrations ranging from 0.5 µM to 15.0 µM in *Chlamydomonas reinhardtii* cells, as shown in FIG. 3. Lipid accumulation over a period of 72 hours was also measured (30 µM test compound) using lipophilic dye Nile Red, as shown in FIG. 4. The increase of specific fatty acids and triglyercide accumulation was also demonstrated using compounds 1, 62, and 136 as shown in FIGS. 5-6 (compounds tested 30 µM for fatty acid assay and 5 µM for triglyceride assay). FIGS. 12A-12C show representative images of *C. reinhardtii* cultures that were treated with 10 µM of representative test compounds of Formula Ia, Formula IIa, and Formula IIIa. The corresponding lipid accumulation was visualized using confocal microscopy after 72 hours in culture.

Example 4. Cellular Chlorophyll, Protein, and Carbohydrate Levels

Figure 7:
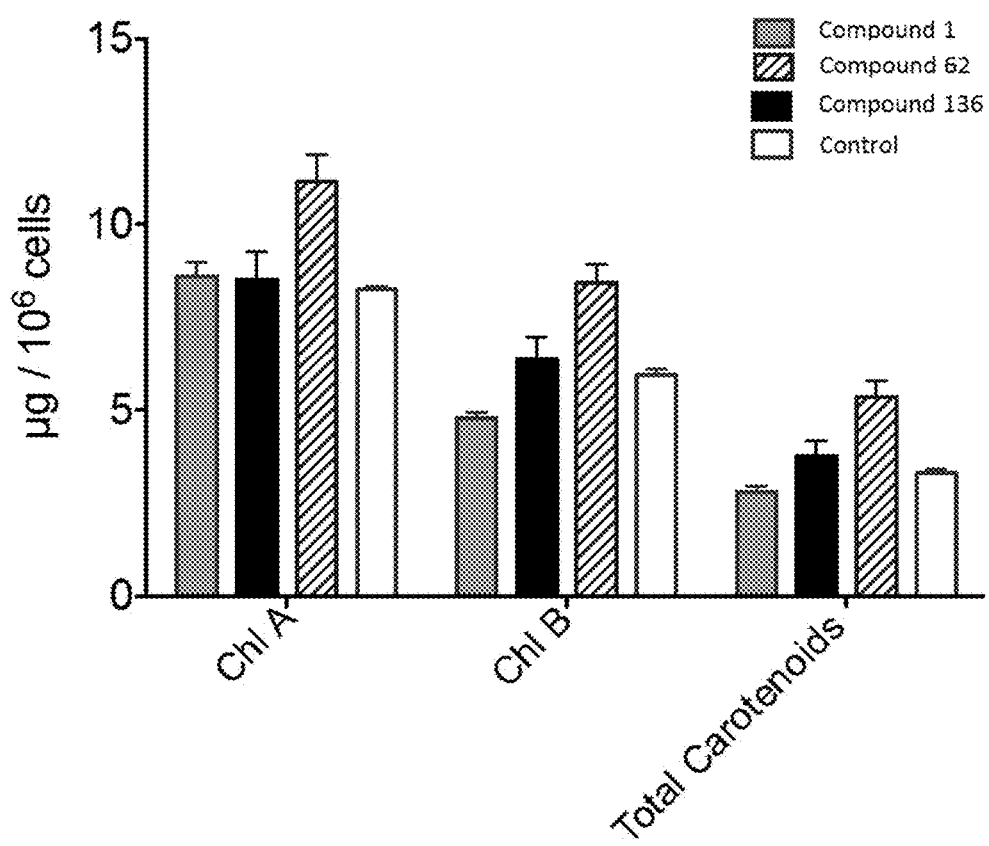
FIG. 7 shows the levels of chlorophyll A (Chl A), chlorophyll B (Chl B) and carotenoid in cells in the presence of compounds 1, 62, and 136.
Figure 8:
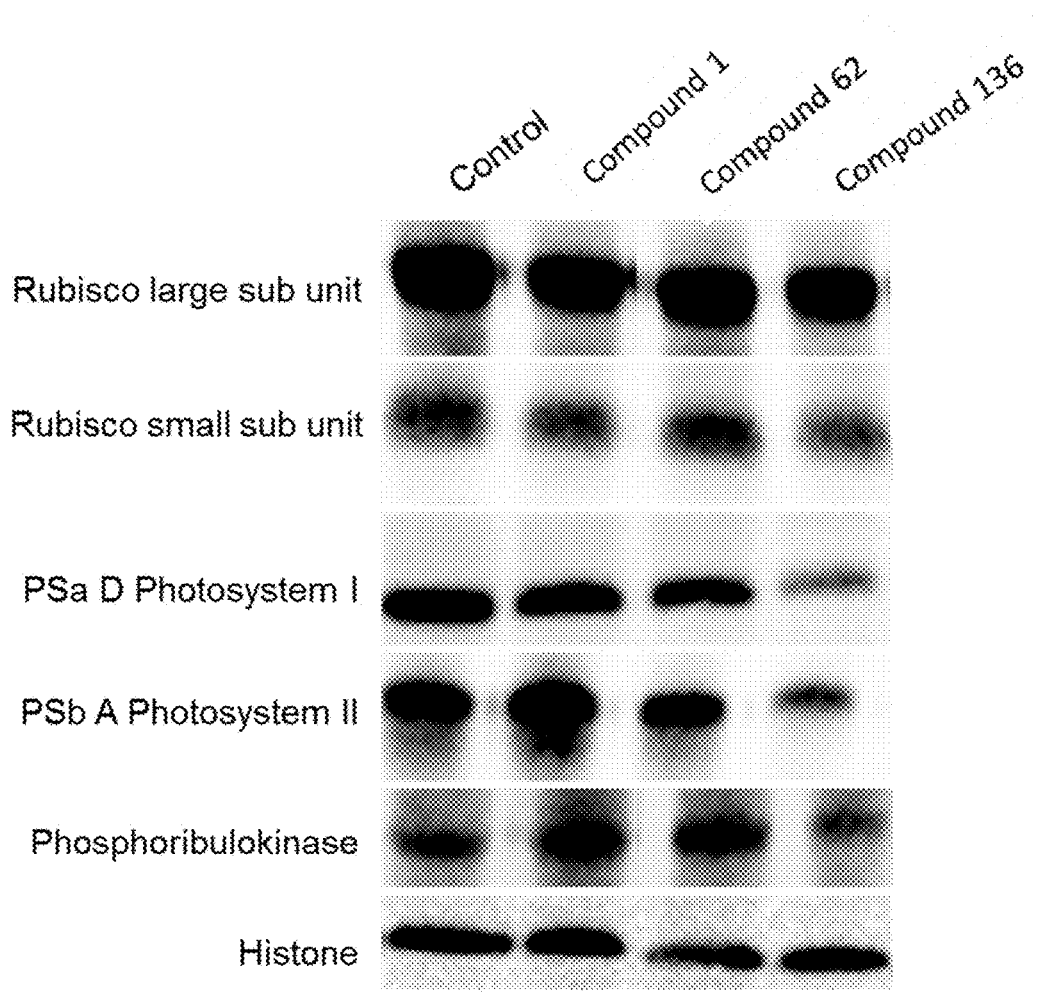
FIG. 8 shows the cellular effects of compounds 1, 62, and 136 on the levels of proteins required for photosynthesis.
Figure 9:
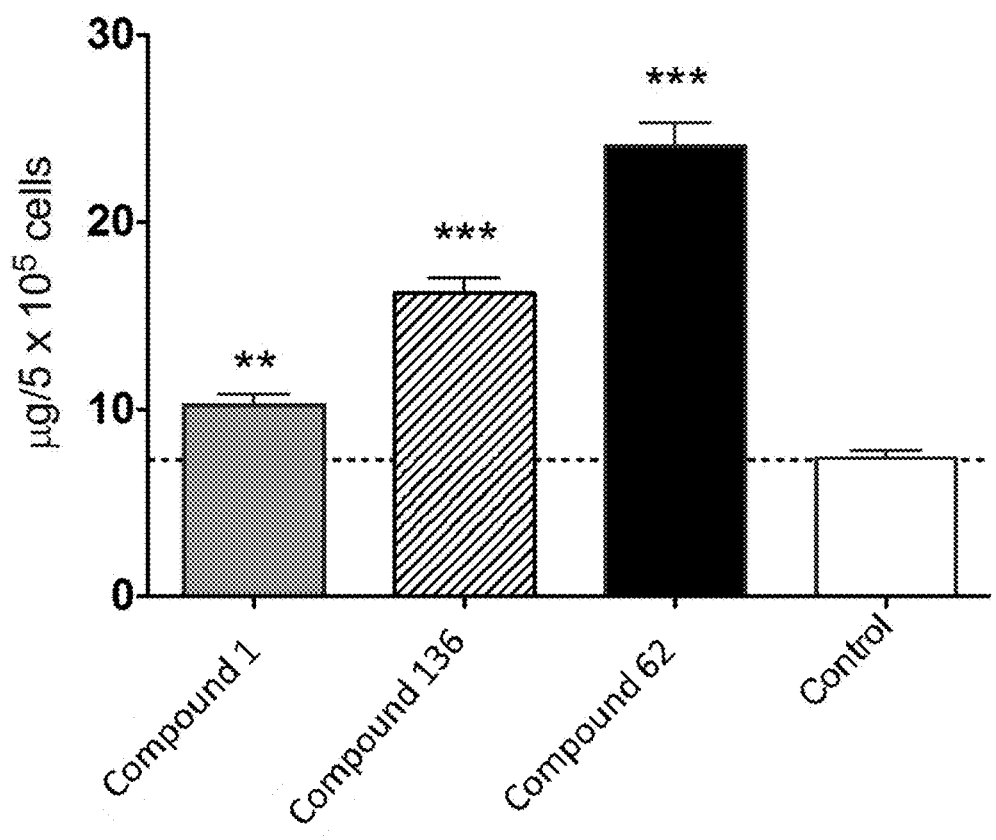
FIG. 9 shows increased carbohydrate levels in cells in the presence of compounds 1, 62, and 136.
Figure 10:
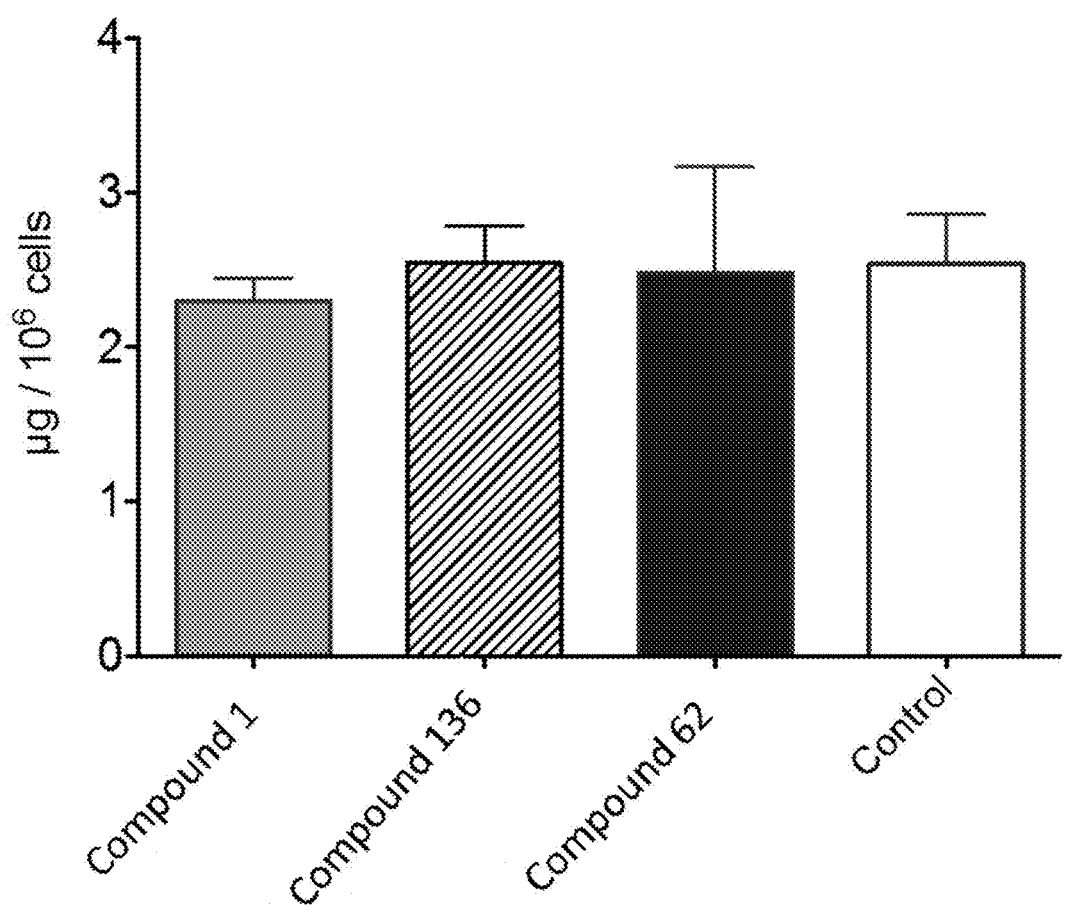
FIG. 10 shows the effect of compounds 1, 62, and 136 on the total level of proteins in cells.

Compounds 1, 62, and 136 (30 µM) did not significantly alter levels of chlorophyll A (Chl A), chlorophyll B (Chl B), or carotenoid levels in *Chlamydomonas reinhardtii* cells, as shown in FIG. 7. Further, compounds 1 and 136 did not significantly affect the levels of proteins required for photosynthesis (e.g., Rubisco large sub unit, Rubisco small sub unit, PSa D Photosystem I, PSb A Photosystem II, phosphoribulokinase, and histone, and compound 62 exhibited minor effects on the same proteins, as shown in FIG. 8. All three test compounds (30 µM) increased carbohydrate levels in *Chlamydomonas reinhardtii* cells, indicating stimulation of starch storage in addition to lipid storage, as shown in FIG. 9. None of the test compounds significantly affected total protein levels, as shown in FIG. 10.

Example 5. Lipid Accumulation in Algal Cells

Figure 11A:
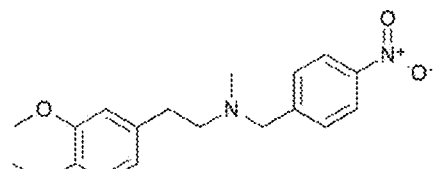
FIGS. 11A-11C show growth of various algal species in the presence of compound 1 (FIG. 11A), compound 62 (FIG. 11B), and compound 136 (FIG. 11C).
Figure 11A:
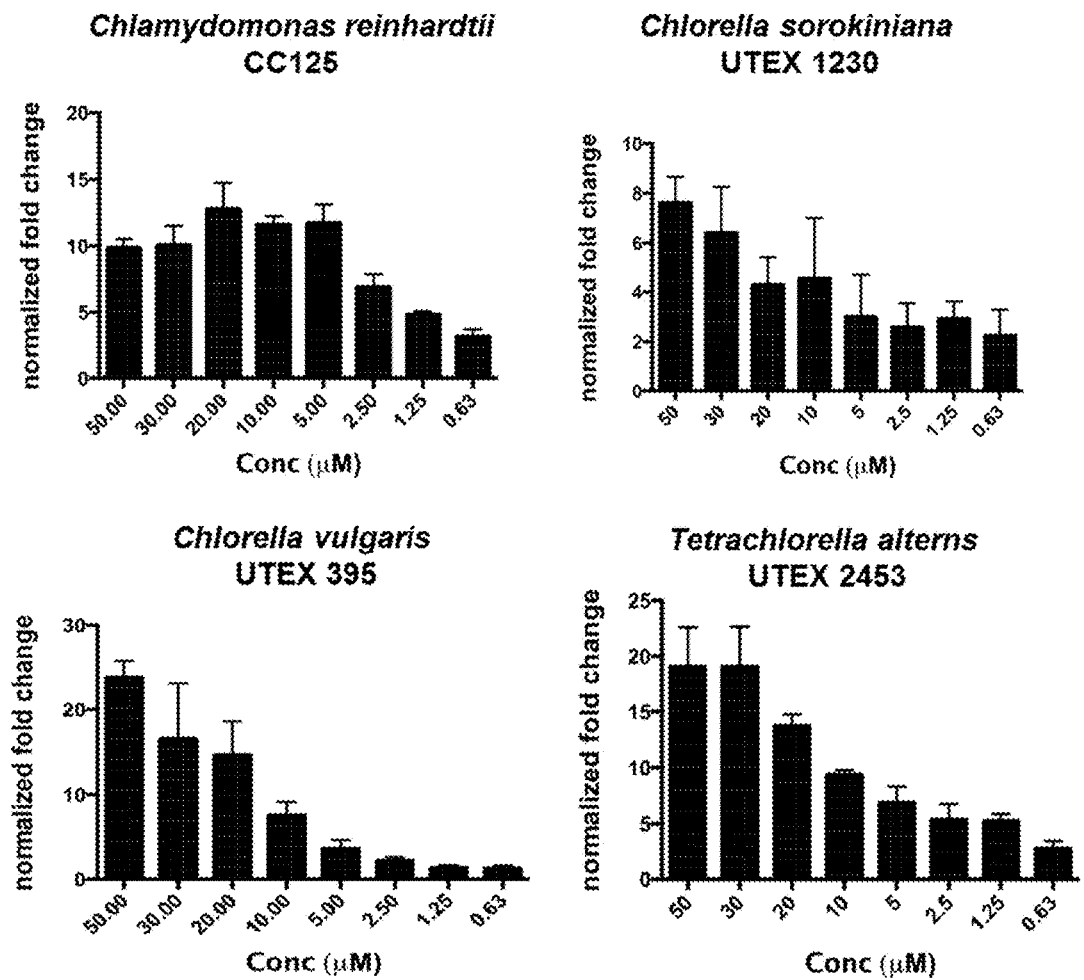
Figure 11B:
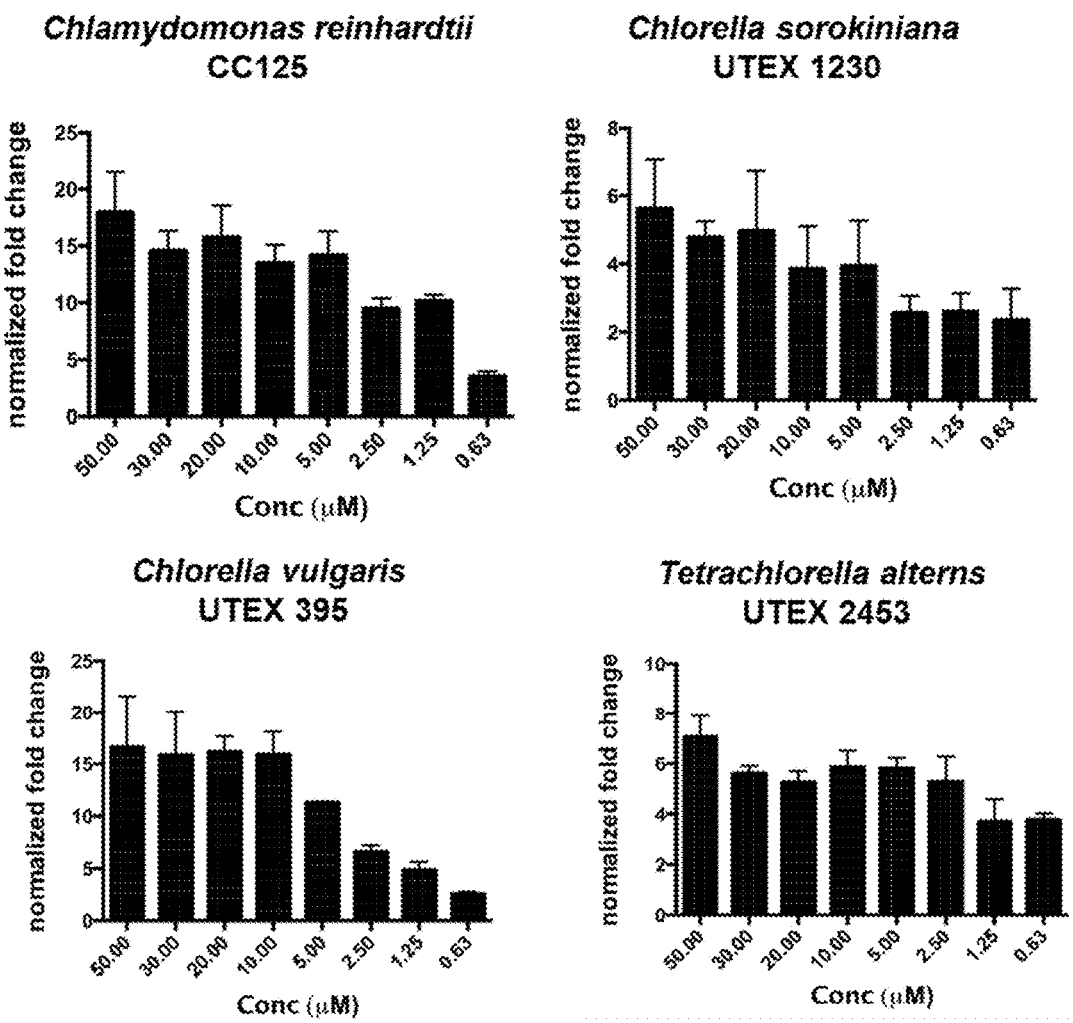
Figure 11C:
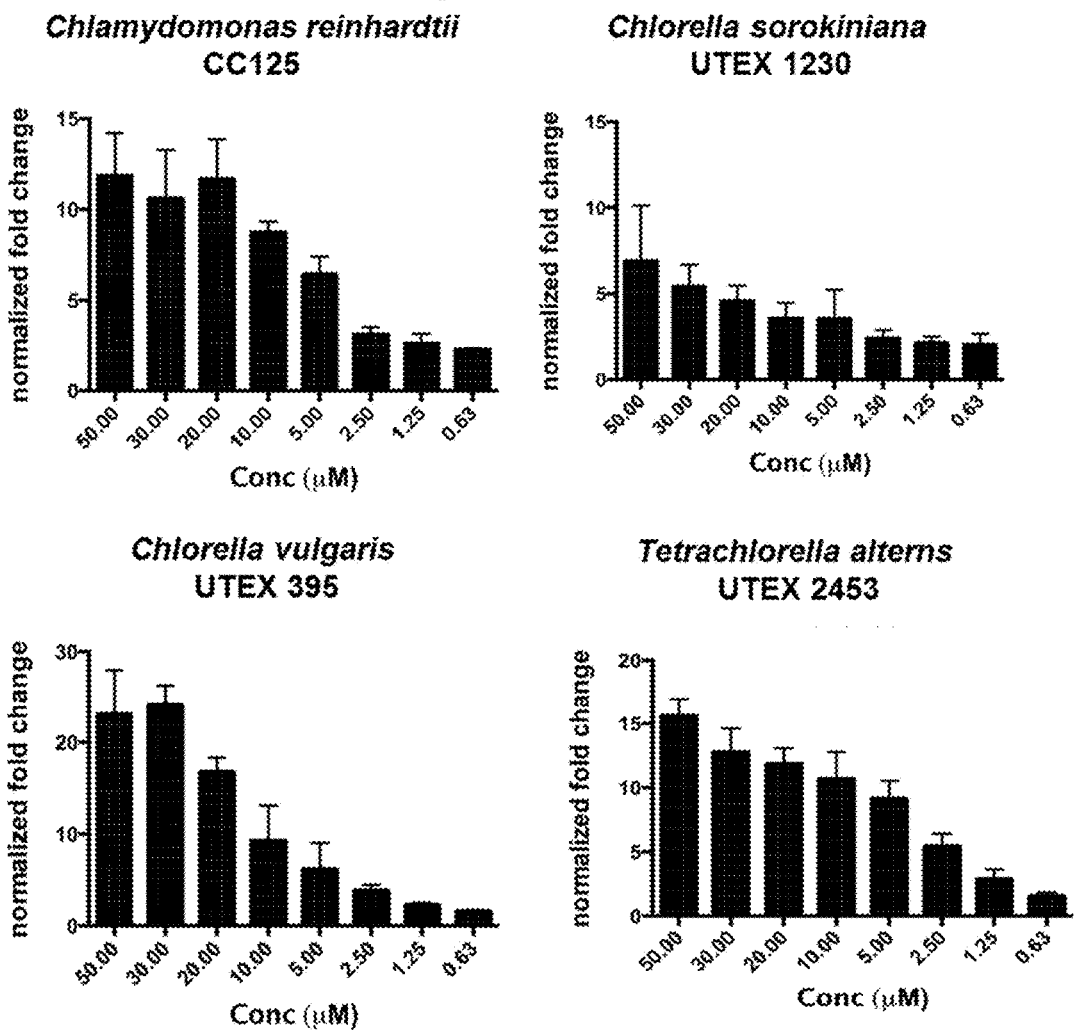

Compounds 1, 62, and 136 were assayed in algal species *Chlamydomonas reinhardtii* CC125, *Chlorella sorokiniana* UTEX 1230, *Chlorella vulgaris* UTEX 395, and *Tetrachlorella alterns* UTEX 2453 at concentrations ranging from 0.63 µM to 50 µM. All three test compounds stimulated lipid accumulation in each of the algal species, as shown in FIG. 11A-11C.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing lipid accumulation in an algal cell, comprising contacting the algal cell with an effective amount of a compound selected from the group consisting of:

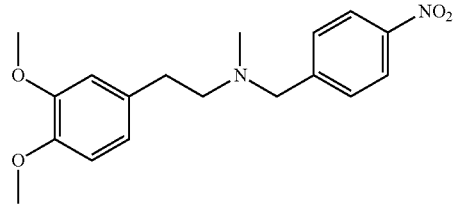
(1)

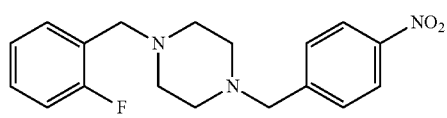
(29)

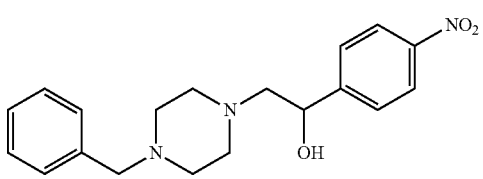
(31)

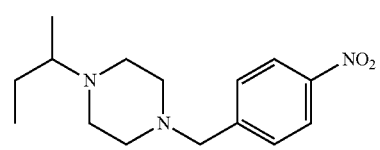
(40)

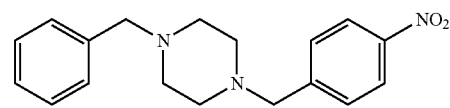
(6)

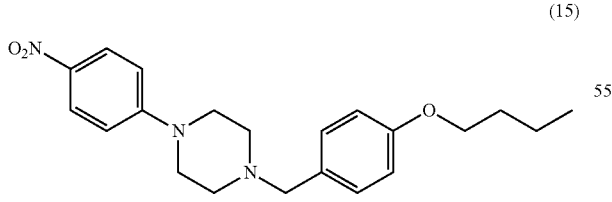
(15)

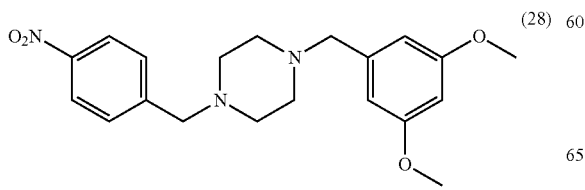
(28)

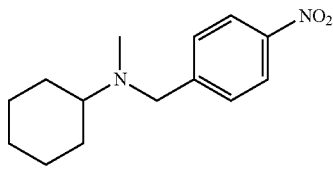
(14)

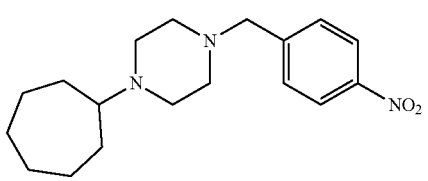
(43)

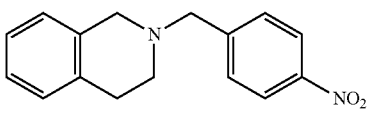
(3)

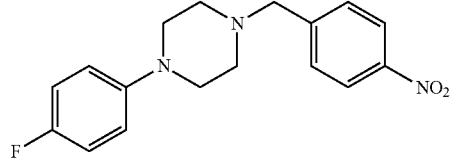
(9)

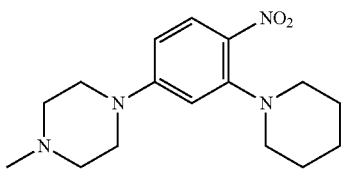
(33)

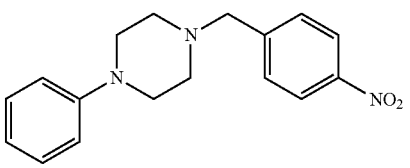
(7)

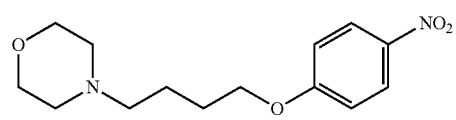
(12)

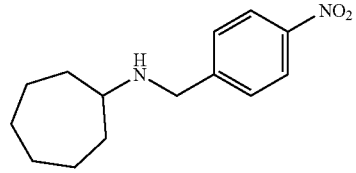
(19)

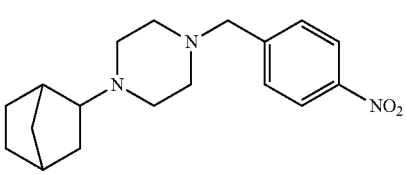
(41)

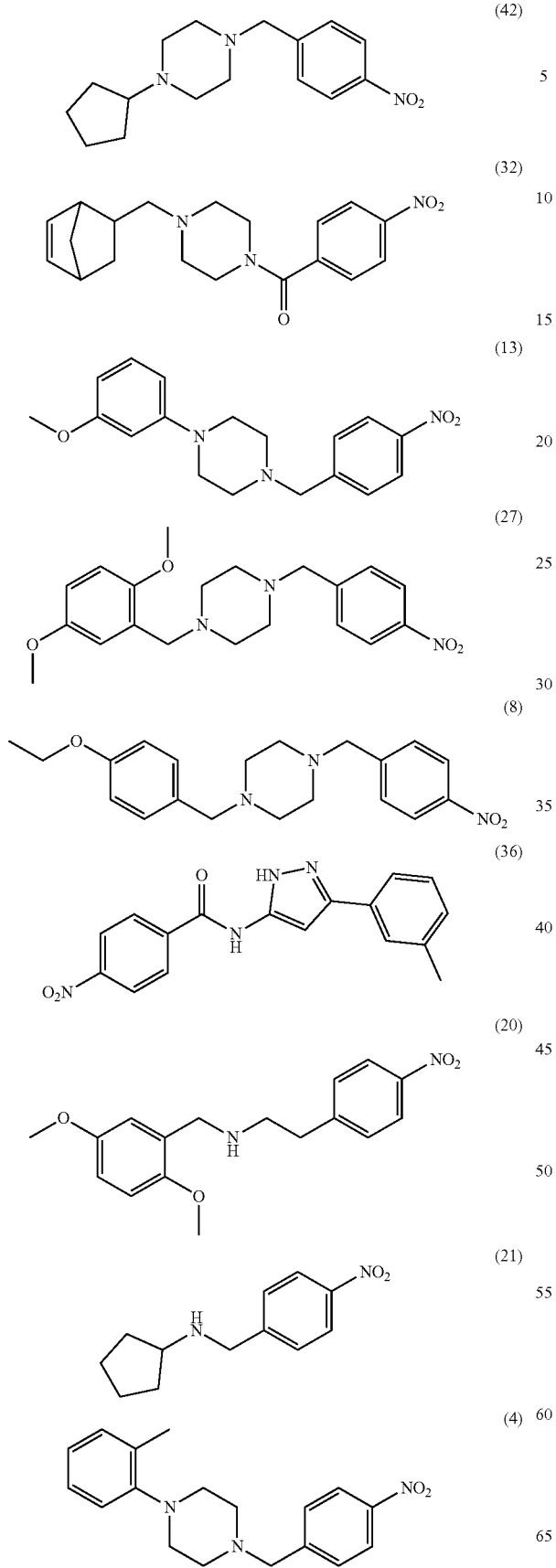
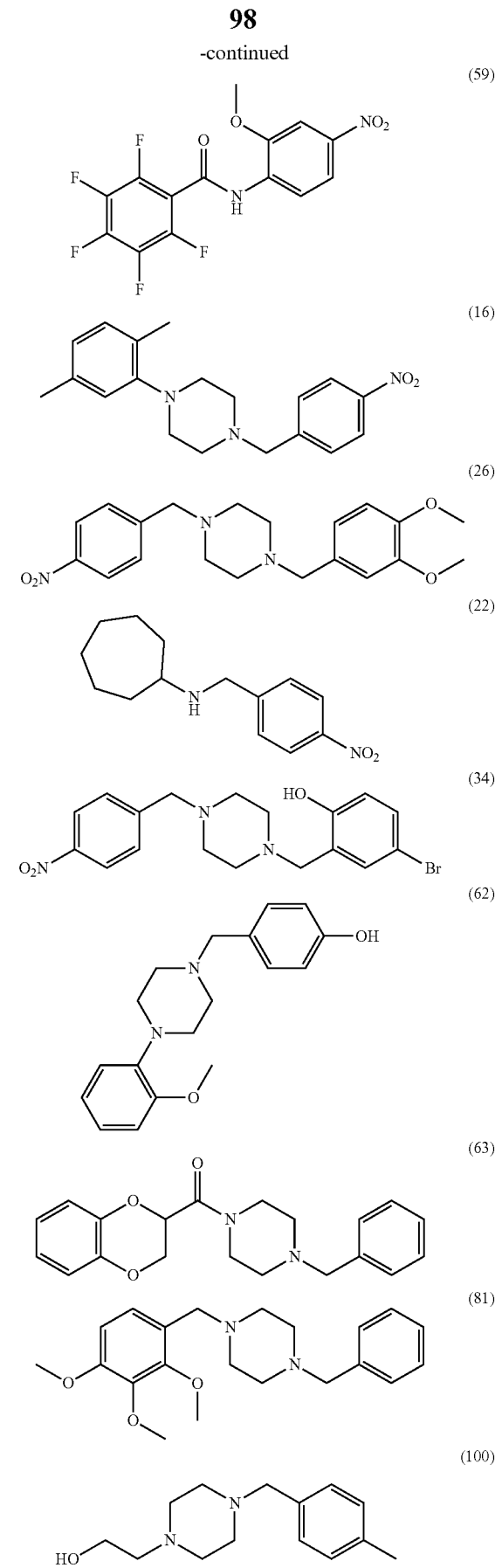

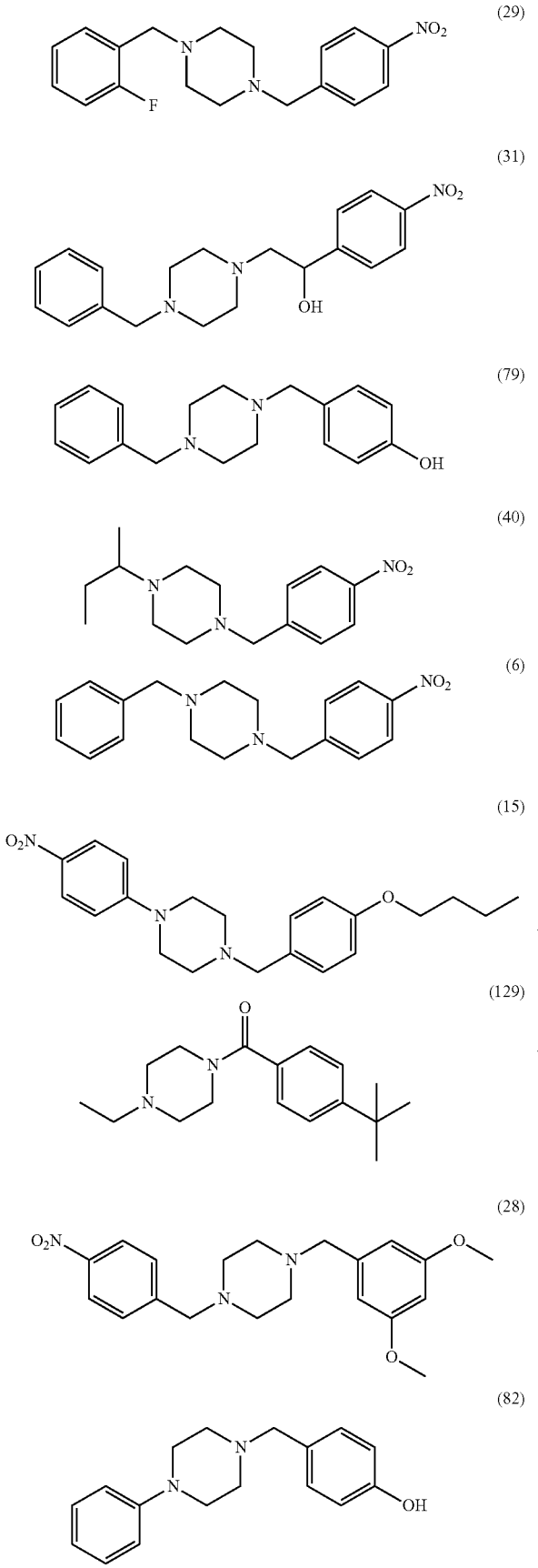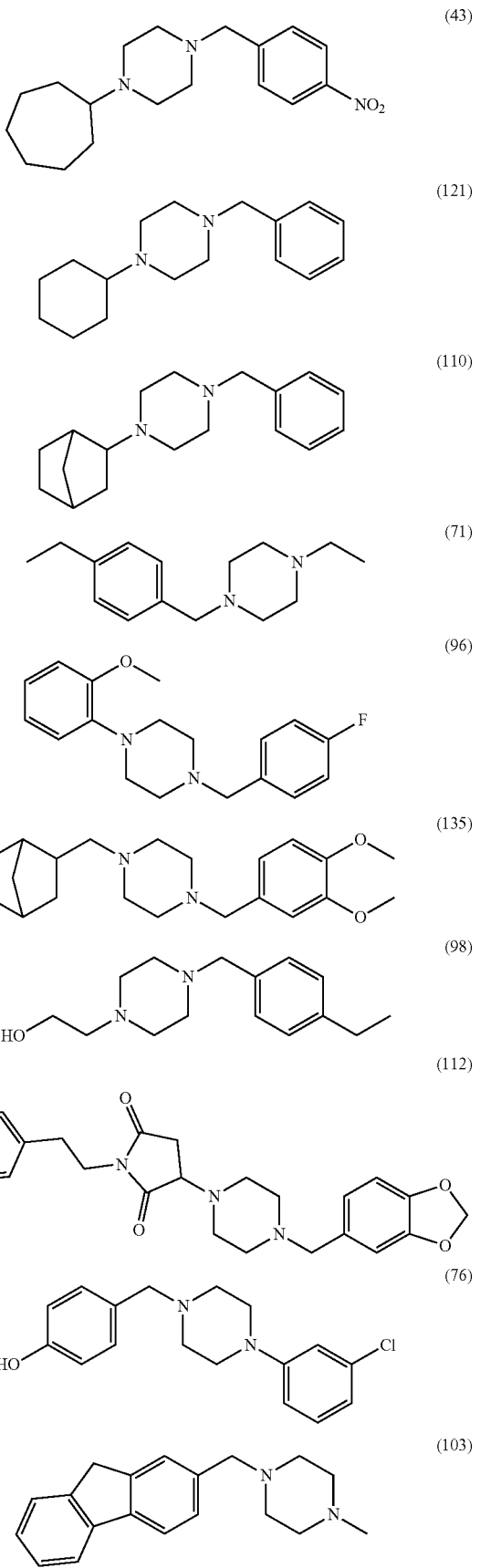

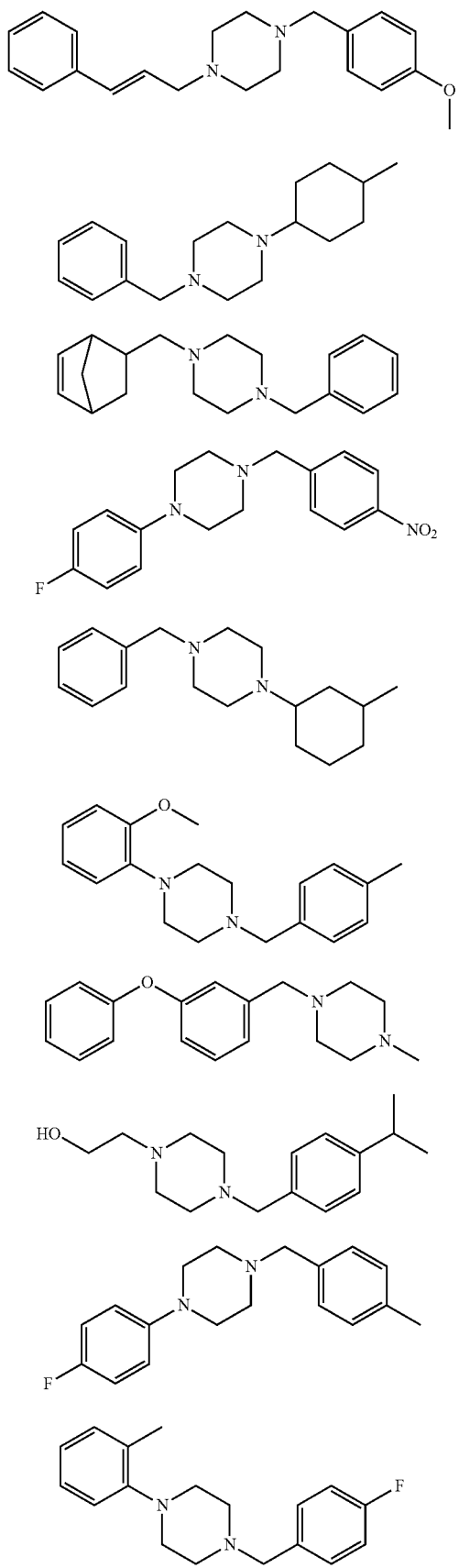
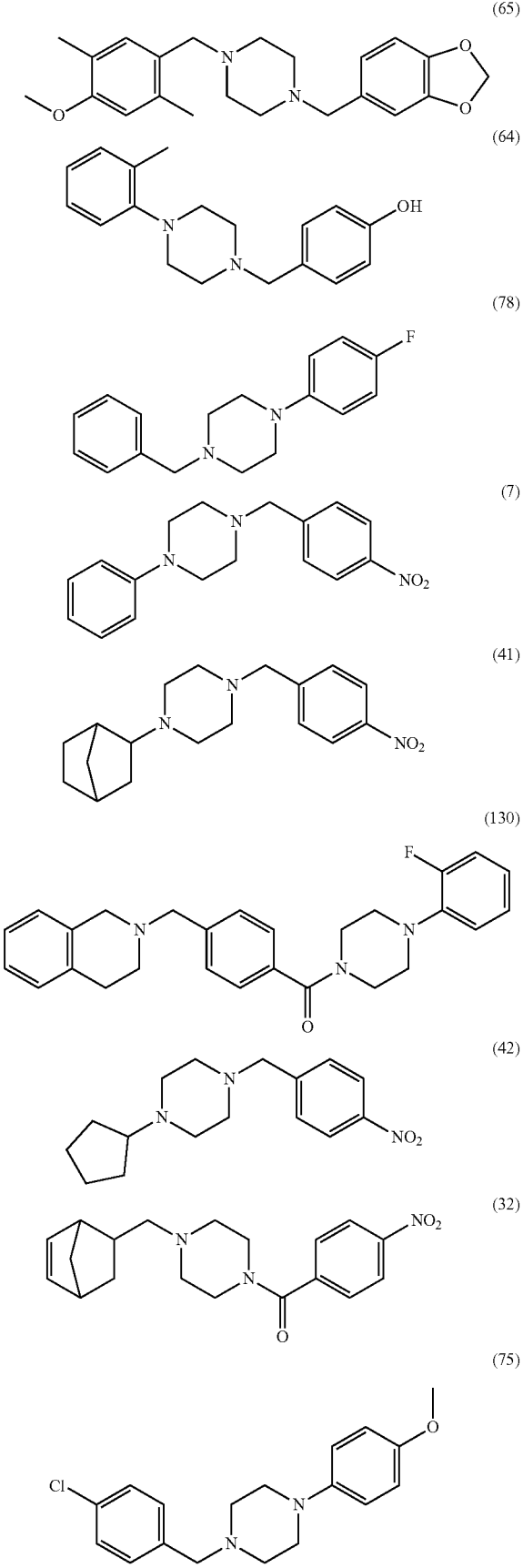

-continued
(94)
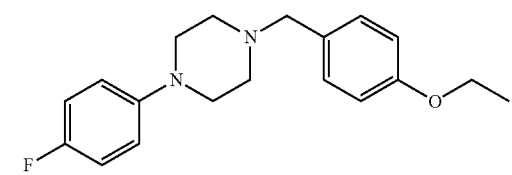
(13)
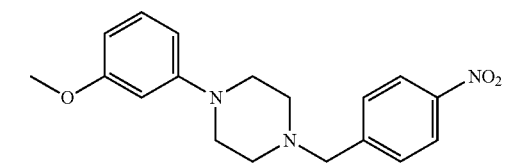
(8)
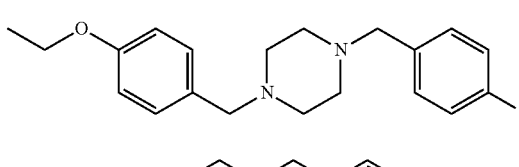
(66)
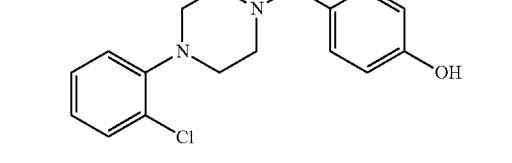
(27)
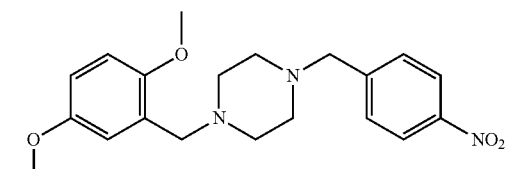
(88)
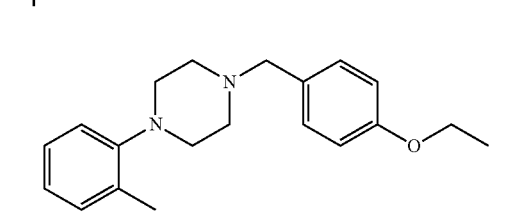
(4)
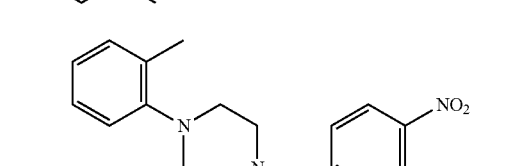
(132)
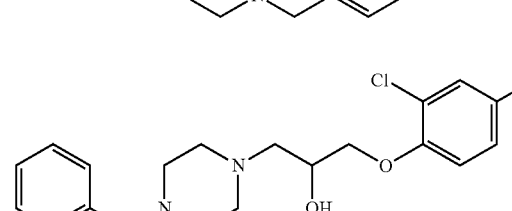
(77)
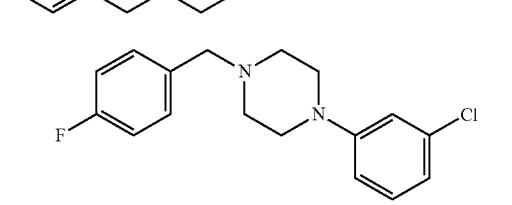
-continued
(67)
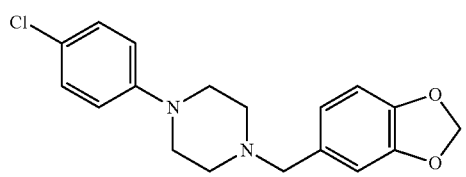
(133)
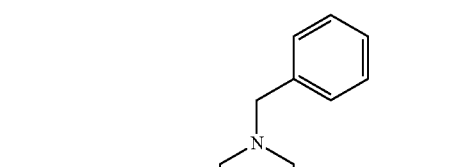
(113)
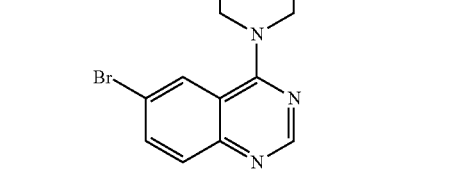
(16)
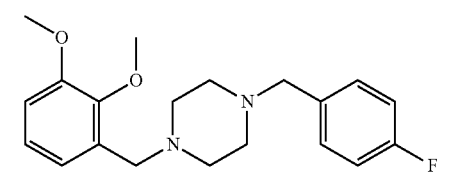
(26)
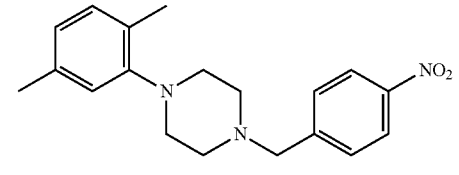
(34)
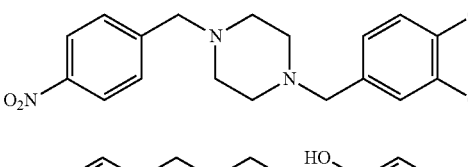
(131)
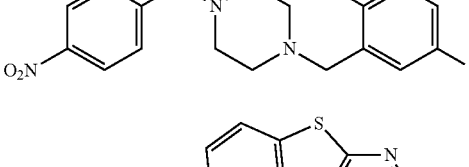
(123)
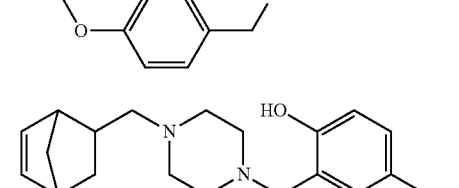

(95)
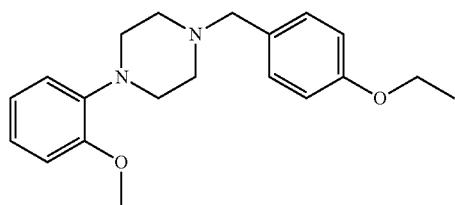
(144)
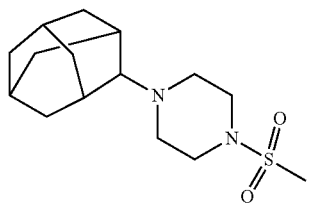
(136)
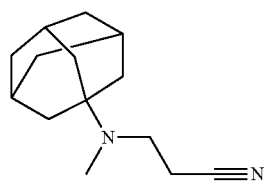
(143)
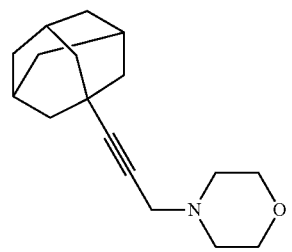
(149)
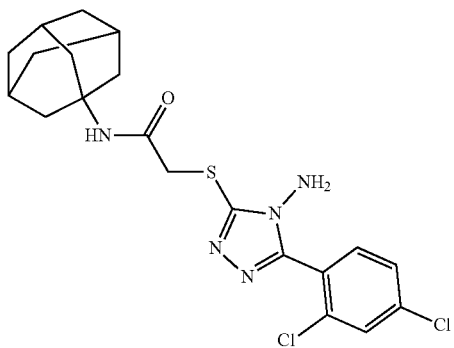
(138)
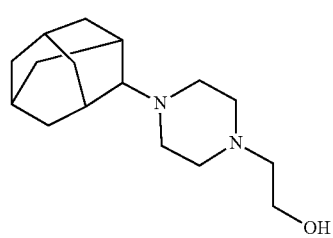
(145)
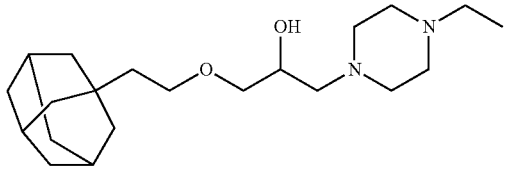
(137)
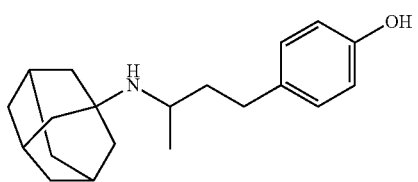
(139)
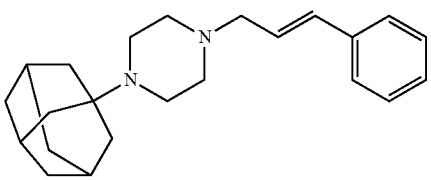
(140)
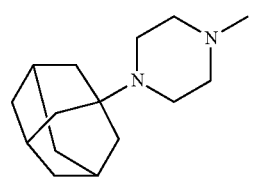
(146)
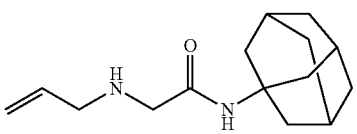
(142)
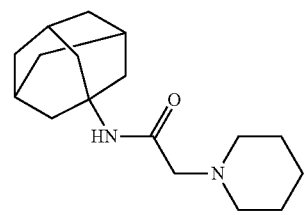
(147)
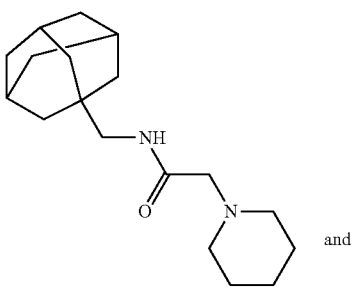
and
(141)
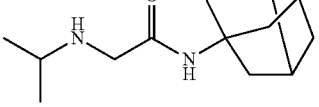
or a salt thereof, wherein the algal cell is selected from the group consisting of *Chlamydomonas reinhardtii*, *Chlorella sorokiniana*, *Chlorella vulgaris*, and *Tetrachlorella altems*.

2. A method of increasing lipid accumulation in an algal cell, comprising contacting the algal cell with an effective amount of a compound selected from the group consisting of:

(1)
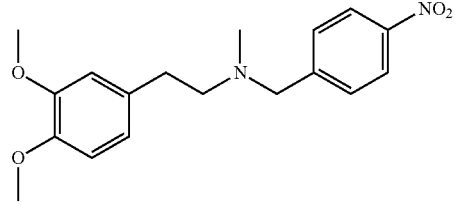

(62)
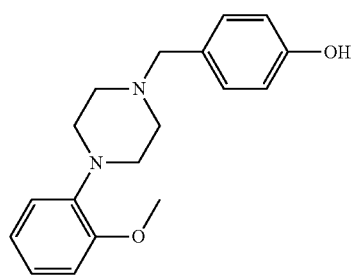

(136)
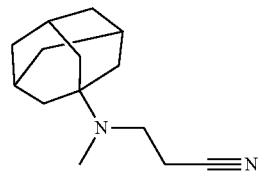

(14)
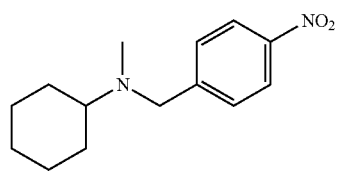

(63)
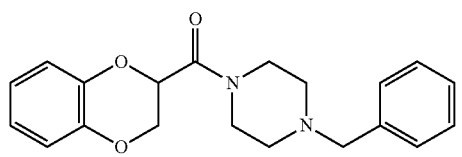

(72)
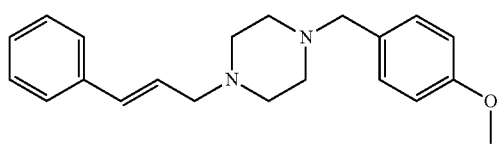

(91)
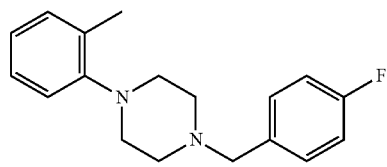

(110)
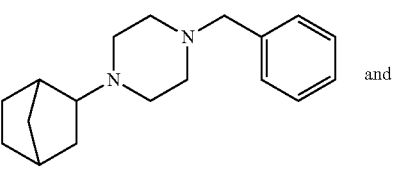

and (144)
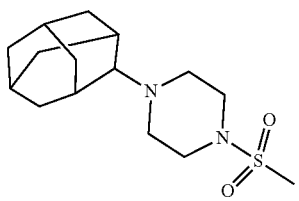

or a salt thereof,
wherein the algal cell is selected from the group consisting of:
*Chlamydomonas reinhardtii;*
*Chlorella sorokiniana;*
*Tetrachlorella alterans;*
*C. protothecoides;*
*C. vulgaris;* and
*Nannochloropsis* sp.

3. The method of claim 2, wherein the algal cell is selected from the group consisting of *Chlamydomonas reinhardtii*, *Chlorella sorokiniana*, *Chlorella vulgaris*, and *Tetrachlorella altems*.

4. The method of claim 2, wherein the compound is selected from the group consisting of:

(1)
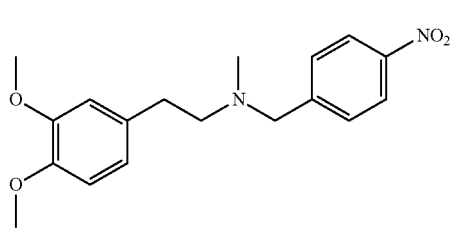

(62)
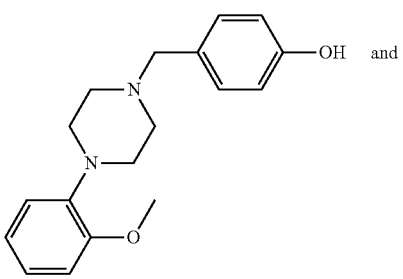

and (136)
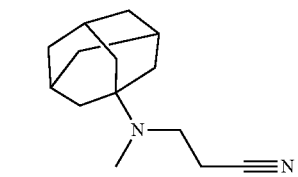

or a salt thereof, wherein the algal cell is selected from the group consisting of:

Chlamydomonas reinhardtii;

Chlorella sorokiniana;

Tetrachlorella alterans;

C. protothecoides;

C. vulgaris; and

Nannochloropsis sp.

5. The method of claim 4, wherein the algal cell is selected from the group consisting of Chlamydomonas reinhardtii, Chlorella sorokiniana, Chlorella vulgaris, and Tetrachlorella altems.

6. The method of claim 5, wherein the compound is:

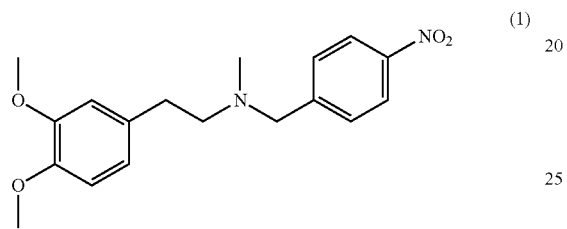
(1)

or a salt thereof.

7. The method of claim 5, wherein the compound is:

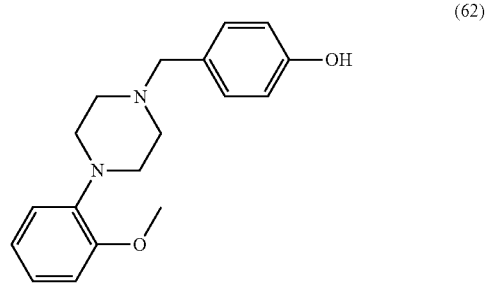 [SMILES: COc1ccccc1N1CCN(Cc2ccc(O)cc2)CC1]
(62)

or a salt thereof.

8. The method of claim 5, wherein the compound is:

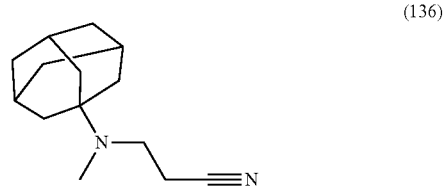 [SMILES: CN(CCC#N)C12CC3CC(CC(C3)C1)C2]
(136)

or a salt thereof.

* * * * *